(12) United States Patent
Lo et al.

(10) Patent No.: US 10,781,490 B2
(45) Date of Patent: Sep. 22, 2020

(54) DETECTING HEMATOLOGICAL DISORDERS USING CELL-FREE DNA IN BLOOD

(71) Applicant: The Chinese University of Hong Kong, Shatin (HK)

(72) Inventors: Yuk-Ming Dennis Lo, Homantin (CN); Rossa Wai Kwun Chiu, Shatin (CN); Kwan Chee Chan, Shatin (CN); Kun Sun, Shatin (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 0 days.

(21) Appl. No.: 15/608,863

(22) Filed: May 30, 2017

(65) Prior Publication Data

US 2017/0349948 A1    Dec. 7, 2017

Related U.S. Application Data

(60) Provisional application No. 62/343,050, filed on May 30, 2016.

(51) Int. Cl.
*C12Q 1/6883* (2018.01)
*C12Q 1/6888* (2018.01)

(52) U.S. Cl.
CPC ......... *C12Q 1/6883* (2013.01); *C12Q 1/6888* (2013.01); *C12Q 2600/106* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 9,732,390 B2* | 8/2017 | Lo | C12Q 1/6881 |
| 2005/0221314 A1 | 10/2005 | Berlin et al. | |
| 2009/0176655 A1 | 7/2009 | Esteller | |
| 2011/0028333 A1 | 2/2011 | Christensen et al. | |
| 2014/0080715 A1 | 3/2014 | Lo et al. | |
| 2014/0178348 A1 | 6/2014 | Kelsey et al. | |
| 2016/0017419 A1 | 1/2016 | Chiu et al. | |
| 2016/0340740 A1 | 11/2016 | Zhang | |
| 2017/0121767 A1 | 5/2017 | Dor et al. | |

FOREIGN PATENT DOCUMENTS

| | | |
|---|---|---|
| WO | 2011092592 A2 | 8/2011 |
| WO | 2011130751 A1 | 10/2011 |
| WO | 2012071621 A1 | 6/2012 |
| WO | 2012103031 A2 | 8/2012 |
| WO | 2013045432 A1 | 4/2013 |
| WO | 2013066641 A1 | 5/2013 |
| WO | 2014043763 A1 | 3/2014 |
| WO | 2015159292 A2 | 10/2015 |
| WO | 2015169947 A1 | 11/2015 |
| WO | 2015159292 A3 | 12/2015 |
| WO | 2016008451 A1 | 1/2016 |
| WO | 2016112850 A1 | 7/2016 |

OTHER PUBLICATIONS

Warton et al Frontiers in Molecular Biosciences. Apr. 22, 2015. 2: Article 13, pp. 1-10.*
Liggett J Neurological Sciences. 2010. 290: 16-21.*
Sun, Kun et al.; "Plasma DNA tissue mapping by genome-wide methylation sequencing for noninvasive prenatal, cancer, and transplantation assessments"; PNAS; Published online Sep. 21, 2015; doi: 10.1073/pnas.1508736112; E5503-E5512 (15 pages).
Chan, K.C. Allen et al.; "Noninvasive detection of cancer-associated genome-wide hypomethylation and copy number aberrations by plasma DNA bisulfite sequencing"; PNAS; Nov. 13, 2013; vol. 110, No. 47; pp. 18761-18768.
Lui, Yanni Y.N. et al.; "Predominant Hematopoietic Origin of Cell-free DNA in Plasma and Serum after Sex-mismatched Bone Marrow Transplantation"; Clinical Chemistry; Mar. 2002; vol. 48, No. 3; pp. 421-427.
International Search Report and Written Opinion dated Aug. 25, 2017 in International Application No. PCT/CN2017/086509. 11 pages.
Houseman, Eugene Andres et al.; "Reference-free cell mixture adjustments in analysis of DNA methylation data"; Bioinformatics; Advance Access publication Jan. 21, 2014; vol. 30, No. 10; pp. 1431-1439.
Houseman, Eugene Andres et al.; "DNA methylation arrays as surrogate measures of cell mixture distribution"; BMC Bioinformatics; 2012; vol. 13, No. 86; 16 pages.
Houseman, E. Andres et al.; "Cell-composition effects in the analysis of DNA methylation array data: a mathematical perspective"; BMC Bioinformatics; 2015; vol. 16, No. 95; 16 pages.
Accomando, William, P. et al.; "Quantitative reconstruction of leukocyte subsets using DNA methylation"; Genome Biology; 2014; vol. 15, No. R50; 12 pages.
Koh, Winston et al.; "Noninvasive in vivo monitoring of tissue-specific global gene expression in humans"; PNAS; May 20, 2014; vol. 111, No. 20; pp. 7361-7366, plus 10 pages of "Supporting Information" (17 total pages).

(Continued)

*Primary Examiner* — Carla J Myers
(74) *Attorney, Agent, or Firm* — Kilpatrick Townsend & Stockton LLP

(57) ABSTRACT

Techniques are provided for detecting hematological disorders using cell-free DNA in a blood sample, e.g., using plasma or serum. For example, an assay can target one or more differentially-methylated regions specific to a particular hematological cell lineage (e.g., erythroblasts). A methylation level can be quantified from the assay to determine an amount of methylated or unmethylated DNA fragments in a cell-free mixture of the blood sample. The methylation level can be compared to one or more cutoff values, e.g., that correspond to a normal range for the particular hematological cell lineage as part of determining a level of a hematological disorder.

23 Claims, 30 Drawing Sheets
(12 of 30 Drawing Sheet(s) Filed in Color)
Specification includes a Sequence Listing.

(56) References Cited

OTHER PUBLICATIONS

Fernandez, Agustin, F. et al.; "A DNA methylation fingerprint of 1628 human samples"; Genome Research; 2012; vol. 22; pp. 407-419 (14 total pages).

Gil, M.M. et al.; "Analysis of cell-free DNA in maternal blood in screening for fetal aneuploidies: updated meta-analysis"; Ultrasound in Obstetrics & Gynecology; 2015; vol. 45, Issue 3; pp. 249-266.

Lo, Y.M. Dennis et al.; "Maternal Plasma DNA Sequencing Reveals the Genome-Wide Genetic and Mutational Profile of the Fetus"; Science Translational Medicine; Published Dec. 8, 2010; vol. 2, Issue 61; 61ra91; pp. 1-13; plus 60 pages of "Supporting Online Material" (73 total pages).

Flanagan, James M. et al.; "DNA Methylome of Familial Breast Cancer Identifies Distinct Profiles Defined by Mutation Status"; The American Journal of Human Genetics; Mar. 2010; vol. 86, Issue 3; pp. 420-433.

Ogoshi, Katsumi et al.; "Genome-wide profiling of DNA methylation in human cancer cells"; Genomics; 2011; vol. 98, Issue 4; pp. 280-287.

Yuen, Ryan K.C. et al.; "Genome-wide mapping of imprinted differentially methylated regions by DNA methylation profiling of human placentas from triploidies"; Epigenetics & Chromatin; 2011; vol. 4, No. 10; 16 pages.

Saied, Marwa H. et al.; "Genome Wide Analysis of Acute Myeloid Leukemia Reveal Leukemia Specific Methylome and Subtype Specific Hypomethylation of Repeats"; PLoS One; Mar. 2012; vol. 7, Issue 3; e33213; 12 pages.

Kuo, Hsien-Chi et al.; "DBCAT: Database of CpG Islands and Analytical Tools for Identifying Comprehensive Methylation Profiles in Cancer Cells"; Journal of Computational Biology; Aug. 2011; vol. 18, No. 8; pp. 1013-1017 (6 total pages).

Price, E. Magda et al.; "Different measures of 'genome-wide' DNA methylation exhibit unique properties in placental and somatic tissues"; Epigenetics; Jun. 2012; vol. 7, Issue 6; pp. 652-663 (13 total pages).

Guo, Shicheng et al.; "Identification of methylation haplotype blocks aids in deconvolution of heterogeneous tissue samples and tumor tissue-of-origin mapping from plasma DNA"; Nature Genetics; Published in final edited form Apr. 2017, vol. 49, pp. 635-642; Author Manuscript available in PMC Sep. 6, 2017; 21 pages.

Chim, Stephen, S.C. et al.; "Detection of the placental epigenetic signature of the maspin gene in maternal plasma"; PNAS; Oct. 11, 2005; vol. 102, No. 41; pp. 14753-14758.

Vollmers, Christopher et al.; "Monitoring Pharmacologically Induced Immunosuppression by Immune Repertoire Sequencing to Detect Acute Allograft Rejection in Heart Transplant Patients: A Proof-of-Concept Diagnostic Accuracy Study"; PLoS Medicine; Oct. 14, 2015; doi: 10.1371/journal.pmed.1001890; vol. 12, Issue 10; 17 pages.

Snyder, Matthew W. et al.; "Cell-free DNA Comprises an In Vivo Nucleosome Footprint that Informs Its Tissues-of-Origin"; Cell; Jan. 14, 2016; 164; 57-68 (30 pages).

Extended European Search Report dated Nov. 13, 2019 in EP Patent Application No. 17805833.5. 11 pages.

Iriyama, Chisako et al.; "Using peripheral blood circulating DNAs to detect CpG global methylation status and genetic mutations in patients with myelodysplastic syndrome"; Biochemical and Biophysical Research Communications; Mar. 23, 2012; doi: 10.1016/j.bbrc.2012.02.071; vol. 419, Issue 4; pp. 662-669.

Korabecna, Marie et al.; "Methylation Status of Immune Response Genes Promoters in Cell-Free DNA Differs in Hemodialyzed Patients with Diabetic Nephropathy According to the Intensity of Anemia Therapy"; Blood Purification; Published online: Dec. 20, 2013; vol. 36; pp. 280-286.

Written Opinion dated Apr. 18, 2020 in SG Patent Application No. 20181110544W. 10 pages.

\* cited by examiner

DETECTING HEMATOLOGICAL DISORDERS USING CELL-FREE DNA IN BLOOD

CROSS-REFERENCES TO RELATED APPLICATIONS

The present application claims priority from and is a nonprovisional application of U.S. Provisional Application No. 62/343,050, entitled "Detecting Hematological Disorders Using Cell-Free DNA In Blood" filed May 30, 2016, the entire contents of which are herein incorporated by reference for all purposes.

BACKGROUND

To determine whether a hematological disorder (e.g., anemia) exists in a person, conventional techniques perform a histological examination of a bone marrow biopsy. However, a bone marrow biopsy is an invasive procedure leading to pain and anxiety for patients undergoing such a procedure. Therefore, it is desirable to identify new techniques to detect and characterize hematological disorders in a person.

Anemia can be caused by multiple clinical conditions, each with its own treatment. Hence, it would be clinically useful to ascertain the cause of a case of anemia, and then further investigate or treat accordingly. One cause of anemia is deficiency of a nutrient necessary for erythropoiesis (process for producing red blood cells), such as, but not limited to, iron, B12, folate, etc. Another cause of anemia is blood loss, which can be acute or chronic. The blood loss can be caused by, for example, menorrhagia or bleeding from the gastrointestinal tract. Anemia is also frequently found in many chronic disorders, also called the anemia of chronic disease, which can be found in cancer and inflammatory bowel diseases.

Accordingly, it is desirable to provide new techniques for screening subjects for a hematological disorder, for determining a cause of a hematological disorder, for monitoring a subject with a hematological disorder, and/or determining a proper treatment of a subject with a hematological disorder.

BRIEF SUMMARY

Some embodiments provide systems, methods, and apparatuses for detecting hematological disorders using cell-free DNA in a blood sample, e.g., using plasma or serum. For example, an assay can target one or more differentially-methylated regions specific to a particular hematological cell lineage (e.g., erythroblasts). A methylation level can be quantified from the assay to determine an amount of methylated or unmethylated DNA fragments in a cell-free mixture of the blood sample. The methylation level can be compared to one or more cutoff values, e.g., that correspond to a normal range for the particular hematological cell lineage as part of determining a level of a hematological disorder. Some embodiments can measure an amount of DNA from the particular hematological cell lineage (e.g., erythroblast DNA) in a blood sample in a similar manner using one or more methylation levels.

Such an analysis can provide a detection of a hematological disorder without performing the invasive procedure of a bone marrow biopsy. For example, our results demonstrate that bone marrow cells contribute a significant proportion to the circulating cell-free DNA. An analysis of the methylation signatures of the hematopoietic cells in the circulating cell-free DNA can reflect the status of the bone marrow cells. Such embodiments can be particularly useful for the monitoring of response of the bone marrow to treatments, for example, the response to oral iron therapy in patients with iron deficiency anemia. Embodiments can also be used for assigning patients for different procedures, e.g., a bone marrow biopsy or less invasive investigations.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

TERMS

Figure 1:
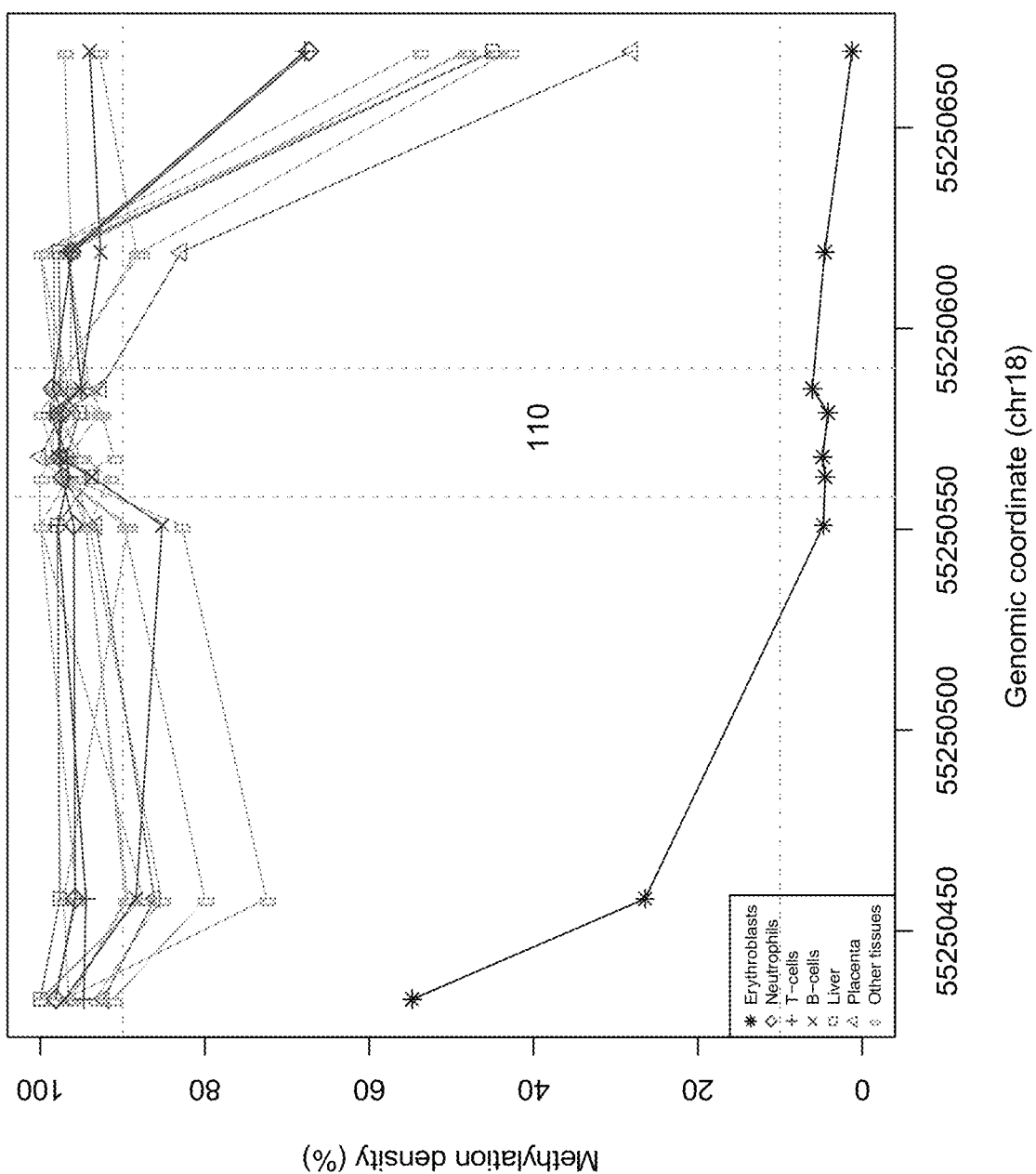
FIG. 1 shows methylation densities of the CpG sites within the promoter of the ferrochelatase (FECH) gene according to embodiments of the present invention.

A "methylome" provides a measure of an amount of DNA methylation at a plurality of sites or loci in a genome. The methylome may correspond to all of the genome, a substantial part of the genome, or relatively small portion(s) of the genome.

A "cell lineage" denotes the developmental history of a tissue or organ from the fertilized embryo. Different types of tissue (e.g., different types of blood cells) will have different cell lineages. Red blood cells (RBCs) are derived from proerythroblasts through a series of intermediate cells. Proerythroblasts, megakaryoblasts, and myeloblasts are derived from the common myeloid progenitor cells. The lymphocytes are derived from the common lymphoid progenitor cells. Nucleated RBCs are erythroblasts, immature enucleated RBCs are reticulocytes, and mature enucleated RBCs are erythrocytes, which are the red blood cells in the blood stream that carry hemoglobin.

A "cell-free mixture" corresponds to a sample that includes cell-free DNA fragments from various cells. For example, the cell-free mixture can include cell-free DNA fragments from various cell lineages. Plasma and serum are examples of a cell-free mixture obtained from a blood sample, e.g., via centrifuging. Other cell-free mixtures can be from other biological samples. A "biological sample" refers to any sample that is taken from a subject (e.g., a human, such as a pregnant woman, a person with cancer or a person suspected of having cancer, an organ transplant recipient, or a subject suspected of having a disease process involving an organ, such as the heart in myocardial infarction, the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), or vaginal flushing fluids, pleural fluid, ascitic fluid, cerebrospinal fluid, saliva, sweat, tears, sputum, bronchoalveolar lavage fluid, etc. Stool samples can also be used. In various embodiments, the majority of DNA in a biological sample that has been enriched for cell-free DNA (e.g., a plasma sample obtained via a centrifugation protocol) can be cell-free (as opposed to cells), e.g., greater than 50%, 60%, 70%, 80%, 90%, 95%, or 99%. The centrifugation protocol can include 3,000 g×10 minutes, obtaining the fluid part, and re-centrifuging at 30,000 g for another 10 minutes to remove residual cells.

A "plasma methylome" is the methylome determined from the plasma or serum of an animal (e.g., a human). The plasma methylome is an example of a cell-free methylome since plasma and serum include cell-free DNA. The plasma methylome is also an example of a mixed methylome since it is a mixture of DNA from different organs or tissues or cells within a body. In one embodiment, such cells are the hematopoietic cells, including, but not limited to cells of the erythroid (i.e. red cell) lineage, the myeloid lineage (e.g., neutrophils and their precursors), and the megakaryocytic lineage. In pregnancy, the plasma methylome may contain methylomic information from the fetus and the mother. In a patient with cancer, the plasma methylome may contain methylomic information from the tumor cells and other cells within the patient's body. The "cellular methylome" corresponds to the methylome determined from cells (e.g., blood cells) of the patient. The methylome of the blood cells is called the blood cell methylome (or blood methylome). Techniques for determining a methylome are further described in PCT Patent Application No. WO2014/043763 entitled "Non-Invasive Determination Of Methylome Of Fetus Or Tumor From Plasma," the disclosure of which is incorporated by reference in its entirety for all purposes.

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies DNA molecules depending of their methylation status, e.g. bisulfate conversion, or methylation-sensitive restriction enzyme. A read can be a sequence read. A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes (e.g., in hybridization arrays or capture probes, or amplification techniques, such as the polymerase chain reaction (PCR) or linear amplification using a single primer or isothermal amplification).

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by the Pacific Biosciences single molecule real time analysis (Flusberg et al. Nat Methods 2010; 7: 461-465)).

A "methylation profile" (also called methylation status) includes information related to DNA methylation for a region. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" correspond to tissues used to determine tissue-specific methylation levels. Multiple samples of a same tissue type from different individuals may be used to determine a tissue-specific methylation level for that tissue type. The same tissue from the same individual at different times may exhibit differences due to physiology (e.g. pregnancy) or pathology (e.g. cancer or anemia or infection or mutation). The same tissue type from different individuals may exhibit differences due to physiology (e.g. age, sex) or pathology (e.g. cancer or anemia or infection or mutation).

The term "level of a disorder" also referred to as "classification of a disorder" can refer to a classification of whether the disorder exists, a type of the disorder, a stage of a disorder, and/or other measure of a severity of a disorder. The level could be a number or other characters. The level could be zero. The level of disorder can be used in various ways. For example, screening can check if the disorder is present in someone who is not known previously to have the disorder. Assessment can investigate someone who has been diagnosed with the disorder to monitor the progress of the disorder over time, study the effectiveness of therapies or to determine the prognosis. In one embodiment, the prognosis can be expressed as the chance of a patient dying of the disorder, or the chance of the disorder progressing after a specific duration or time. Detection can mean 'screening' or can mean checking if someone, with suggestive features of the disorder (e.g. symptoms or other positive tests), has the disorder.

Anemia refers to a condition in which the number of red blood cells or their oxygen-carrying capacity is insufficient to meet physiologic needs, which may vary by age, sex, altitude, smoking, and pregnancy status. According to the recommendations of the World Health Organization (WHO), anemia can be diagnosed when the hemoglobin concentration is less than 130 g/L for men and less than 110 g/L for women. The term "degree of anemia" can be reflected by the hemoglobin concentration in the subject. A lower hemoglobin level indicates a more severe degree of anemia. According to the recommendation of WHO, severe anemia refers to hemoglobin concentration of <80 g/L for men and <70 g/L for women, moderate anemia refers to hemoglobin concentration of 80-109 g/L for men and 70-99 g/L for women, and mild anemia refers to hemoglobin concentration of 110-129 g/L for men and 100-109 g/L for women.

A "separation value" corresponds to a difference or a ratio involving two values, e.g., two fractional contributions or two methylation levels. The separation value could be a simple difference or ratio. The separation value can include other factors, e.g., multiplicative factors. As other examples, a difference or ratio of functions of the values can be used, e.g., a difference or ratio of the natural logarithms (ln) of the two values. A separation value can include a difference and a ratio.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. A threshold value may be a value above or below which a particular classification applies. Either of these terms can be used in either of these contexts.

DETAILED DESCRIPTION

In some embodiments, the contribution of cell-free DNA (also called circulating DNA) from erythroblasts is quantified using one or more methylation signatures (e.g., one signature per marker) specific to erythroblasts relative to cell-free DNA from other tissue. A marker (e.g., a differentially methylated region, DMR) can include one site or a group of sites contributing to a same signature.

The contribution of the cell-free DNA from erythroblasts can be used to determine a level of a hematological disorder, such as anemia. For example, embodiments can be used to assess anemia in a fetus, a neonate or a child. In the context of anemia, embodiments can be used to investigate someone who is suspected to have anemia, or has been diagnosed with anemia: (i) to elucidate the causes of the anemia; (ii) to monitor the progress of the clinical status over time, (iii) to study the effectiveness of therapies, or (iv) to determine the prognosis. Accordingly, embodiments have identified erythroid DNA as a hitherto unrecognized major component of the circulating DNA pool and as a noninvasive biomarker for differential diagnosis and monitoring of anemia, as well as other hematological disorders.

I. INTRODUCTION

Plasma DNA is an increasingly pursued analyte for molecular diagnostics. There are ongoing research studies on its clinical applications especially in noninvasive prenatal testing (1-7) and oncology (8-12). Despite a wide variety of clinical applications, the tissue origin of circulating DNA is not completely understood.

It has been shown that circulating DNA is predominantly released from hematopoietic cells using sex-mismatched bone marrow transplantation as model systems (13, 14). Kun et al. recently demonstrated that a significant proportion of plasma DNA has methylation signatures of neutrophils and lymphocytes (15). However, there is currently no information regarding whether DNA of erythroid origin (erythroblasts) might also be detectable in plasma.

Red blood cells (RBCs) are the largest population of hematopoietic cells in blood. The concentration of red blood cells (RBCs) is approximately $5 \times 10^{12}$ per liter of blood. Given the life span of each RBC is around 120 days, the body needs to produce $2 \times 10^{11}$ RBC per day or $9.7 \times 10^{9}$ RBC per hour. Mature RBCs in humans do not have a nucleus.

It is during the enucleation step that erythroblasts lose their nuclei and mature into reticulocytes in the bone marrow (16). The process of enucleation is a complex multistep process involving tightly regulated actions of cell-signaling and cytoskeletal actions. The nuclear material of the erythroblasts is phagocytosed and degraded by the marrow macrophages in the erythroblastic islands, e.g., in bone marrow (17). We postulate that some of the degraded DNA material of the erythroid lineage from the bone marrow would be released into the circulation.

Embodiments can identify methylation signatures of DNA from cells of erythroid origin and use such signatures to determine if erythroid DNA is detectable in human plasma. High-resolution reference methylomes of different tissues and hematopoietic cell types have become publicly available through collaborative projects including the BLUEPRINT Project (18, 19) and the Roadmap Epigenomics Project (20). We and others have previously demonstrated that it is possible to trace the origin of plasma DNA through analysis of the tissue-related methylation signatures (15, 21, 22). Further details of such an analysis to determine a contribution of certain tissue to a cell-free mixture (e.g., plasma) can be found in PCT Patent Application No. WO 2016/008451 entitled "Methylation Pattern Analysis Of Tissues In A DNA Mixture," the disclosure of which is incorporated by reference in its entirety for all purposes.

To validate our hypothesis and demonstrate the presence of erythroid DNA in plasma, we identified erythroblast-specific differentially methylated regions (DMRs) through analysis of the methylation profiles of erythroblasts and other tissue types. Based on the findings, we developed digital polymerase chain reaction (PCR) assays targeting the erythroblast-specific DMRs to enable quantitative analysis of erythroid DNA in biological samples. Specifically, using high-resolution methylation profiles of erythroblasts and other tissue types, three genomic loci were found to be hypomethylated in erythroblasts but hypermethylated in other cell types. Digital PCR assays were developed for measuring erythroid DNA using the differentially methylated region for each locus.

We applied these digital PCR assays to study the plasma samples of healthy subjects and patients suffering from different types of anemia. We also explored the potential clinical utility of the assays in anemia evaluation. Although examples use PCR assays, other assays may be used, such as sequencing.

In subjects with anemia of different etiologies, we show that quantitative analysis of circulating erythroid DNA (e.g., using a methylation marker) reflects the erythropoietic activity in the bone marrow. For patients with reduced erythropoietic activity, as exemplified by aplastic anemia, the percentage of circulating erythroid DNA was decreased. For patients with increased but ineffective erythropoiesis, as exemplified by β-thalassemia major, the percentage was increased. In addition, the plasma level of erythroid DNA was found to correlate with treatment response in aplastic anemia and iron deficiency anemia. Plasma DNA analysis using digital PCR assays targeting the other two differentially methylated regions showed similar findings.

II. DIFFERENTIALLY METHYLATED REGIONS (DMR) OF ERYTHROBLASTS

We hypothesize that the erythroblast enucleation process or other processes involved in the maturation of RBC would contribute significantly to the pool of circulating cell-free DNA. To determine the contribution of circulating DNA from erythroblasts, we identified the differentially methylated regions (DMR) in the DNA of erythroblasts by comparing the DNA methylation profiles of erythroblasts to other tissues and blood cells. We studied the methylation profiles of erythroblasts and other blood cells (neutrophils, B-lymphocytes and T-lymphocytes) and tissues (liver, lung, colon, small intestines, pancreas, adrenal gland, esophagus, heart, brain and placenta) from the BLUEPRINT Project and the Roadmap Epigenomics Project and methylomes generated by our group (18-20, 23).

In a simple example, one or more DMRs can be used directly to determine a contribution of circulating DNA from erythroblasts, e.g., by determining a percentage of DNA fragments that are methylated (for DMRs that are hypermethylated) or unmethylated (for DMRs that are hypomethylated). The percentage can be used directly or modified (e.g., multiplied by a scaling factor). Other embodiments can perform more complicated procedures, e.g., solving a linear system of equations. As described in PCT Patent Application No. WO 2016/008451, methylation levels at N genomic sites can be used to compute a contribution from M tissues, where M is less than or equal to N. The methylation levels at each site can be computed for each tissue. The linear system of equations $Ax=b$ can be solved, where b is a vector of the measured methylation densities at the N sites, x is a vector of the contribution from the M tissues, and A is a matrix of M rows and N columns, with each row providing the methylation densities at the N tissues at the particular site of that row. If M is less than N, then a least squares optimization can be performed. The matrix A of dimensions N by M can be formed of tissue-specific methylation levels of reference tissues, as obtained from the sources above.

A. Identification of DMR

To identify a differentially methylated region (DMR), tissue of a particular type/lineage (e.g., erythroblasts) can be isolated and then analyzed, e.g., using methylation-aware sequencing, as is described herein. The methylation densities at a site across tissues types (e.g., just two types of erythroblasts and other) can be analyzed to determine whether a sufficient different exists, so as to identify the site for use in a DMR.

In some embodiments, one or more of following criteria can be used to identify a methylation marker for erythroblasts. (1) A CpG site is hypomethylated in erythroblasts if the methylation density of the CpG site is less than 20% in the erythroblasts and over 80% in other blood cells and tissues, and vice versa. (2) To be a DMR, the region can be required to include multiple CpG sites (e.g., 3, 4, 5, or more) that are hypomethylated. Thus, a stretch of multiple CpG sites within the DMR can be chosen to be analyzed by the assay so as to improve the signal-to-noise ratio and specificity of the DMR. (3) The DMR can be chosen to be of a size representative of a DNA molecule in the cell-free mixture. In plasma, there are mainly short DNA fragments with a majority being shorter than 200 bp (1, 24, 25). For embodiments that determine the presence of erythroid DNA molecules in plasma, the DMR can be defined within a representative size of a plasma DNA molecule (i.e. 166 bp) (1). Variations of such criteria can be used in combination with these three criteria, e.g., different thresholds other than 20% and 80% can be used for identifying a CpG site as hypomethylated. As discussed later, some results use selected CpG sites within three erythroblast-specific DMRs that are hypomethylated in erythroblasts.

With the above-defined criteria, we identified three erythroblast-specific DMRs across the whole genome. One DMR was within the intronic region of the ferrochelatase (FECH) gene on chromosome 18. In this region, the differences in methylation densities between erythroblasts and other cell types are the greatest among the three DMRs identified. The FECH gene encodes ferrochelatase, which is an enzyme responsible for the final step of heme biosynthesis (26). As shown in FIG. 1, the four selected CpG sites within the erythroblast-specific DMR were all hypomethylated in erythroblasts, but hypermethylated in other blood cells and tissues.

FIG. 1 shows methylation densities of the CpG sites within the promoter of the ferrochelatase (FECH) gene according to embodiments of the present invention. The FECH gene is located on chromosome 18 and the genomic coordinates of the CpG sites are shown on the X-axis. As shown, the methylation densities of the CpG sites are within the intronic region of the FECH gene. The four CpG sites located within the region 110 bounded by the two vertical dotted lines were all hypomethylated in the erythroblasts but hypermethylated in other tissues or cell types. For illustration purpose, individual results for lung, heart, small intestines, colon, thymus, stomach, adrenal glands, esophagus, bladder, brain, ovary and pancreas are not shown. Their mean values are represented by "Other tissues."

As the CpG sites located within this region are hypomethylated, sequences that are unmethylated for all the four CpG sites within the two dotted lines in FIG. 1 would be enriched for DNA derived from the erythroblasts. Thus, the amount of hypomethylated sequences in a DNA sample would reflect the amount of DNA derived from the erythroblasts.

An assay was developed to detect DNA that are methylated or unmethylated at the identified CpG sites. The higher the number of CpGs within a plasma DNA molecule, the assay would be more specific. Most plasma DNA molecules are less than 200 bp, on average 166 bp. Thus, the CpG sites may all be within 166 bp of each other, but can be within 150, 140, 130, 120, 110, or 100 bp of each other. In other embodiments, just pairs of CpG sites can be within such distances of each other.

In other embodiments, a CpG site can be defined as hypomethylated in the erythroblasts if the methylation density of the CpG site is less than 10% (or other threshold) in the erythroblasts and over 90% (or other threshold) in all other tissues and blood cells. A CpG site can be defined as hypermethylated in the erythroblasts if the methylation density of the CpG site is above 90% (or other threshold) in the erythroblasts and below 10% (or other threshold) in all other tissues and blood cells. In some implementations, a DMR can have at least two CpG sites within 100 bp, all showing differential methylation for the erythroblasts.

In one implementation of identifying a DMR, to be diagnostically useful, all the CpG sites within 100 bp (or some other length) can be required to show hypomethylation or hypermethylated in erythroblasts compared with all other tissues and blood cells. For example, the plurality of CpG sites can span 100 bp or less on a reference genome corresponding to the mammal. As another example, each CpG site can be within 100 bp of another CpG site. Thus, the CpG sites can span more than 100 bp.

In some embodiments, the one or more differentially-methylated regions may be identified in the following manner. Methylation indexes (e.g., densities) of a plurality of sites can be obtained for each of a plurality of cell lineages, including the particular hematological cell lineage and the other cell lineages e.g., as shown in FIG. 1. At each site of the plurality of sites, the methylation indexes of the plurality of cell lineages can be compared to each other. Based on the comparing, one or more sites of the plurality of sites can be identified that each have a methylation index in the particular hematological cell lineage that is below/above a first methylation threshold and methylation indexes in each of the other cell lineages that are above/below a second methylation threshold. In this manner, hypomethylated sites and/or hypermethylated sites can be identified. Examples of the first methylation threshold are 10%, 15%, or 20% for hypomethylated sites, where examples of the second methylation threshold can be 80%, 85%, or 90%. A differentially-methylated region that contains the one or more sites can then be identified, e.g., using criteria described above.

B. Detection of Methylated and Unmethylated DNA Sequences

To detect methylated and unmethylated DNA sequences at the erythroblast-specific DMRs, two digital PCR assays may be developed: one targeting the unmethylated sequences and the other targeting the methylated sequences. In other embodiments, other methods can also be used for the detection and/or quantification of methylated and unmethylated sequences of a DMR, such as methylation-aware sequencing (e.g. bisulfite sequencing or sequencing following biochemical or enzymatic processes that would differentially modify DNA based on its methylation status), real-time methylation-specific PCR, methylation-sensitive restriction enzyme analysis, and microarray analysis. Thus, other types of assays can be used, besides PCR assays.

In one example, an erythroblast DMR can be detected after bisulfite treatment. The methylation status of the CpG sites can be determined based on the detection results (e.g., PCR signals). For the FECH gene, the following primers can be used for amplifying the erythrocyte DMR after bisulfite treatment for sequencing:

```
                                              (SEQ ID NO: 1)
    5'-TTTAGTTTATAGTTGAAGAGAATTTGATGG-3'
    and
                                              (SEQ ID NO: 2)
    5'-AAACCCAACCATACAACCTCTTAAT-3'.
```

In another example, to enhance the specificity of the analysis, two forward primers that cover both the methylated and unmethylated status of the particular CpG can used. Such a set of primers used for two digital PCR assays that specifically targeted methylated and unmethylated sequences are listed below.

TABLE 1

Assay for the specific detection of unmethylated sequences.

| Primers/probe | Sequence (SEQ ID NOS: 3-6) |
|---|---|
| Forward primer-1 | 5'-TTGAAGAGAATTTGATGGTATGGGTA-3' |
| Forward primer-2 | 5'-TGAAGAGAATTTGATGGTACGGGTA-3' |
| Reverse | 5'-CTCAAATCTCTCTAATTTCCAAACACA-3' |
| Fluorescence probe | 5'-FAM-TTGTGTGGTGTAGAGAG-MGB-3' |

TABLE 2

Assay for the specific detection of methylated sequences

| Primer | Sequence (SEQ ID NOS: 3, 4, 7 and 8) |
|---|---|
| Forward | 5'-TTGAAGAGAATTTGATGGTATGGGTA-3' |
|  | 5'-TGAAGAGAATTTGATGGTACGGGTA-3' |
| Reverse | 5'-CAAATCTCTCTAATTTCCGAACACG-3' |
| Fluorescence probe | 5'-VIC-TGCGTGGCGTAGAG-MGB-3' |

The underlined nucleotides in the reverse primers and the probes were the differentially methylated cytosines at the CpG sites. The reverse primers and the probes of the unmethylated and methylated assays bind to the unmethylated and methylated sequences specifically because of the differences at the underlined nucleotides.

C. Confirmation Using Universally Methylated and Universally Unmethylated DNA

An analysis of universally methylated and universally unmethylated DNA was performed to confirm the accuracy of the two assays.

The universally methylated sequences from the CpGenome Human Methylated DNA (EMD Millipore) and the universally unmethylated sequences from the EpiTect Unmethylated Human Control DNA (Qiagen) were used to confirm the specificity of the two digital PCR assays, which were designed for the detection and quantification of methylated and unmethylated sequences at the erythroblast-specific DMR. The CpGenome Human Methylated DNA was purified from HCT116 DKO cells followed by enzymatic methylation of all CpG nucleotides using M.SssI methyltransferase. The universally methylated and universally unmethylated DNA sequences were run on the same plate as positive and negative controls. The cut-off values for positive fluorescence signals were determined with reference to the controls. The numbers of methylated and unmethylated DNA sequences in each sample was calculated using combined counts from duplicate wells followed by Poisson correction (4).

Figure 2A:
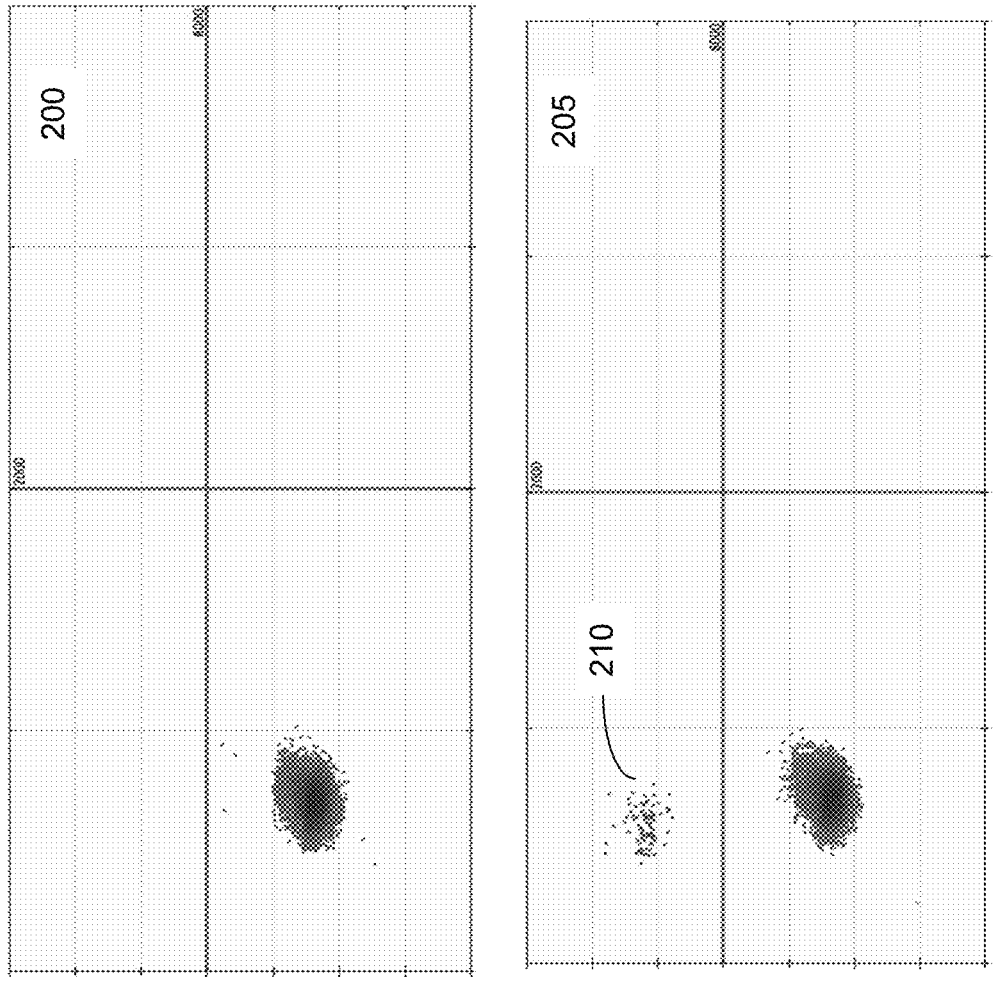
FIGS. 2A and 2B show an analysis of universally methylated and unmethylated DNA using the digital PCR assays designed for detecting methylated and unmethylated DNA according to embodiments of the present invention.
Figure 2B:
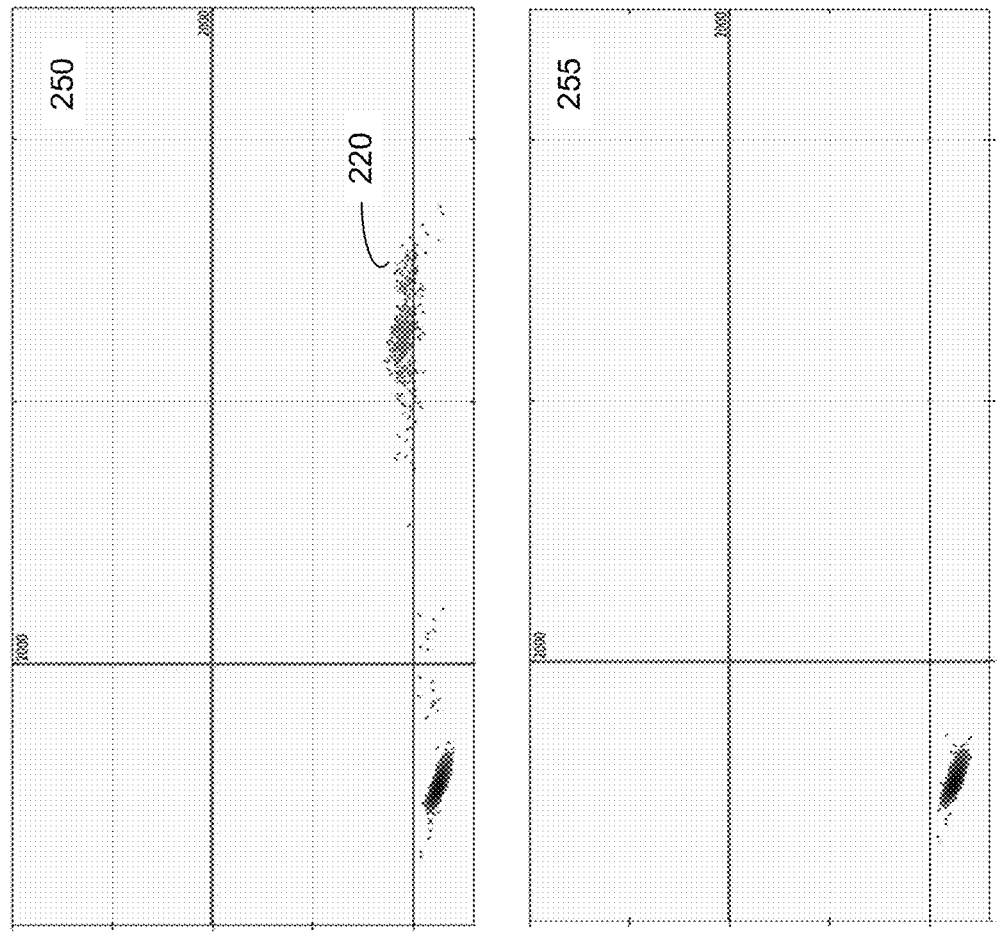

FIGS. 2A and 2B show an analysis of universally methylated and unmethylated DNA using the digital PCR assays designed for detecting methylated and unmethylated DNA according to embodiments of the present invention. The vertical axis corresponds to the intensity of the relative fluorescence signal for unmethylated sequences. The horizontal axis corresponds to the intensity of the relative fluorescence signal for methylated sequences. The data was generated using DNA that is known to be either methylated or unmethylated. These analyses are aimed to demonstrate the specificity of the assays towards methylated or unmethylated DNA.

For the analysis of universally unmethylated DNA, the amplification signal was detected using the assay for unmethylated DNA (blue dots 210 in plot 205 of FIG. 2A corresponding to the positive FAM signal), where the blue dots 210 were not detected when using the assay for methylated DNA (plot 255 of FIG. 2B). For the analysis of the universally methylated DNA, the amplification signal was detected using the assay for methylated DNA (green dots 220 in plot 250 of FIG. 2B corresponding to the positive VIC signal), where the green dots 220 were not detected using the assay for unmethylated DNA (plot 200 of FIG. 2A). The black dots in each panel represent the droplets without any amplified signal. The thick vertical and horizontal lines within each of the four panels represent the threshold fluorescence signal for positive results. These results confirmed the specificity of the two assays for methylated and unmethylated DNA at the erythroblast-specific DMR.

To further assess the analytical sensitivity of the assay based on the FECH gene-associated DMR, the samples with the unmethylated sequences were serially diluted at specific fractional concentrations (i.e., percentage of unmethylated sequences among all (unmethylated and methylated) sequences at the FECH gene-associated DMR). There were a total of 1,000 molecules per reaction. The unmethylated sequences could be detected at as low as 0.1% of the total amount of methylated and unmethylated sequences (See Table 3).

TABLE 3

Measured concentrations (percentages of unmethylated sequences) at different input concentrations of unmethylated sequences for sensitivity assessment of the assay targeting the FECH gene-associated DMR.

| Input concentration (% unmethylated sequences) | Measured concentration (% unmethylated sequences) |
|---|---|
| 10.0% | 9.83% |
| 5.0% | 5.36% |
| 2.0% | 2.85% |
| 1.0% | 0.99% |
| 0.5% | 0.33% |
| 0.1% | 0.34% |

Additionally, to assess the potential variations (e.g. from pipetting), we repeatedly measured the percentage of unmethylated sequences in an artificially mixed sample of methylated and unmethylated sequences at a specific fractional concentration (% unmethylated sequences=30%) in 20 separate reactions. We used a total of 500 methylated and unmethylated molecules for each reaction. This number is comparable to what we have observed in the total number of methylated and unmethylated molecules in our digital PCR analysis for plasma DNA samples. We observed a mean of 30.4% and a standard deviation of 1.7% for the 20 repeated measurements of the percentage of unmethylated sequences. The intra-assay coefficient of variation is calculated to be 5.7%.

III. SPECIFICITY AND SENSITIVITY OF ASSAYS FOR DIFFERENT SAMPLES

To confirm the tissue specificity of the digital PCR assays targeting the FECH gene-associated DMR for erythroid DNA, we tested the digital PCR assays in various samples having differing amounts of erythroblast cells, as measured using techniques other than these digital PCR assays. The amount of unmethylated DNA sequences detected by the digital PCR assays should reflect the amount of erythroid DNA. Similarly, the amount of methylated sequences should reflect DNA from other tissues or cell types. Therefore, we defined the percentage of erythroid DNA (E %) in a biological sample as the percentage of unmethylated sequences among all the detected (unmethylated and methylated) sequences at an erythroblast-specific DMR. Accordingly, blood samples were analyzed using the assays specific for methylated and unmethylated sequences for the DMR region to determine a correlation between the percentage of unmethylated sequences, Unmeth % (also referred to as E %), and the existence of DNA from erythroblasts. Unmeth % (E %) are examples of methylation levels.

The percentage of erythroid DNA (E %) was calculated as:

$$E\ \% = \frac{No.\ of\ unmethylated\ DNA\ sequences}{No.\ of\ methylated\ DNA\ sequences + No.\ of\ unmethylated\ DNA\ sequences}$$

Since the differences in methylation densities between erythroblasts and other cell types are the greatest for the DMR within the FECH gene, we first proceeded to E % analysis based on this marker site to prove our hypothesis. Subsequently, we analyzed the E % based on the other two erythroblast-specific DMRs in a subset of samples to validate E % results from the FECH gene-associated DMR. E % results based on the DMR within the FECH gene would be denoted by E % (FECH). Other percentages or ratios may also be used, such as the percentage of methylated sequences, or just a ratio of methylated sequences to unmethylated sequences, where either value can be in the numerator and denominator of the ratio.

Specifically, the numbers of methylated and unmethylated DNA sequences in each sample at the four CpG sites on the FECH gene from FIG. 1 were determined using digital PCR. Then, the percentage of unmethylated DNA (Unmeth %/E %) in the sample was calculated. In one embodiment, for a DNA fragment to be considered unmethylated, all of the four CpG sites are to be unmethylated.

Two scenarios are used to test the ability of the assay signals to quantify erythroblasts. One scenario is cord blood vs. adult blood, as the two types of samples vary in number of erythroblasts. And, for the other scenario, subjects with beta-thalassemia major have an appreciable number of erythroblasts in their blood.

A. Erythroblast-Enriched Samples Vs. Buffy Coat of Healthy Subjects

The number of erythroblasts in adult blood is very low. Cord blood has much higher number of erythroblasts. Thus, E % for the four CpG sites should be much higher in cord blood than for the healthy patients. Accordingly, to confirm the tissue specificity of the digital PCR assays targeting the FECH gene-associated DMR for erythroid DNA, we tested the digital PCR assays in samples including DNA extracted from 12 different normal tissue types and in erythroblast-enriched samples. We included 4 samples from different individuals for each tissue type. An erythroblast-enriched sample was prepared from umbilical cord blood for analysis.

Specifically, to confirm the relation between methylation density at the DMRs and E %, venous blood samples were collected from 21 healthy subjects and 30 pregnant women (10 in the first trimester, 10 in the second trimester and 10 in the third trimester). The blood samples were centrifuged at 3,000 g for 10 minutes to separate the plasma and the blood cells. The buffy coat was collected after the centrifugation. The plasma samples were collected and re-centrifuged at 30,000 g to remove residual blood cells.

As to the 12 different normal tissue types, we included 4 samples from different individuals for each tissue type. As shown in Table 4, the median E % (FECH) values from all the tissues DNA were low (range of median values: 0.00% to 2.63%).

TABLE 4

Table showing the median percentage of erythroid DNA (E %(FECH)) in 4 sets of 12 tissue types, with each tissue sample being obtained from a different individual.

| Tissue | Median E % |
| --- | --- |
| Liver | 0.12% |
| Lung | 1.33% |
| Esophagus | 2.63% |
| Stomach | 2.58% |
| Small intestines | 2.33% |
| Colon | 1.51% |
| Pancreas | 0.12% |
| Adrenal gland | 0.00% |
| Urinary bladder | 1.20% |
| Heart | 0.82% |
| Brain | 1.94% |
| Placenta | 0.10% |

The experimental procedures for enrichment from umbilical cord blood by flow cytometry and cell sorting and subsequent DNA extraction are described below. 1-3 mL of umbilical cord blood was collected from each of eight pregnant women following the delivery of her baby. Mononuclear cells were isolated from the cord blood samples after density gradient centrifugation using the Ficoll-Paque PLUS kit (GE Healthcare). After the collection of the mononuclear cells, $1 \times 10^8$ cells were incubated with 1 mL of the mixture of the fluorescein isothiocyanate (FITC)-conjugated anti-CD235a (Glycophorin A) and phycoerythrin (PE)-conjugated anti-CD71 antibodies (Miltenyi Biotec) in a 1:10 dilution in phosphate-buffered saline for 30 minutes in the dark at 4° C. The sorting and analysis of CD235a+CD71+ cells was then performed using the BD FACSAria Fusion Cell Sorter (BD Biosciences). As CD235a and CD71 were specifically present in erythroblasts, the CD235a+CD71+ cells would be enriched for erythroblasts (Bianchi et al. Prenatal Diagnosis 1993; 13:293-300).

As the number of cells obtained from each case was small, the cells from the eight cases were pooled for downstream analysis. The two antibodies are specific for erythroblasts and attach to the surface of erythroblasts. The two antibodies are respectively conjugated with FITC and phycoerythrin. These two substances bind to magnetic beads, and the beads can be sorted using the cell sorter. Therefore the Ab-labeled erythroblasts can be captured. Using flow cytometry and cell sorting with anti-CD71 (transferrin receptor) and anti-CD235a (glycophorin A) antibodies (see supplemental Materials and Methods), erythroblasts were enriched from 8 umbilical cord blood samples and subsequently pooled. DNA was extracted from the pooled sample.

The E % (FECH) of the DNA from the pooled cord blood samples was 67% at the four CpG sites tested in the assay for the CD235a+CD71+ cells (mostly erythroblasts). Regarding the E % (FECH) in the buffy coat DNA of 20 healthy subjects, who had undetectable numbers of erythroblasts in their peripheral blood, the median E % in the buffy coat DNA was 2.2% (interquartile range: 1.2-3.1%). The observation of low proportions of erythroblast-specific unmethylated sequences in the buffy coat of healthy subjects is in line with the fact that mature RBCs do not possess a nucleus. As CD235a and CD71 are cell surface markers specific for erythroblasts (Bianchi et al. Prenatal Diagnosis 1993; 13:293-300), the high E % (FECH) in the cells enriched for CD235a and CD71 shows that the assay for the unmethylated DNA at the erythroblast-specific DMR would be able to detect the erythroblast-derived DNA. Accordingly, this high E % for the erythroblast-enriched samples, together with the low E % results for the DNA from other tissue types and the buffy coat DNA of healthy subjects, shows that the digital PCR assay for unmethylated FECH sequences was specific for erythroblast-derived DNA.

B. For Patients with Beta-Thalassemia Major

In patients suffering beta-thalassemia major, the bone marrow tries to make a lot of red blood cells (RBCs). However, the production of hemoglobin is defective. As a result, many RBCs do not contain sufficient hemoglobin and contain a lot of excessive alpha globin chains. These defective RBCs would be removed from the bone marrow and will never become mature RBC. There are two types of globin chains: alpha and beta. One hemoglobin molecule requires two alpha and two beta chains. If the beta chains are not produced, the excessive alpha chains will aggregate together and functional hemoglobin cannot be formed.

In patients with beta-thalassemia major, the increased but ineffective erythropoiesis would result in a reduced production of mature RBC (Schrier et al. Current Opinion in Hematology 2002; 9:123-6). This is accompanied by compensatory extramedullary hematopoiesis and the presence of nucleated red cells in the circulation. As described below, a patient with beta-thalassemia major will have more nucleated red cells than a healthy patient. The number of nucleated RBC in the peripheral blood can be counted on blood smear and expressed as number of nucleated RBC per 100 white blood cells (WBCs).

Since patients with thalassemia major generally have higher numbers of erythroblasts in the peripheral blood than healthy individuals because of ineffective erythropoiesis (27), such patients also provide a good mechanism to test the specificity and the sensitivity of the assays. We therefore tested the sensitivity of our digital PCR assays in the buffy coat DNA of fifteen patients with β-thalassemia major. All of them had detectable numbers of erythroblasts in the peripheral blood as measured by an automated hematology analyzer (UniCel DxH 800 Coulter Cellular Analysis System, Beckman Coulter) and confirmed by manual counting.

Figure 3A:
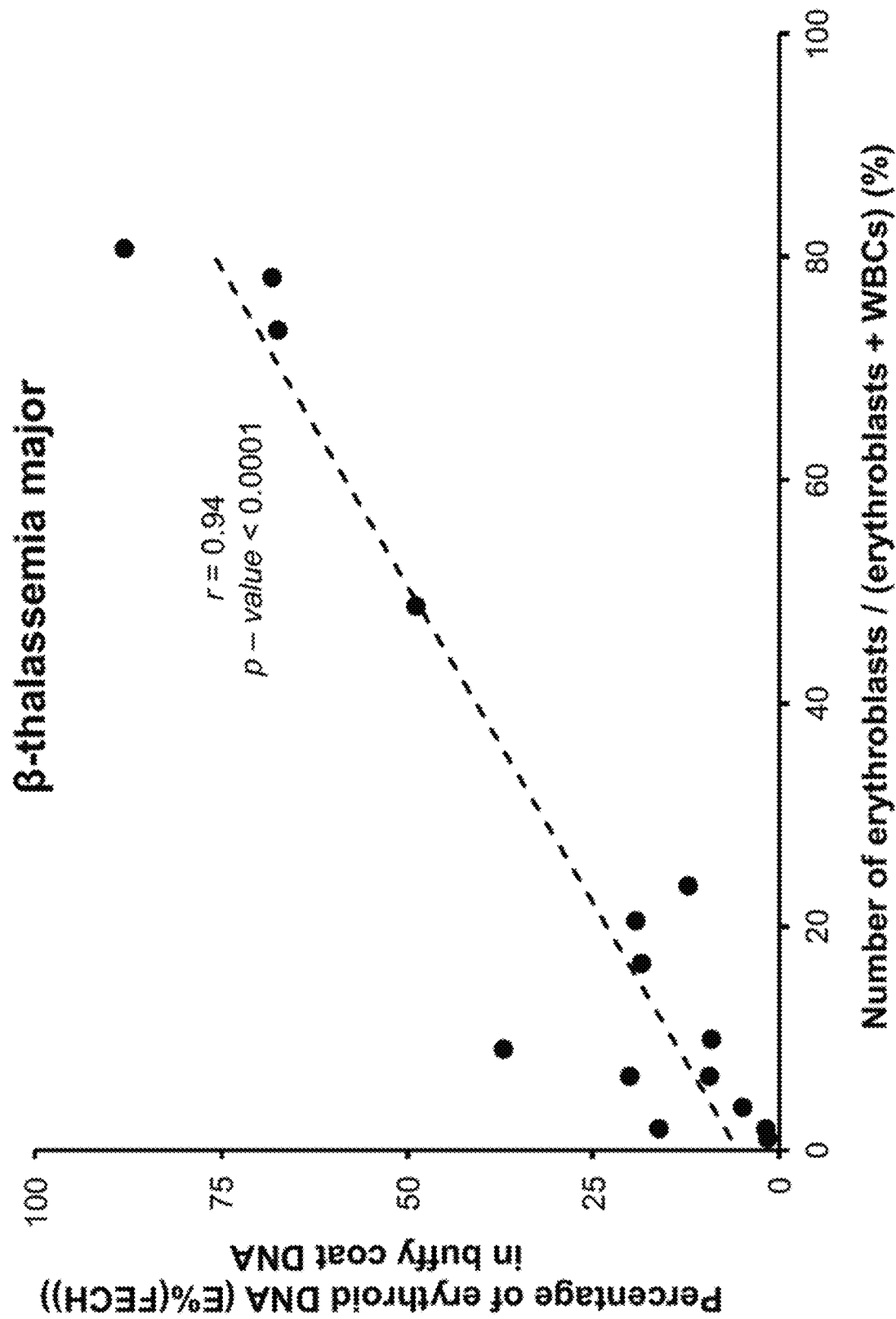
FIG. 3A is a plot showing a correlation between E % in the blood cells and the number of nucleated RBC (erythroblasts) according to embodiments of the present invention.

FIG. 3A is a plot showing a correlation between E % (FECH) in the blood cells and the number of nucleated RBC (erythroblasts) according to embodiments of the present invention. E % is measured by the digital PCR assays targeting the FECH gene-associated DMR. As shown by the axes, the plot shows the correlation between the percentage of erythroid DNA sequences (E % (FECH)) in the buffy coat DNA and the percentage of erythroblasts among all peripheral white blood cells, as measured using an automated hematology analyzer.

As shown in FIG. 3A, the E % (FECH) in the buffy coat DNA correlated well with the percentage of erythroblasts among peripheral white blood cells measured by the hematology analyzer (r=0.94, P<0.0001, Pearson correlation). The good linear relationship between E % and the erythroblast counts in the buffy coats of thalassemia patients shows that the digital PCR assays provided a good quantitative measurement of erythroid DNA content in samples, as the erythroblasts are unmethylated for the DMR and other blood cells are methylated. Therefore, the more proportion of erythroblasts in a blood sample, the higher E % would be. A purpose of this experiment is to demonstrate that the assays can be used to reflect the amount of erythroblast-derived DNA in a sample. These results further support that E % for the FECH gene reflects the proportion of DNA derived from erythroblasts.

This correlation would exist for other patients as well. But, since the number of erythroblasts can be high for patients suffering from beta-thalassemia major, their samples provide a good test for identifying such a correlation. As one can see from FIG. 3A, the patients had a broad range of E % and number of erythroblasts, thereby providing a good mechanism for testing the correlation.

C. Method of Determining Amount of Cellular DNA of Particular Cell Lineage

In some embodiments, an amount of unmethylated or methylated DNA fragments in a cell-free mixture (e.g., a plasma or serum sample) can be used to determine a number of cells (or other amount of DNA) of a particular cell lineage when the amount is counted at one or more DMRs that are specific to the particular cell lineage. As shown in FIG. 3A, the percentage of DNA fragments unmethylated at the FECH DMR correlates with the number of erythroblasts in the blood sample. An absolute concentration could also be used. For a hypermethylated DMR, the amount (e.g., a percentage or absolute concentration) of methylated DNA fragments can be used. Various cell lineages can be used, as is described herein.

To determine the number of number of cells, a calibration function can be used. In the example of FIG. 3A, the line fit to the data points can provide the calibration function. As examples, the calibration function can be stored by its functional parameters (e.g., slope and y-intercept for a line, or more parameters for other functions), or stored by a set of data points from which a curve fit can be obtained. The data points (e.g., called calibration data points) can have known values for the amount of DNA of the cell lineage (e.g., the number of cells), as can be determined via another technique, as the number of erythroblasts was determined.

Accordingly, a method can determine an amount of DNA from a particular cell lineage in a blood sample. A number of methylated or unmethylated sequences of one or more DMRs can be determined from an assay, as is described herein. A methylation level can be determined and compared to a calibration value of a calibration function. For example, the methylation level can be compared to a line (or other calibration function) to determine the intersection of the function with that methylation level, and thus the corresponding amount of DNA (e.g., the value on the horizontal axis of FIG. 3A). In other embodiments, the methylation level can be compared to individual calibration data points, e.g., which have a methylation level that is close to the measured methylation level of a sample.

Figure 3B:
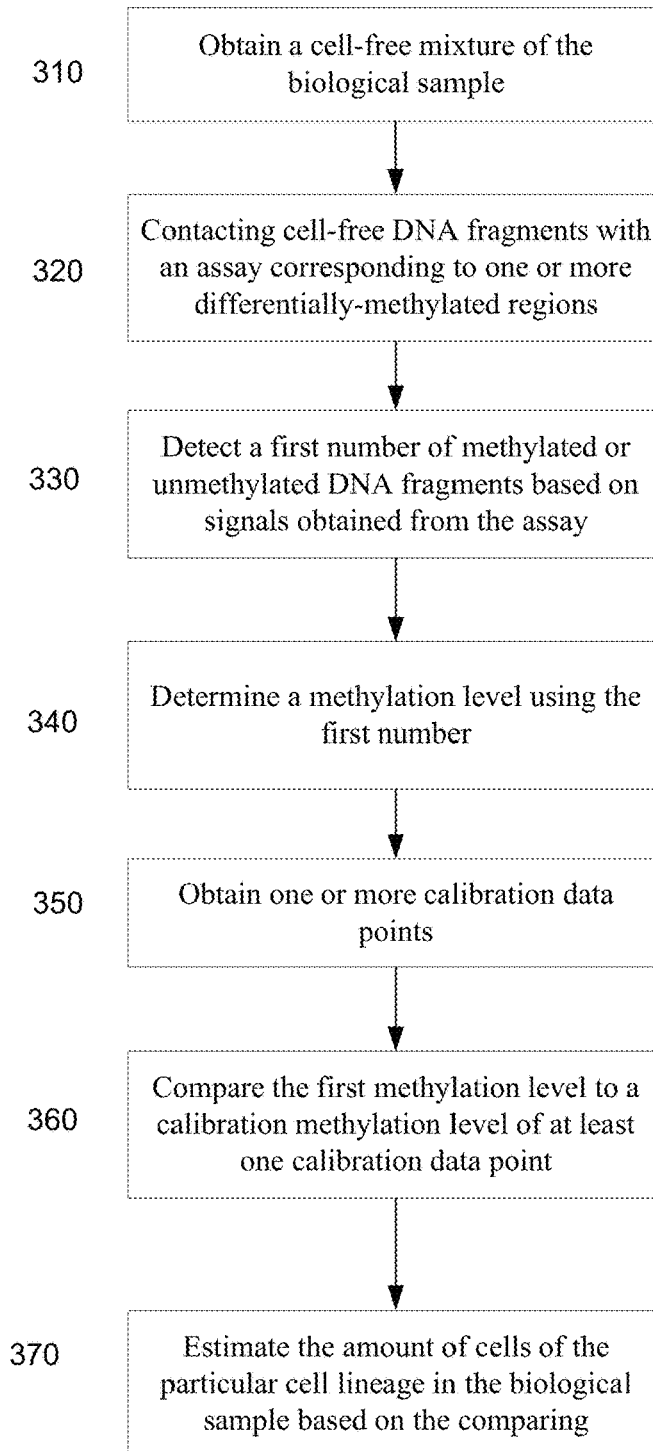
FIG. 3B is a flowchart illustrating a method 300 for determining an amount of cells of a particular cell lineage in a biological sample by analyzing cell-free DNA according to embodiments of the present invention.
Figure 27:
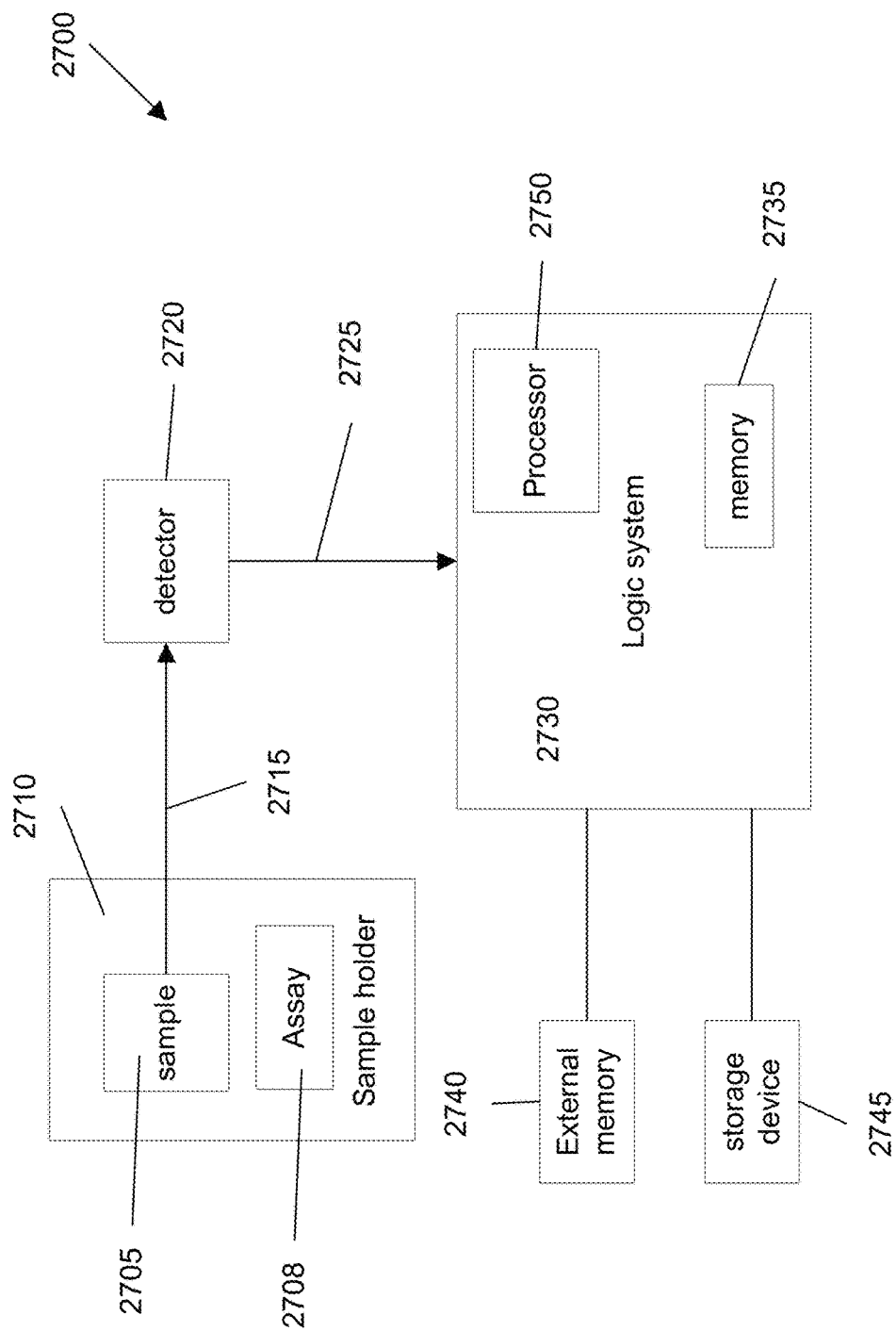
FIG. 27 illustrates a system 2700 according to an embodiment of the present invention.

FIG. 3B is a flowchart illustrating a method 300 for determining an amount of cells of a particular cell lineage in a biological sample by analyzing cell-free DNA according to embodiments of the present invention. Method 300 may use measurements like those shown in FIG. 3A. Parts of method 300 may be performed manually and other parts may be performed by a computer system. In one embodiment, a system may perform all steps. For instance, a system can includes robotic elements (e.g., to obtain a sample and perform an assay), a detection system for detecting signals from an assay, and a computer system for analyzing the signals. Instructions for controlling such a system may be stored in one or more computer readable media, such as configuration logic of a field programmable gate array (FPGA), flash memory, and/or a hard drive. FIG. 27 shows such a system.

At block 310, a cell-free mixture of the biological sample is obtained. The biological sample may be a blood sample, but could also be other samples that include cell-free DNA, as are described herein. Examples of a cell-free mixture include plasma or serum. The cell-free mixture can include cell-free DNA from a plurality of cell lineages.

At block 320, DNA fragments in the cell-free mixture are contacted with an assay corresponding to one or more differentially-methylated regions. Each of the one or more differentially-methylated regions is specific to a particular cell lineage (e.g., a particular hematological cell lineage, such as erythroblasts) by being hypomethylated or hypermethylated relative to other cell lineages.

In various embodiments, the assay can involve PCR or sequencing. Contacting the DNA fragments can involve a flow cell, droplets, beads, or other mechanisms to provide an interaction of the assay with the DNA fragments. Examples for such an assay include whole-genome bisulfite sequencing, targeted bisulfite sequencing (by hybridization capture or amplicon-sequencing), other methylation-ware sequencing (e.g. single molecule real-time (SMRT) DNA sequencing by Pacific Biosciences), real-time methylation-specific PCR, and digital PCR. Further examples of assays usable for method 300 are described herein, e.g., in section XII. Although the example FIG. 3A is for erythroblasts, other cell lineages, including other hematological cell lineages, may be used.

At block 330, a first number of methylated or unmethylated DNA fragments is detected in the cell-free mixture at the one or more differentially-methylated regions based on signals obtained from the assay. The assays can provide various signals, such as light or electrical signals. The signals can provide a specific signal per DNA fragment, or an aggregate signal indicating a total number of DNA fragments with the methylation signature (e.g., as in real-time PCR).

In one embodiment, sequencing can be used to obtain a sequence read for a DNA fragment, and the DNA fragment can be aligned to a reference genome. If the DNA fragment aligns to one of the DMRs, then a counter can be incremented. Given that the signal is from a particular methylated of unmethylated assay, the DNA fragment can be assumed to have that methylation signature. In another embodiment, a read from PCR (e.g., a light signal from a positive well) can be used to increment such a counter.

At block 340, a first methylation level is determined using the first number. The first methylation level can be normalized or be an absolute concentration, e.g., per volume of the biological sample. An example of an absolute concentration is provided in FIG. 25.

For a normalized value, a methylation level can be determined using the first number and a total number of DNA fragments in the cell-free mixture at the one or more differentially-methylated regions. As described above, the methylation level can be a percentage of unmethylated DNA fragments. In other embodiments, the percentage can be of methylated DNA fragments, which would have an inverse relationship relative to the above examples for the erythroblasts. In various implementations, the methylation level can be determined using a percentage across all sites in the DMR, by an average of an individual percentage at each site, or a weighted average at each site.

At block 350, one or more calibration data points are obtained. Each calibration data point can specify (1) an amount of cells of the particular hematological cell lineage and (2) a calibration methylation level. The one or more calibration data points are determined from a plurality of calibration samples.

The amount of cells can be specified as a particular amount (e.g., a number or a concentration) or a range of amounts. The calibration data points can be determined from calibration samples with known amounts of cells, which may be measured via various techniques described herein. At least some of the calibration samples would have a different amount of cells, but some calibration samples may have a same amount of cells.

In various embodiments, one or more calibration points may be defined as one discrete point, a set of discrete points, as a function, as one discrete point and a function, or any other combination of discrete or continuous sets of values. As an example, a calibration data point could be determined from one calibration methylation level for a sample with a particular amount of cells of the particular lineage.

In one embodiment, measured values of a same methylation level from multiple samples at the same amount of cells could be combined to determine a calibration data point for a particular amount of cells. For example, an average of methylation levels may be obtained from the methylation data of samples at the same amount of cells to determine a particular calibration data point (or provide a range that corresponds to the calibration data point). In another embodiment, multiple data points with the same calibration methylation level can be used to determine an average amount of cells.

In one implementation, the methylation levels are measured for many calibration samples. A calibration value of the methylation level is determined for each calibration sample, where the methylation level may be plotted against the known amount of cells of the samples (e.g., as in FIG. 3A). A function may then be fit to the data points of the plot, where the functional fit defines the calibration data points to be used in determining the amount of cells for a new sample.

At block 360, the first methylation level is compared to a calibration methylation level of at least one calibration data point. The comparison can be performed in a variety of ways. For example, the comparison can be whether the first methylation level is higher or lower than the calibration methylation level. The comparison can involve comparing to a calibration curve (composed of the calibration data points), and thus the comparison can identify the point on the curve having the first methylation level. For example, a calculated value X of the first methylation level can be used as input into a function F(X), where F is the calibration function (curve). The output of F(X) is the amount of cells. An error range can be provided, which may be different for each X value, thereby providing a range of values as an output of F(X).

At block 370, the amount of cells of the particular cell lineage in the biological sample is estimated based on the comparing. In one embodiment, one can determine if the first methylation level is above or below a threshold calibration methylation level, and thereby determine if the amount of cells of the instant sample is above or below the amount of cells corresponding to the threshold calibration methylation level. For example, if the calculated first methylation level $X_1$ for the biological is above a calibration methylation level $X_C$ then the amount of cells $N_1$ of the biological sample can be determined as being above the amount of cells $N_C$ corresponding to $X_C$. This relationship of above and below can depend on how the parameter is defined. In such an embodiment, only one calibration data point may be needed.

In another embodiment, the comparison is accomplished by inputting the first methylation level into a calibration function. The calibration function can effectively compare the first methylation level to calibration methylation levels by identifying the point on a curve corresponding to the first methylation level. The estimated amount of cells is then provided as the output value of the calibration function.

IV. ORIGIN OF CELL-FREE DNA FROM ERYTHROBLASTS IN PLASMA

Using the established relationship between Unmeth % and erythroblast-derived DNA, Unmeth % of plasma can be used to quantify the erythroblast-derived DNA in plasma. The Unmeth % in plasma was determined using the above assays. A difference in Unmeth % in the buffy coat and plasma is seen. The analysis shows that the cell-free erythroblast DNA in plasma is from erythropoiesis in the bone marrow, and not derived from erythroblast that are in the blood stream.

After confirming that the Unmeth % determined by the two digital PCR assays accurately reflects the amount of erythroblast-derived DNA in a sample, we proceeded to compare the proportion of erythroblast-derived DNA in the buffy coat and plasma of healthy control subjects and pregnant women.

Figure 4:
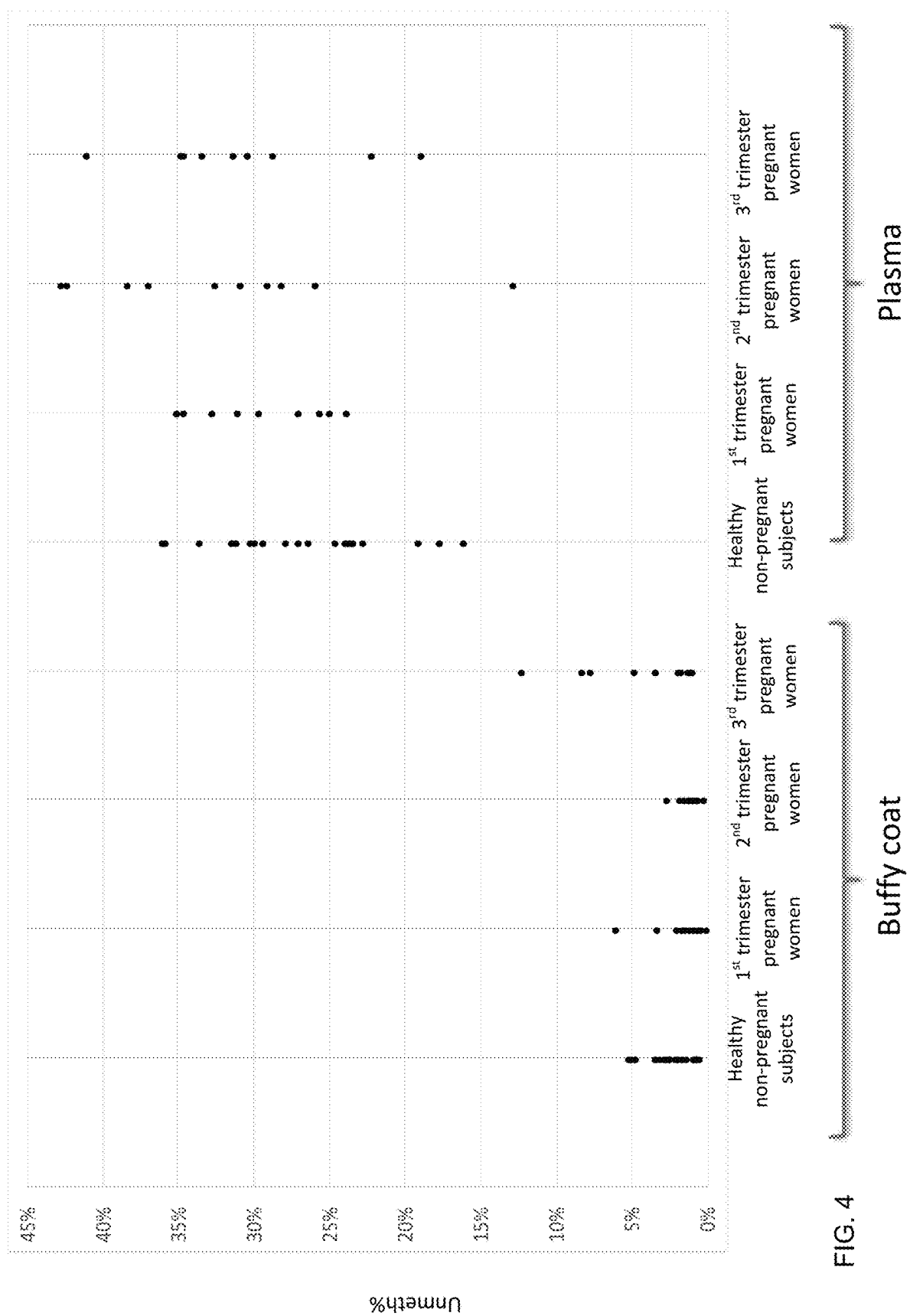
FIG. 4 shows the Unmeth % in the buffy coat and plasma of healthy non-pregnant subjects and pregnant women in different trimesters according to embodiments of the present invention.

FIG. 4 shows the Unmeth % in the buffy coat and plasma of healthy non-pregnant subjects and pregnant women in different trimesters according to embodiments of the present invention. The plasma samples had significantly higher Unmeth % compared with the buffy coat for each group of subjects (P<0.01, Wilcoxon sign-rank test for each paired comparison between plasma and buffy coat).

The results of FIG. 4 show that the amount of erythroblast-derived DNA is low in blood cells, as is expected since the number of nucleated RBCs is low. A surprising result is that the amount of erythroblast-derived DNA in plasma is high. If the erythroblast-derived DNA in plasma was derived from blood cells, one would expect the two amounts to be similar. Thus, this data shows that the origin of erythroblast-derived DNA in plasma is from erythropoiesis in the bone marrow.

Figure 5:
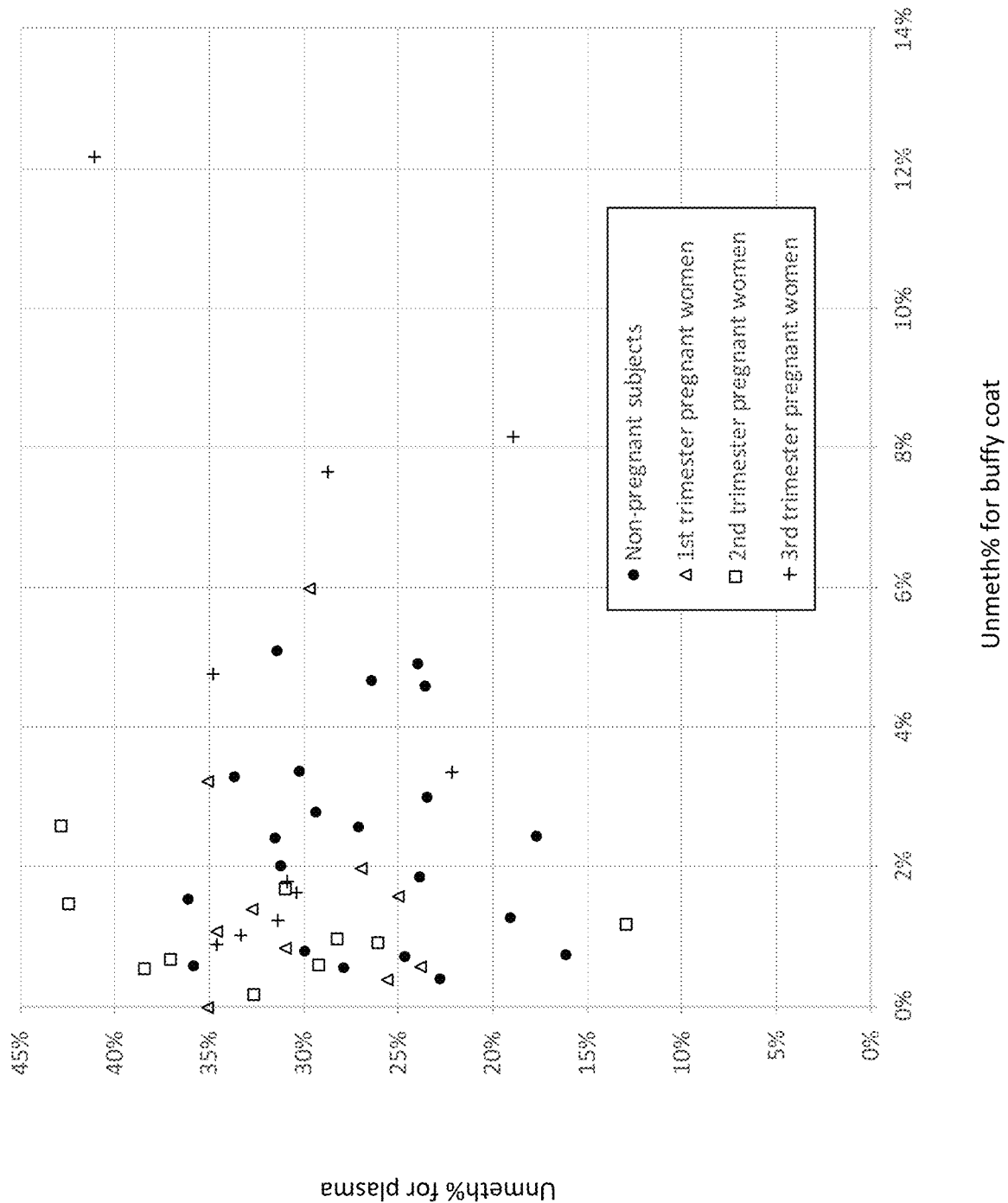
FIG. 5 is a plot showing a lack of correlation between the Unmeth % in buffy coat and plasma.

FIG. 5 is a plot showing a lack of correlation between the Unmeth % in buffy coat and plasma. No significant correlation was observed between the Unmeth % for buffy coat and plasma DNA ($R^2$=0.002, P=0.99, Pearson correlation). The lack of correlation can be seen for all of the subjects, including non-pregnant subjects, $1^{st}$ trimester pregnant women, $2^{nd}$ trimester pregnant women, and $3^{rd}$ trimester pregnant women. As with the results in FIG. 4, this is surprising as one would expect the two to be correlated if the origin of erythroblast-derived DNA was from blood cells in the blood stream.

The observations that plasma DNA has much higher Unmeth % than buffy coat and the lack of correlation between the Unmeth % of plasma and buffy coat suggests that the circulating cell-free DNA carrying the erythroblast methylation signature was likely to be derived from the bone marrow during the process of erythropoiesis, rather than derived from the circulating blood cells. Accordingly, the cell-free plasma DNA with the erythroblast methylation signature is generated in the bone marrow, as opposed to being generated from nucleated RBCs in the blood stream because the number of nucleated RBCs in the blood stream is very low in healthy subjects and pregnant women. And, since the contribution from white blood cells (WBCs) to the erythroblast methylation signature is very low, this contribution provides no measureable dependence on the cell-free plasma DNA with the erythroblast methylation signature.

V. METHYLATION LEVEL AS MEASUREMENT OF ACTIVITY OF ERYTHROPOIESIS

Based on the above observations, we determined that Unmeth % at an erythroblast DMR would reflect the activity of erythropoiesis in the bone marrow. A high Unmeth % would indicate high activity of erythropoiesis. In other words, the analysis of erythroblast DNA in plasma/serum would serve as a liquid biopsy of the bone marrow. This analysis would be particularly useful for the investigation of anemia, e.g., to determine if the anemia is due to the reduced erythropoiesis (e.g. aplastic anemia), defective erythropoiesis (e.g. failure in the production of matured RBC in thalassemia), or increased consumption of RBC (e.g. blood loss and hemolytic anemia). To this end, we recruited 35 healthy subjects and 75 anemic patients with different etiologies. Peripheral blood samples collection and processing, plasma and buffy coat DNA extraction, and bisulfite conversion of DNA were performed. Further details on methods are described in section XII.

A. Measurement of Cell-Free Erythroid DNA in the Plasma of Healthy Subjects

After confirming the specificity of our assays, we used these assays to analyze the plasma of healthy subjects. We analyzed the E % (FECH) in the plasma of 35 healthy subjects, including the same group of 20 subjects who also provided the buffy coat samples. The median E % (FECH) of plasma DNA was 30.1% (interquartile range: 23.8-34.8%). This suggested that erythroid DNA comprised a significant proportion of the circulating DNA pool in the plasma of healthy individuals. To determine the origin of plasma erythroid DNA, we compared the corresponding E % (FECH) results in the plasma and the buffy coat of the 20 healthy subjects.

Figures 6A, 6B:
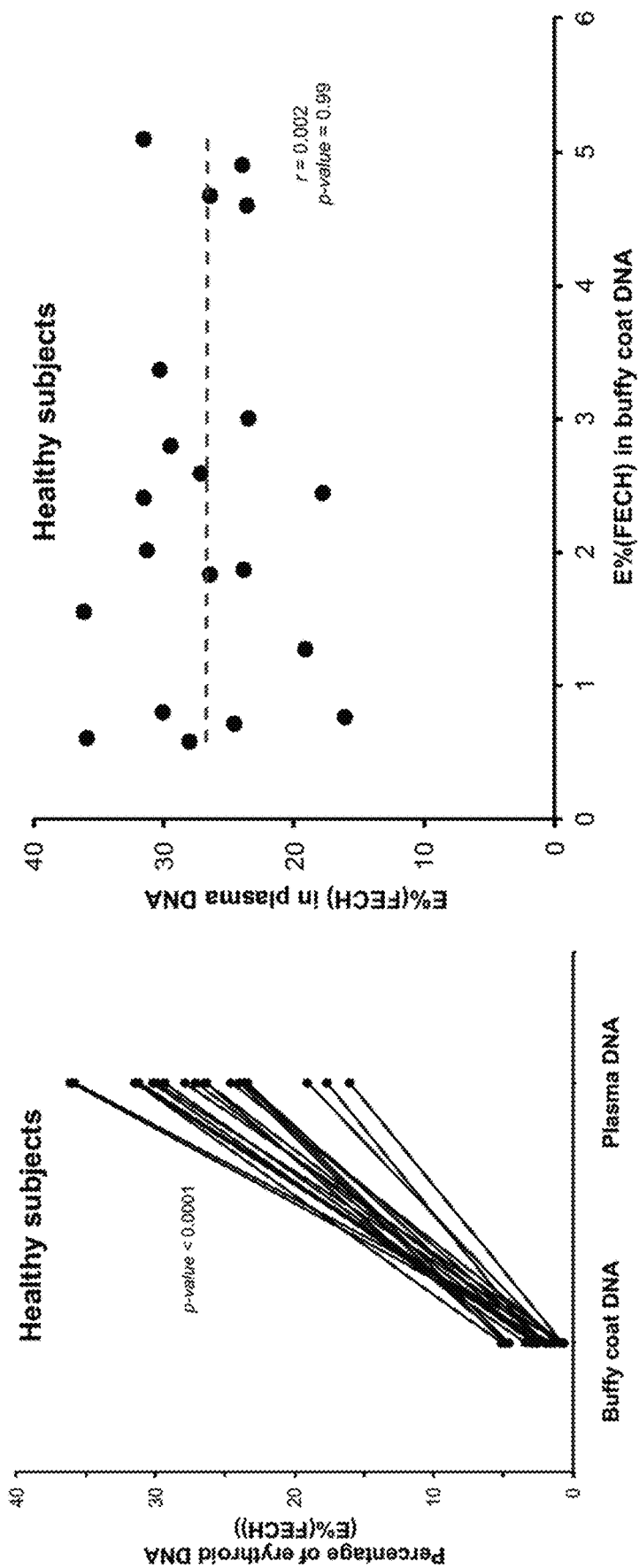
FIGS. 6A and 6B show percentages of erythroid DNA (E % (FECH)) in healthy subjects according to embodiments of the present invention. E % can be defined to be the same as Unmeth %.

FIGS. 6A and 6B show percentages of erythroid DNA (E % (FECH)) in healthy subjects. FIG. 6A shows E % in the buffy coat DNA and the plasma DNA of healthy subjects, where the value of E % is higher in plasma (cell-free portion) than in the buffy coat (cellular portion). The median E % in the plasma DNA (median: 26.7%, interquartile range: 23.7-30.4%) was significantly higher than that in the paired buffy coat DNA (median: 2.2%, interquartile range: 1.2-3.1%) (P<0.0001, Wilcoxon signed rank test).

FIG. 6B shows the lack of correlation between E % in the buffy coat DNA and in the plasma DNA of corresponding healthy subjects. There was a lack of correlation between the paired E % (FECH) results in the plasma DNA and in the buffy coat DNA (r=0.002, P=0.99, Pearson correlation). Both findings in FIGS. 6A and 6B show that circulating erythroid DNA was unlikely to have predominantly originated from the circulating erythroblasts in the peripheral blood.

Figure 7:
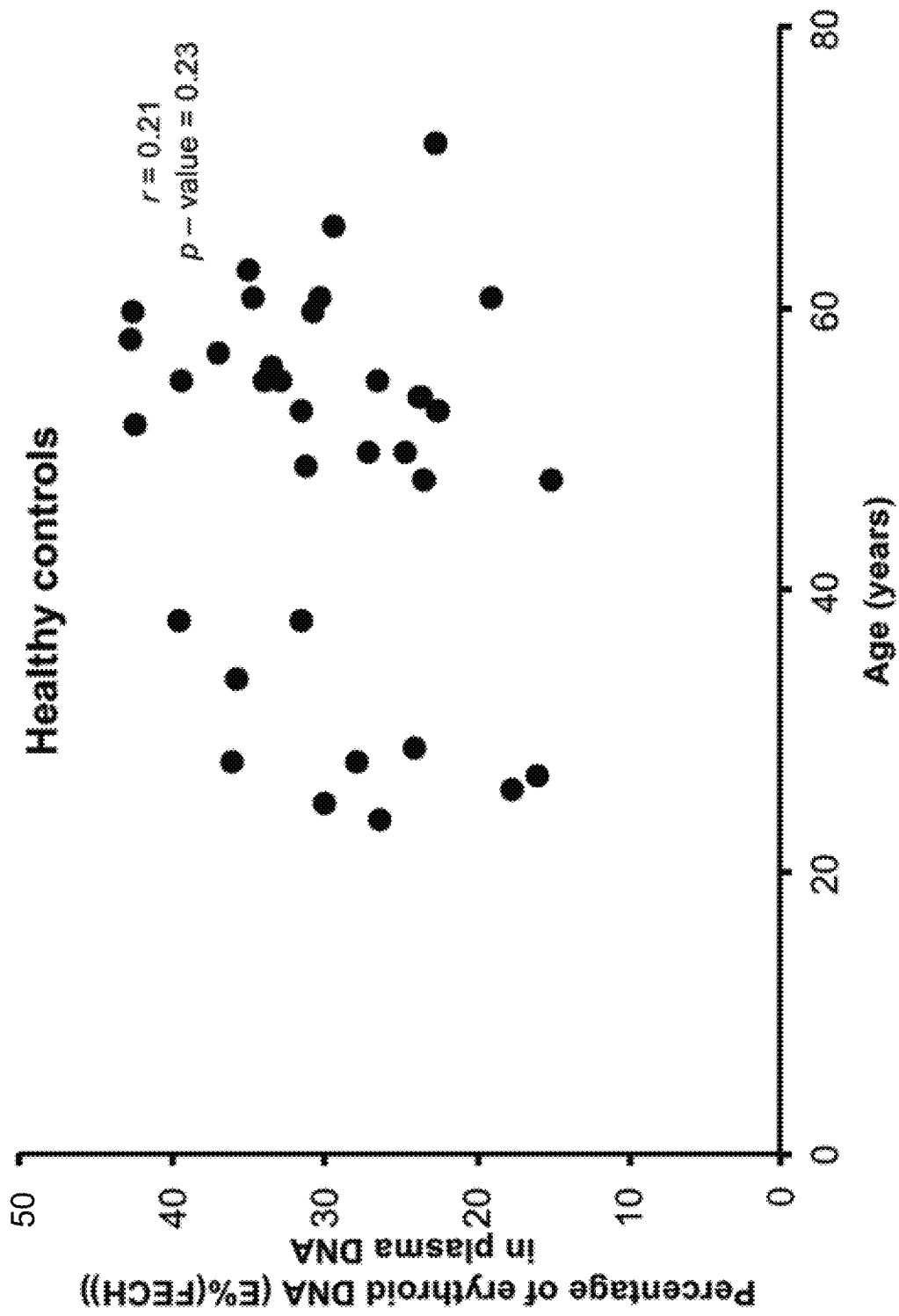
FIG. 7 shows the lack of correlation between the E % (FECH) results in the plasma DNA and age of healthy subjects.

FIG. 7 shows the lack of correlation between the E % (FECH) results in the plasma DNA and age of healthy subjects. The plot shows that the E % (FECH) results are not correlated with the age of the subjects (r=0.21, p=0.23, Pearson correlation).

B. Discrimination Between Beta-Thalassemia Major and Aplastic Anemia Patients

After determining that erythroid DNA in plasma was not predominantly released from intact erythroblasts in the circulation, we proposed that these DNA molecules were more likely released during erythropoiesis from the bone marrow. We reasoned that quantitative analysis of erythroid DNA in the plasma would be able to provide information on the erythropoietic activity in the bone marrow.

To confirm the ability to measure activity of erythropoiesis in the bone marrow using plasma, patients suffering from beta-thalassemia major and aplastic anemia were recruited from the Department of Medicine, Prince of Wales Hospital, Hong Kong. Venous blood samples were collected before transfusion. The Unmeth % of plasma DNA was determined by digital PCR for each patient. These results were correlated with the hemoglobin levels. The hemoglobin levels can be measured via techniques known to one skilled in the art, e.g., by a photometric technique done on automated blood cell counters. The hemoglobin levels can be measured from an RBC portion, e.g., obtained after centrifuging.

These two groups of patients (beta-thalassemia major and aplastic anemia) represent two different spectrums of erythropoietic activity. In patients with beta-thalassemia major, the erythropoiesis is highly active. However, due to the defective production of functional beta-globin chain, the production of mature RBC is reduced. In patients with aplastic anemia, erythropoiesis is reduced leading to a decreased production of RBC.

Figure 8:
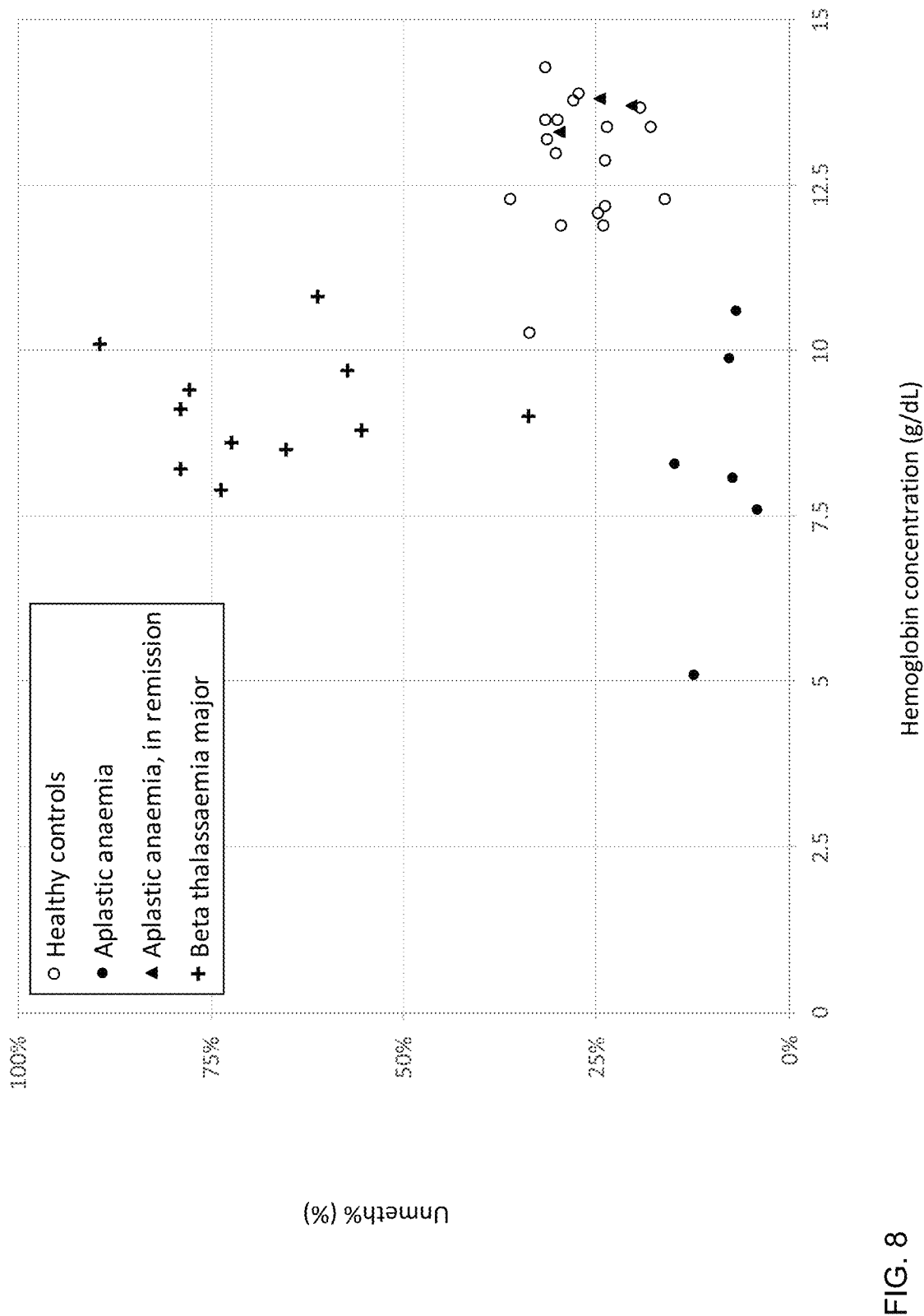
FIG. 8 is a plot of Unmeth % against hemoglobin concentrations in patients with aplastic anemia, beta-thalassemia major, and healthy control subjects according to embodiments of the present invention.

FIG. 8 is a plot of Unmeth % against hemoglobin concentrations in patients with aplastic anemia, beta-thalassemia major, and healthy control subjects according to embodiments of the present invention. In beta-thalassemia patients, the hemoglobin concentrations were reduced, but the Unmeth % were significantly increased compared with the healthy control subjects (P<0.01, Mann-Whitney rank-sum test). In fact, the Unmeth % values in 10 (89%) out of the 11 beta-thalassemia patients were higher than the values of all the healthy control subjects. This observation is in line with the increased but defective erythropoiesis in these patients.

In contrast, for the six patients with aplastic anemia undergoing regular transfusions, their Unmeth % values were lower than the values of all the healthy control subjects. This observation is consistent with the reduced erythropoiesis in these patients.

For the three aplastic anemia patients who were in clinical remission, their hemoglobin levels were normal and did not require regular transfusion. Their Unmeth % values were not significantly different from the values of the healthy control subjects (P=0.53, Mann-Whitney rank-sum test). Accordingly, the quantitative analysis of erythroblast-specific DNA in plasma would be useful for the monitoring of patients with bone marrow dysfunction, e.g., to determine whether aplastic anemia is in remission. Further, the quantitative analysis of erythroblast-specific DNA can be used to guide treatments. For example, patients having aplastic anemia that is not in remission can be treated with regular blood transfusions.

Accordingly, the Unmeth % is higher in thalassemia patients and lower in the aplastic anemia patients. For thalassemia, the marrow is active because the patient is anemic and the marrow wants to produce more RBC to the circulation. Therefore, the rate of erythropoiesis is higher than in healthy subjects without anemia. For patients with aplastic anemia, the anemia is due to the reduced production of RBC. Overall, these results indicate that the analysis of erythroblast-specific methylation profile would be useful for reflecting the erythropoiesis activity in the bone marrow.

Patients can be diagnosed via a combination of hemoglobin measurement and Unmeth %. For example, a patient having a hemoglobin below 11.8 and an E % above 50 can be classified as having β-thalassemia. Whereas, a patient having a hemoglobin below 11.8 and an E % below 25 can be classified as having aplastic anemia.

C. Iron Deficiency Anemia and Treatment

The anemia can be due to a deficiency of a nutrient (e.g. iron, B12, folate, etc.), blood loss (e.g. due to menorrhagia or bleeding from the gastrointestinal tract) or a chronic disorder (e.g. cancer, inflammatory bowel diseases).

Figure 9:
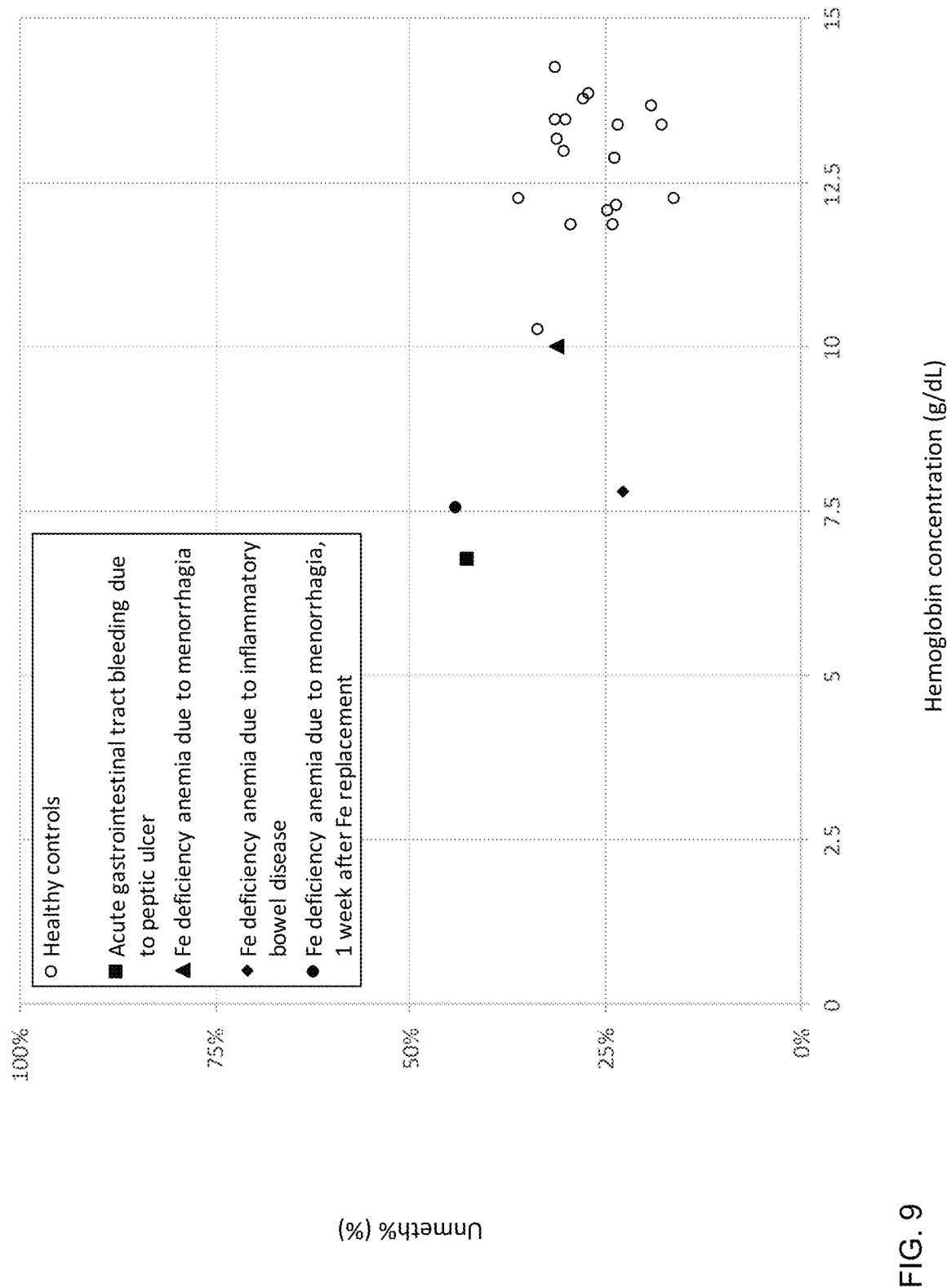
FIG. 9 is a plot of plasma Unmeth % in patients with iron (Fe) deficiency anemia and acute blood loss according to embodiments of the present invention.

FIG. 9 is a plot of plasma Unmeth % in patients with iron (Fe) deficiency anemia and acute blood loss. Three patients with iron deficiency anemia and a patient presented with acute gastrointestinal blood were studied. In two iron deficient patients, the anemia was due to menorrhagia. For one patient, the blood sample was collected before starting iron supplement. For the other one, the blood sample was collected at 1 week after starting iron supplement therapy. The third iron deficiency anemia patient suffered from inflammatory bowel disease and the blood sample was collected before starting iron supplement.

The plasma Unmeth % was determined for each patient and compared with the values of the healthy control subjects. An increased plasma Unmeth % was observed in the patient with acute gastrointestinal tract bleeding. For the two iron deficient patients with samples collected before starting iron supplement therapy, their plasma Unmeth % values were not increased compared with the healthy subjects despite having low hemoglobin levels. For the Fe deficient patient with sample collected at 1 week after starting iron supplements, an increased plasma Unmeth % was observed.

These results show that the plasma Unmeth % reflects the erythropoiesis activity in response to treatment. For example, the treatment of iron supplements shows an increased erythropoiesis activity. Further, these results show that the response in Unmeth % would be faster than the rise in hemoglobin level. The use of Unmeth % can be an early identifier of whether such a treatment is effective, and thus whether it should be continued or discontinued. Therefore, Unmeth % can provide a guide to predict the response to treatments of anemia, for example iron therapy, before changes in hemoglobin level can be observed.

In some embodiments, the plasma Unmeth % can be used to reflect the response to the treatments for anemia. For example, in patients with iron deficiency anemia, the response to oral iron supplement could vary across different subjects because of the variation in the absorption of iron through the intestinal tract. In such a scenario, the lack of increase in plasma Unmeth % after starting oral iron supplement can be used to indicate the need for intravenous iron therapy.

D. Discrimination Among Various Anemia Disorders

We recruited anemic patients suffering from aplastic anemia (AA), chronic renal failure (CRF), iron-deficiency anemia due to chronic blood loss, and β-thalassemia major. Different disease entities were recruited to represent the two ends of the spectrum of erythropoietic activity in the bone marrow.

Figure 10:
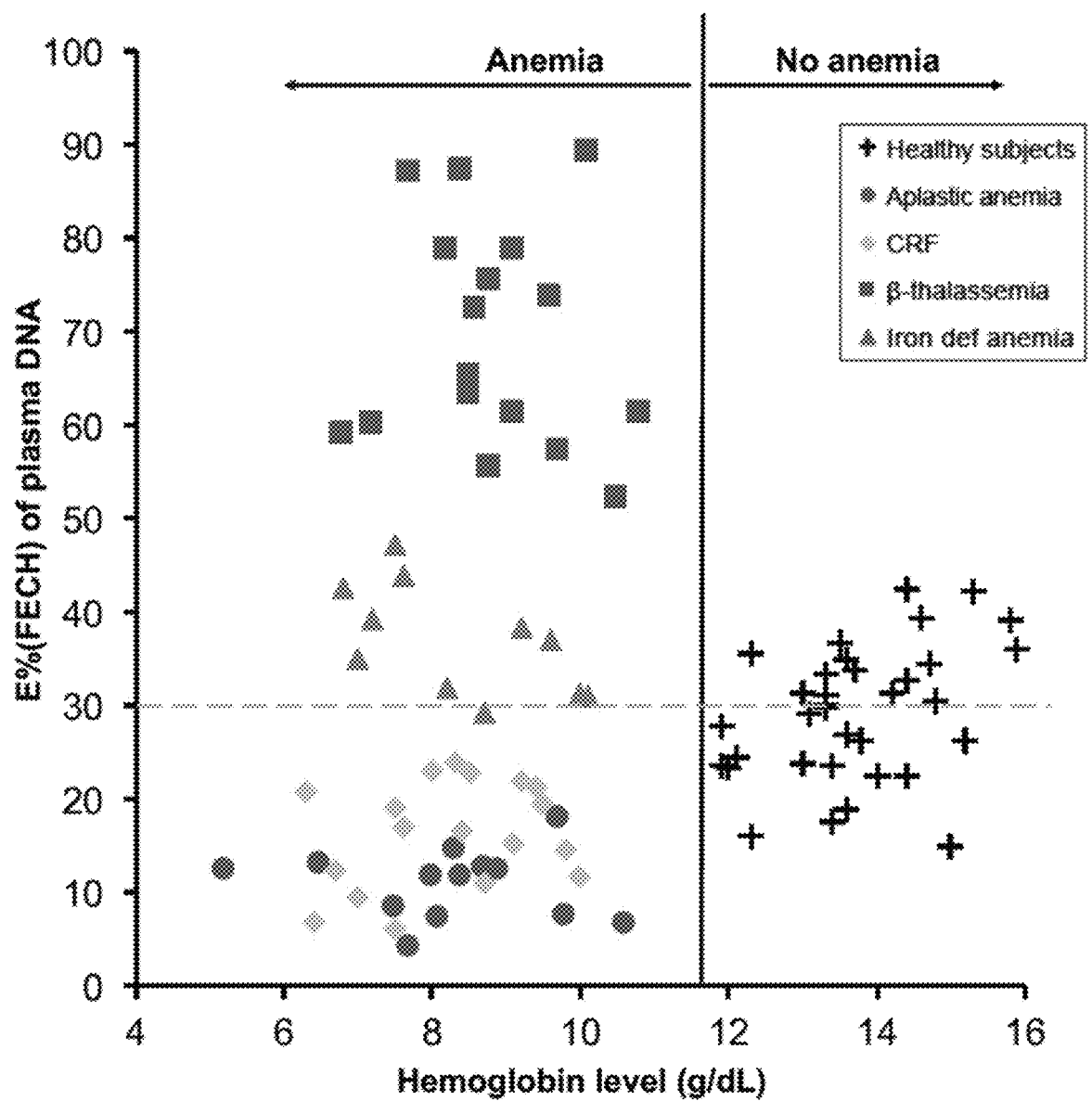
FIG. 10 shows the relationship between percentage of erythroid DNA (E % (FECH)) in the plasma and hemoglobin level among patients with aplastic anemia, chronic renal failure (CRF), β-thalassemia major, iron deficiency anemia and healthy subjects according to embodiments of the present invention.

FIG. 10 shows the relationship between percentage of erythroid DNA (E % (FECH)) in the plasma and hemoglobin level among patients with aplastic anemia, chronic renal failure (CRF), β-thalassemia major, iron deficiency anemia and healthy subjects according to embodiments of the present invention. The E % (FECH) of plasma DNA for the anemic patients and the 35 healthy controls are plotted against the hemoglobin level. The horizontal dotted line represents the median E % of healthy subjects. The vertical line corresponds to a cutoff value (11.5, as depicted) of the measured hemoglobin level between subjects having anemia and subjects not having anemia.

We analyzed the E % of plasma DNA in 13 AA patients who fulfilled the diagnostic criteria (28) and failed to respond to immunosuppressive therapy. The median E % of plasma DNA of the AA group was 12.4% (interquartile range: 7.5-13.7%), which was significantly lower than that of healthy controls (P<0.0001, Mann-Whitney rank sum test; FIG. 10). Similarly, the median E % result of 18 CRF patients requiring dialysis was 16.8% (interquartile range: 12.2-21.0%), which was also significantly lower than that of healthy controls (P<0.0001, Mann-Whitney rank sum test; FIG. 10). These findings are concordant with the pathophysiology of reduced erythropoietic activity in AA(28, 29) and CRF patients(30).

For patients with β-thalassemia major, the bone marrow is trying to compensate the hypoxic stress with increased but ineffective erythropoiesis (31). Among the 17 recruited β-thalassemia major patients, the median E % of plasma DNA was 65.3% (interquartile range: 60.1-78.9%), which was significantly higher than that of healthy controls (P<0.0001, Mann-Whitney rank sum test; FIG. 10).

For the subjects with iron deficiency anemia, we recruited 11 patients who suffered from iron deficiency anemia due to menorrhagia or peptic ulcer disease (transferrin saturation <16% or serum ferritin level <30 ng/ml). Their median E % of plasma DNA was 37.8% (interquartile range: 31.8-43.0%), which was significantly higher than that of healthy controls (P=0.002, Mann-Whitney rank sum test; FIG. 10). The finding may be explained by the compensatory increase in marrow erythropoietic activity as a response to chronic blood loss (32).

Accordingly, patients can be diagnosed via a combination of hemoglobin measurement and E %. As examples, a patient having a hemoglobin below 11.5 (or other value) and an E % above 50 can be classified as having anemia of increased erythropoietic activity, e.g., β-thalassemia. Whereas, a patient having a hemoglobin level below 11.5 and an E % below 50 and above 28 can be classified as having anemia of intermediate erythropoietic activity, e.g., iron deficient anemia. And, a patient having a hemoglobin level below 11.5 and an E % below 28 can be classified as having anemia of reduced erythropoietic activity, e.g., aplastic anemia or chronic renal failure.

In some embodiments, to determine the classification of a hematological disorder, a hemoglobin level of the blood sample can be measured. The hemoglobin level can be compared to a hemoglobin threshold (e.g., 11.5). The classification of the hematological disorder can thus be further based on the comparing of the hemoglobin level to the hemoglobin threshold, in addition to a methylation level.

Figures 11A, 11B:
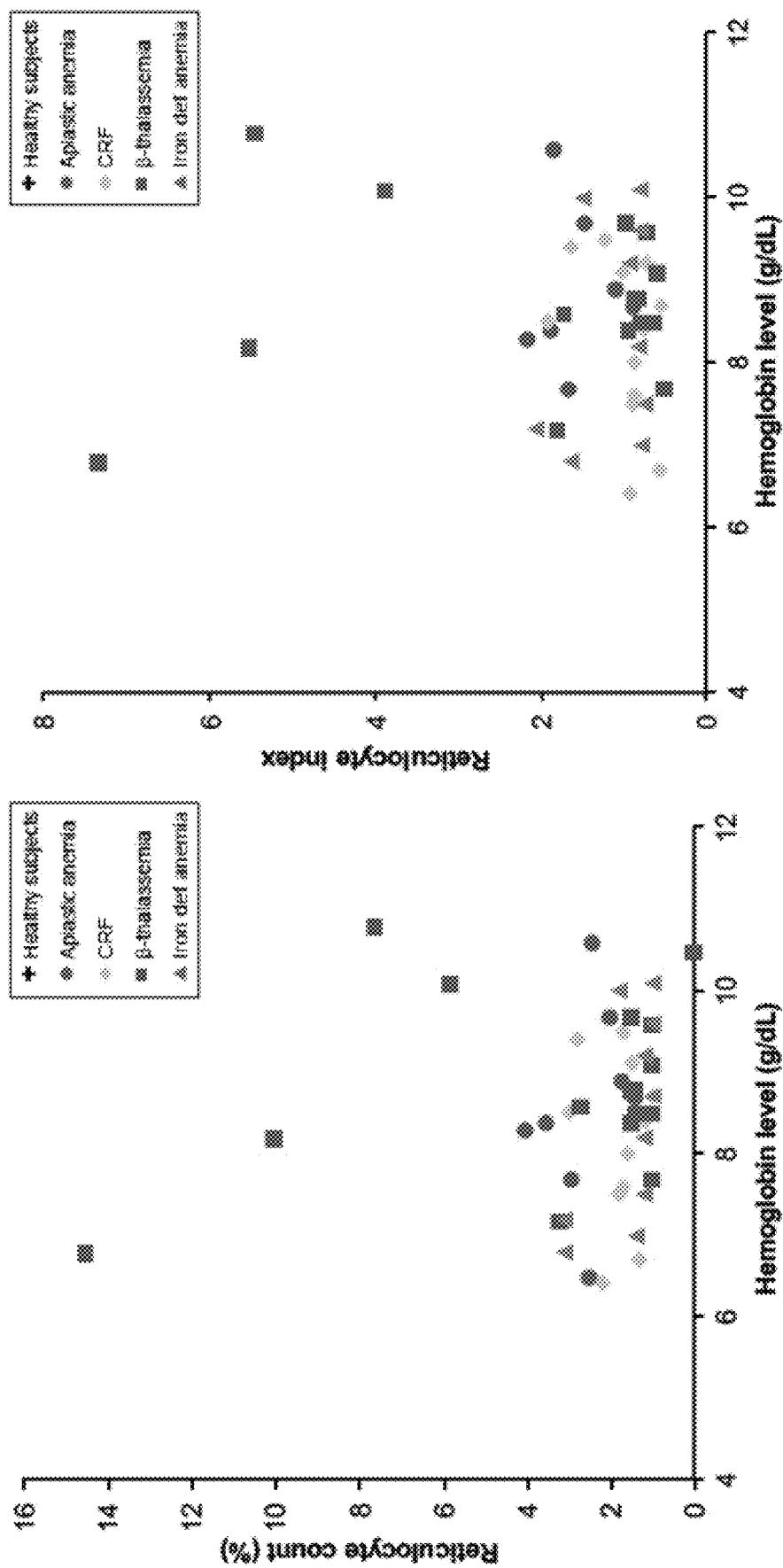
FIGS. 11A and 11B show relationships between reticulocyte count/index and hemoglobin level among anemic patients with aplastic anemia, chronic renal failure (CRF), β-thalassemia major, and iron deficiency anemia according to embodiments of the present invention.

A summary of the E % (FECH), red blood cell, and reticulocyte parameters of the subjects are shown in Tables 5 & 6 and FIGS. 11A and 11B respectively.

TABLE 5

Table summarizing the median percentage of erythroid DNA
(E % (FECH)) in the plasma DNA of healthy subject and anemic patients.

| E % (FECH) | Median E % (Interquartile range) |
|---|---|
| Healthy controls | 30.1% (23.8-34.8%) |
| Aplastic anemia - non-responsive to treatment | 12.4% (7.5-13.7%) |
| Aplastic anemia - responsive to treatment | 22.5% (17.2-27.1%) |
| Chronic renal failure | 16.8% (12.2-21.0%) |
| Iron deficiency anemia | 37.8% (31.8-43.0%) |
| β-thalassemia major | 65.3% (60.1-78.9%) |
| Myelodysplastic syndrome | 50.3% (37.4-60.8%) |

In Table 6 below, median values and interquartile ranges (bracketed) are shown. The following abbreviations are used: hematocrit as Hct, mean corpuscular volume as MCV, mean cell hemoglobin as MCH, mean cell hemoglobin concentration as MCHC, and red cell distribution width as RDW.

TABLE 6

Red blood cell (RBC) parameters of healthy controls and anemic patients recruited.

| Health and Disease Status | RBC count ($\times 10^{12}$/L) | Hct (L/L) | MCV (fL) | MCH (pg) | MCHC (g/dL) | RDW (%) |
|---|---|---|---|---|---|---|
| Healthy controls | 4.60 (4.36-4.95) | 0.412 (0.396-0.437) | 91.2 (87.5-94.1) | 30.0 (29.1-31.2) | 33.1 (32.5-33.7) | 13.3 (12.8-13.6) |
| Aplastic anemia | 2.49 (2.37-2.74) | 0.244 (0.238-0.285) | 97.8 (89.4-103.1) | 34.0 (31.2-35.5) | 34.5 (33.8-34.8) | 17.9 (14.5-21.5) |
| Chronic renal failure | 2.82 (2.63-3.22) | 0.252 (0.222-0.269) | 87.2 (83.1-92.9) | 29.3 (27.5-30.9) | 33.2 (32.5-33.7) | 15.6 (14.2-17.1) |
| Iron deficiency anemia | 4.04 (3.90-4.31) | 0.272 (0.253-0.311) | 66.6 (65.1-70.8) | 19.9 (19.5-21.7) | 30.2 (30.1-30.7) | 18.6 (17.5-20.0) |
| β-thalassemia major | 3.19 (3.08-3.41) | 0.253 (0.248-0.282) | 81.0 (77.4-81.8) | 27.3 (26.3-28.1) | 33.9 (33.4-34.1) | 16.7 (14.4-18.2) |
| Myelodysplastic syndrome | 2.31 (2.16-2.50) | 0.218 (0.207-0.238) | 89.9 (86.3-99.8) | 30.4 (29.0-33.6) | 33.7 (33.0-33.8) | 19.6 (16.0-22.7) |

FIGS. 11A and 11B show relationships between reticulocyte count/index and hemoglobin level among anemic patients with aplastic anemia, chronic renal failure (CRF), β-thalassemia major, and iron deficiency anemia. The reticulocyte index is calculated as: reticulocyte count×hematocrit/normal hematocrit. As can be seen, the amount of reticulocytes (immature RBCs) in the blood does not provide a reliable discrimination among the different disorders. These results show that the reticulocyte counts and the reticulocyte index were not able to differentiate anemia of different etiology, e.g., differentiating thalassemia from aplastic anemia.

E. Myelodysplastic Syndrome and Polycythemia Rubra Vera

Figure 12:
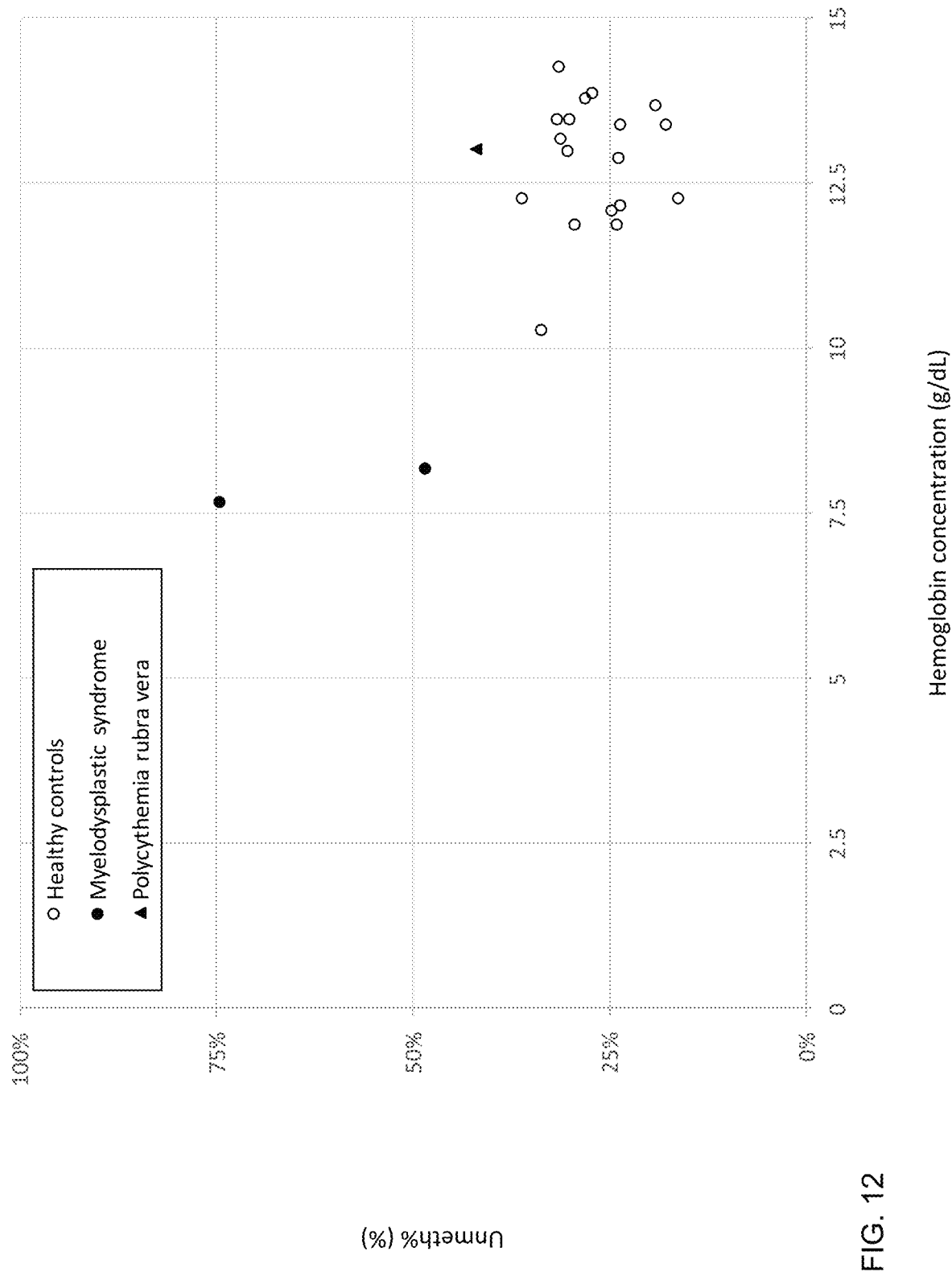
FIG. 12 is a plot of plasma Unmeth % in patients with myelodysplastic syndrome and polycythemia rubra vera according to embodiments of the present invention.

FIG. 12 is a plot of plasma Unmeth % in patients with myelodysplastic syndrome and polycythemia rubra vera. In patients with myelodysplastic syndrome, an increased plasma Unmeth % was observed with the reduced hemoglobin level. An increased plasma Unmeth % was also observed in a patient with polycythemia rubra vera. These results show that the detection and quantification of erythroblastic DNA methylation signature in plasma is useful for the detection and monitoring of abnormal proliferation or dysplasia of bone marrow involving the myeloblastic cells.

Accordingly, as one can see, these two hematological disorders also show higher cell-free DNA of erythroblasts, thereby allowing a detection of a hematological disorder. In some embodiments, the exact diagnosis can be based on histological examination of bone marrow biopsy. Thus, a bone marrow biopsy can be performed in response to detecting a high Unmeth %. Similarly, a bone marrow biopsy can be performed in response to detecting a low Unmeth % in the presence of anemia but the absence of nutritional deficiency, for example iron deficiency, vitamin B12 deficiency, or folate deficiency. Such bases for a bone marrow biopsy can reduce the number of such biopsies while still allowing for monitoring the health of bone marrow. Accordingly, Unmeth % would be more useful to monitor treatment response.

F. Other Discrimination for Anemia

Discrimination between other disorders is also possible.

1. Aplastic Anemia (AA) and Myelodysplastic Syndrome (MDS)

Both aplastic anemia and MDS are bone marrow failure conditions. Despite their similar clinical features of pancytopenia, these two disease entities have different pathophysiologic mechanisms. In AA, there is hypocellular marrow without features of dysplasia. In MDS, there is usually hypercellular marrow and dysplasia involving one or multiple lineages (33), although hypocellular MDS has also been recognized.

Figures 13A, 13B:
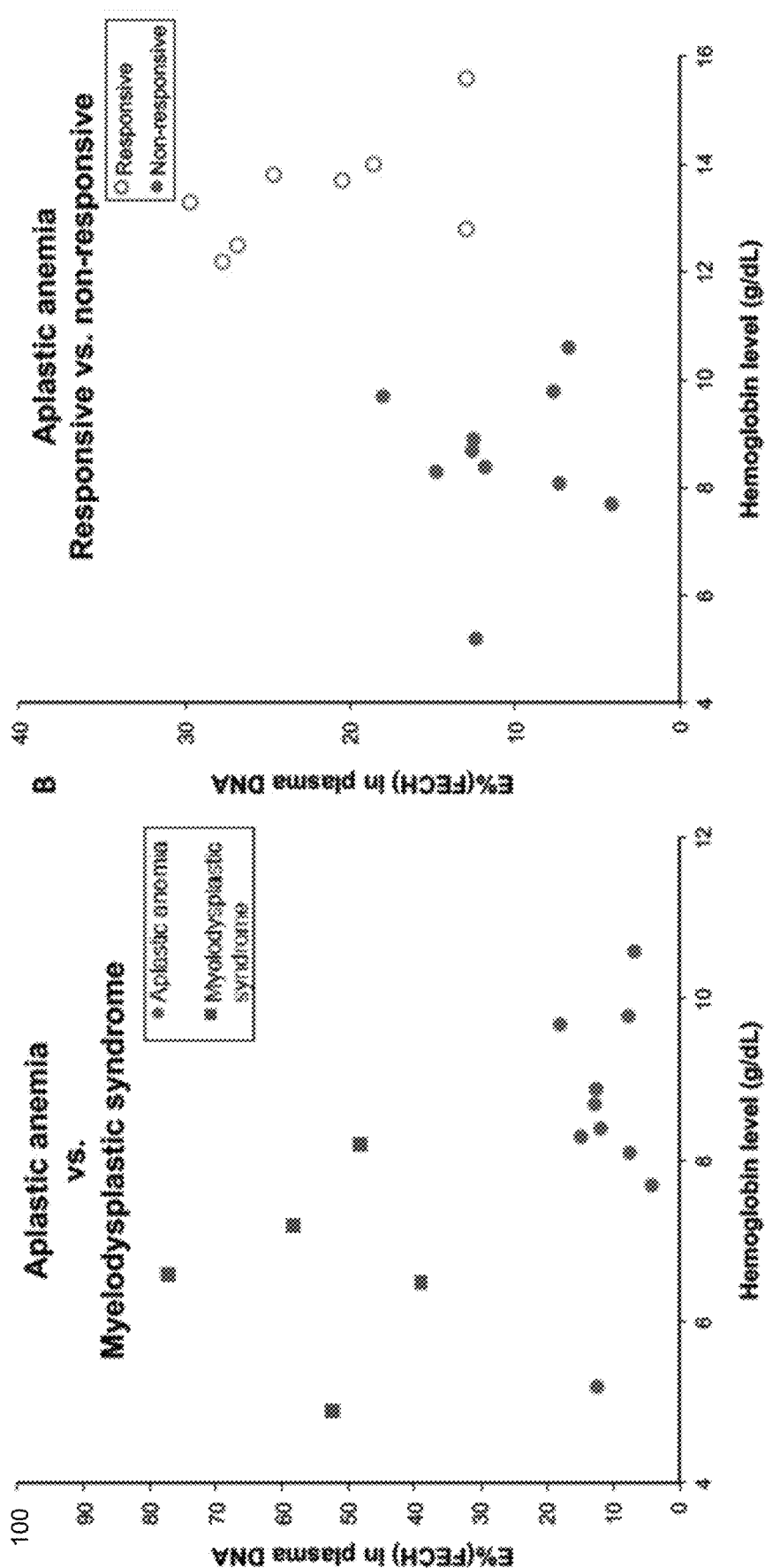
FIG. 13A shows a percentage of erythroid DNA (E % (FECH)) in plasma between patients with aplastic anemia (AA) and myelodysplastic syndrome (MDS) according to embodiments of the present invention.
FIG. 13B shows a percentage of erythroid DNA (E % (FECH)) in plasma between treatment-responsive and treatment non-responsive groups in aplastic anemia according to embodiments of the present invention.

FIG. 13A shows a percentage of erythroid DNA (E % (FECH)) in plasma between patients with aplastic anemia (AA) and myelodysplastic syndrome (MDS) according to embodiments of the present invention. The median E % of plasma DNA from 8 MDS patients was 50.3% (range: 37.4-60.8%). Two cases had MDS with unilineage dysplasia, 4 had multilineage dysplasia, and 2 had MDS with excess blasts (34). All of their previous bone marrow biopsies showed erythroid hypercellularity. The median E % for the MDS patients was significantly higher than that of the 13 recruited AA patients (P<0.0001, Mann-Whitney rank sum test; FIG. 13A). The higher median E % result among the MDS patients is concordant with the marrow biopsy findings and the pathophysiology of ineffective erythropoiesis in MDS.

Accordingly, MDS can be differentiated from aplastic anemia using E % or other methylation level. For example, a cutoff value of 30 can be used to classify a sample as corresponding to aplastic anemia or MDS.

2. Treatment Responsive and Treatment Non-Responsive Groups of AA

FIG. 13B shows a percentage of erythroid DNA (E % (FECH)) in plasma between treatment-responsive and treatment non-responsive groups in aplastic anemia according to embodiments of the present invention. We analyzed 8 additional aplastic anemia patients who responded to immunosuppressive therapy, thereby increasing the hemoglobin level. The median E % of plasma DNA of the treatment-responsive group was 22.5% (interquartile range: 17.2-27.1%), which was higher than that of the non-responsive group (median: 12.3%; interquartile range: 7.5-13.7%) (P=0.0003, Mann-Whitney rank sum test; FIG. 13B). There was a small yet significant difference between the E % results of the treatment-responsive group and the healthy controls (P=0.01, Mann-Whitney rank-sum test).

These results reflect a recovery of erythropoietic activity in the bone marrow. As recovery in E % can show up earlier than hemoglobin levels, E % can be used to determine early whether a patient is responding to the immunosuppressive therapy. When the patient is not responding, other treatments (e.g., more aggressive treatments) can be pursued, for example, carrying out stem cell transplantation or prescribing bone marrow stimulants (e.g., sargramostim, filgrastim, and pegfilgrastim).

G. Leukemia

Other blood disorders besides leukemia can also be detected using an erythroblast-specific DMR, such in FECH.

Figure 14:
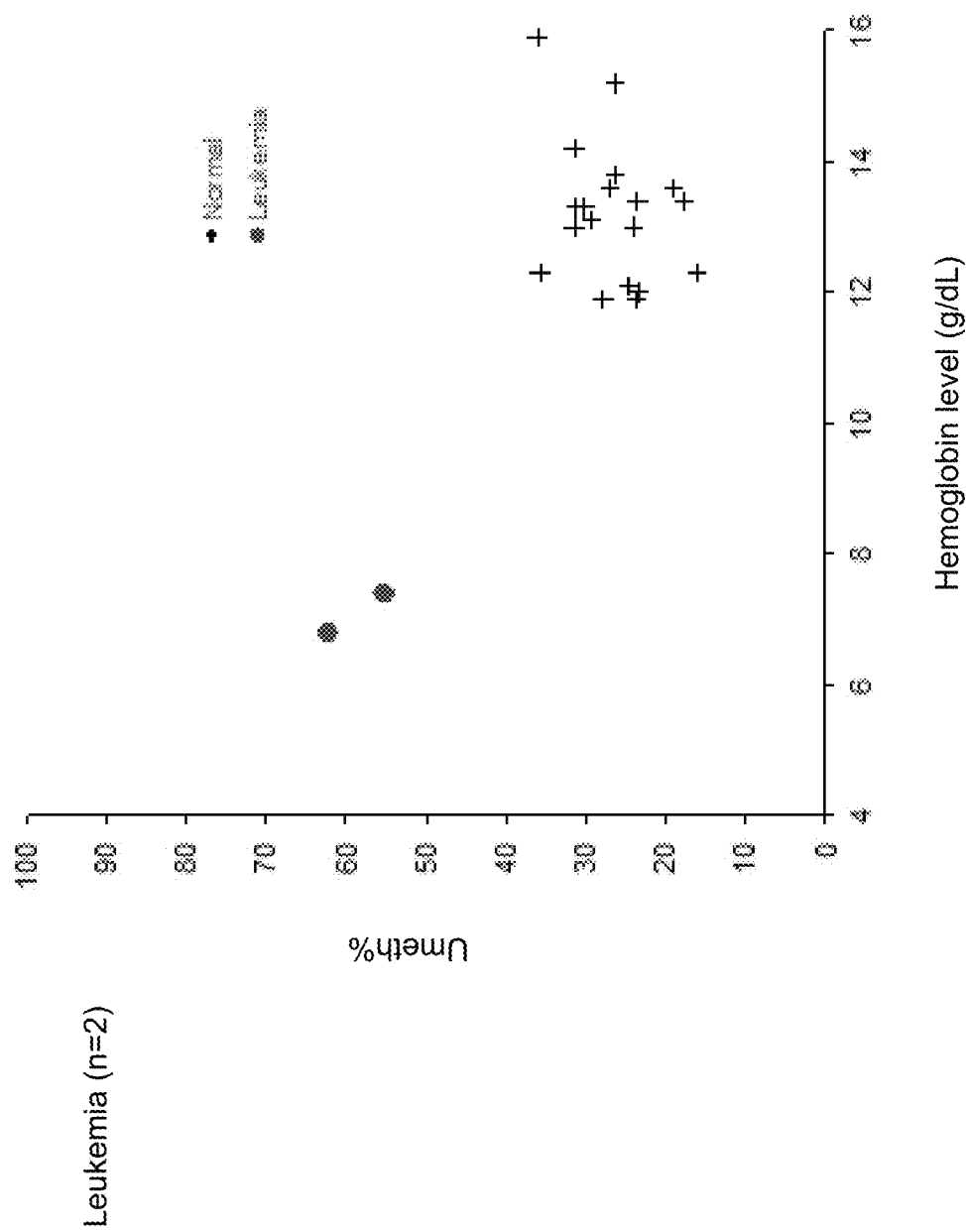
FIG. 14 is a plot of Unmeth % in plasma against hemoglobin concentrations in normal subjects and two patients with leukemia according to embodiments of the present invention.

FIG. 14 is a plot of Unmeth % in plasma against hemoglobin concentrations in normal subjects and two patients with leukemia according to embodiments of the present invention. Unmeth % is determined using the FECH DMR. The Unmeth % values in plasma of the patients with leukemia or myeloproliferative disorder are higher than the median Unmeth % in plasma of normal subjects. This observation is in line with the observation that the increased but defective erythropoiesis in patients with leukemia. Thus, a cutoff value of about 45 could be used for Unmeth % to distinguish between healthy subjects and subjects having leukemia, thereby determining a level of a hematological disorder. The hemoglobin level can also be used, e.g., a patient with hemoglobin below 8 may be identified as having leukemia as opposed to beta-thalassemia, which generally has hemoglobin level between 8 and about 11.8, as shown in FIG. 10.

VI. RESULTS FOR OTHER METHYLATION MARKERS

We analyzed the E % based on the other two DMRs in the plasma of a subset of samples to validate the above E % results from the FECH gene-associated DMR. Similar differences in the percentage of erythroid DNA in the plasma between healthy subjects and aplastic anemia and β-thalassemia major patients were observed using the other two erythroblast-specific DMRs as the DMR in the FECH gene.

A. Other Two Erythroblast-Specific DMRs

The other two DMRs located on chromosome 12 are also hypomethylated. The genomic region associated with these two DMRs had not been previously identified as within any annotated gene.

Figure 15B:
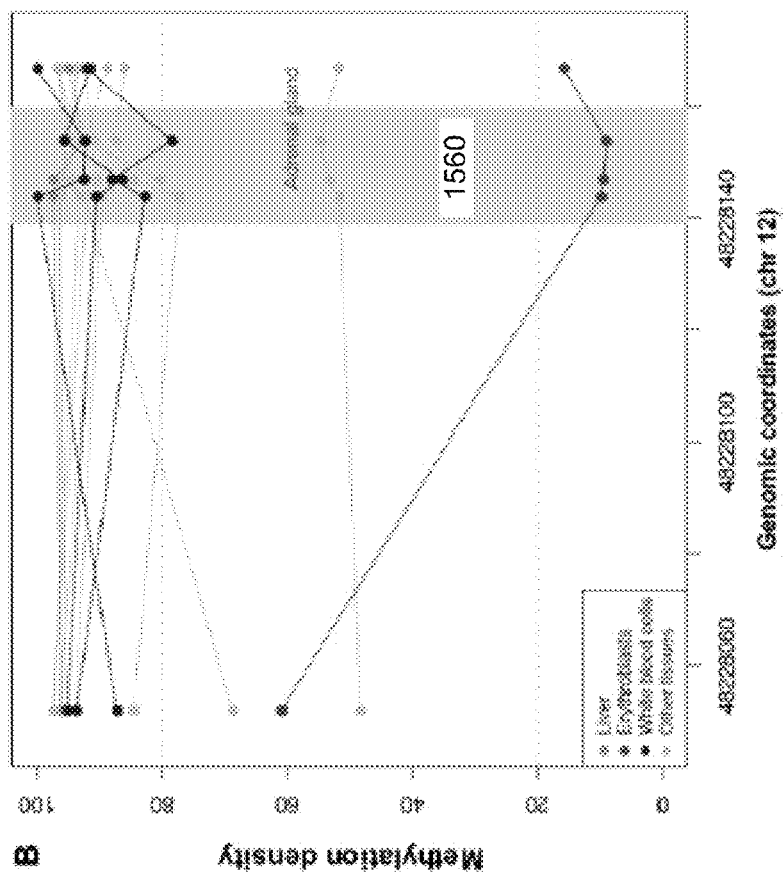
FIGS. 15A and 15B show methylation densities of the CpG sites within the erythroblast-specific DMRs on chromosome 12 according to embodiments of the present invention.
Figure 15A:
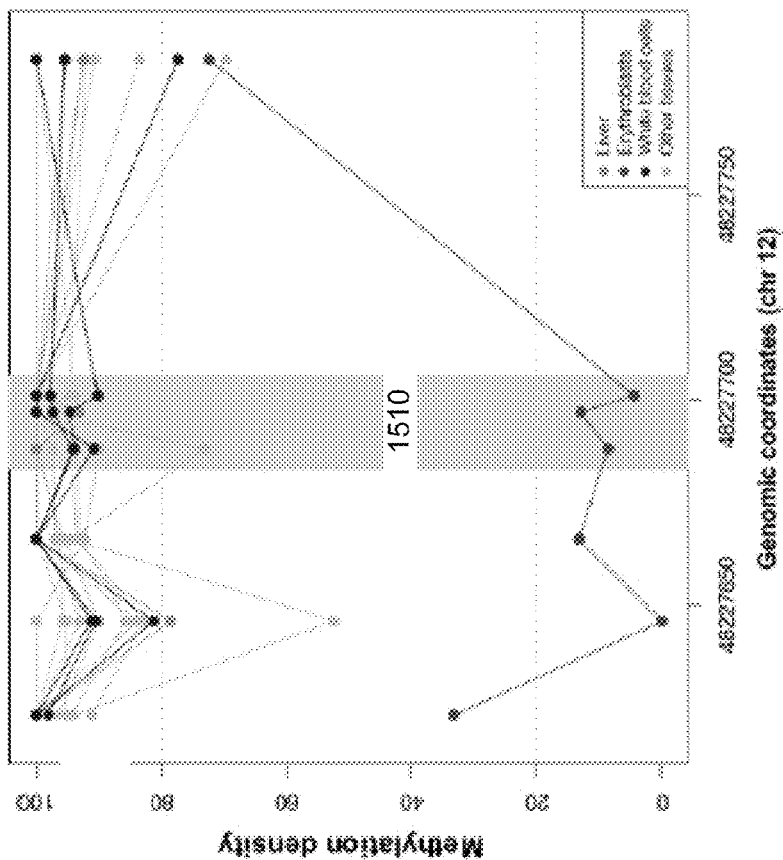

FIGS. 15A and 15B show methylation densities of the CpG sites within the erythroblast-specific DMRs on chromosome 12 according to embodiments of the present invention. FIG. 15A shows a region 1510 at genomic coordinates on chromosome 12: 48227688-48227701, which includes 3 sites. FIG. 15B shows a region 1560 at genomic coordinates on chromosome 12: 48228144-48228154, which also includes 3 sites. The genomic coordinates correspond to human reference genome hg19. The selected CpG sites located within the shaded region were all hypomethylated in the erythroblasts, but hypermethylated in other tissues or cell types. Other tissues represent the lung, colon, small intestines, pancreas, adrenal gland, esophagus, heart and brain.

These two other erythroblast-specific DMRs are labeled as Ery-1 and Ery-2. E % based on the other two DMRs (chr 12: 48227688-48227701 and chr 12: 48228144-48228154) would be denoted by E % (Ery-1) and E % (Ery-2), respectively.

Figure 16:
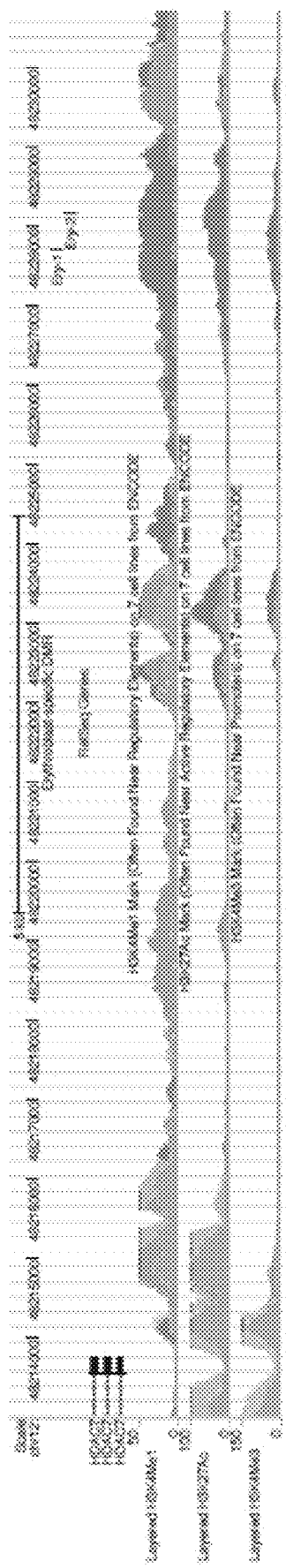
FIG. 16 shows histone modification (H3K4me1 and H3K27Ac) over two other erythroblast-specific DMRs (Ery-1 and Ery-2) from the ENCODE database.

FIG. 16 shows histone modification (H3K4me1 and H3K27Ac) over two other erythroblast-specific DMRs (Ery-1 and Ery-2) from the ENCODE database. We reviewed the publicly available data on the histone modification and CHIP-seq dataset over these two DMRs in the erythroblast cell type from the ENCODE database. The Ery-1 and Ery-2 DMRs are marked by two enhancer-associated histone modification (H3K4me1 and H3K27Ac), which are suggestive of having regulatory functions, especially that of an enhancer. The nearest downstream gene is the HDAC7 gene, which is approximately 15 kb away.

B. Erythroblast-Enriched Samples

We analyzed the percentage of erythroid DNA based on the other two DMRs in the erythroblast-enriched samples from 8 umbilical cord blood samples described before. The E % (Ery-1) and E % (Ery-2) of the DNA extracted from the pooled samples were 66.5% and 68.5%. These E % values were similar to the E % based on the FECH gene-associated DMR, i.e. 67%. Given the similar findings from all the three DMRs, the lower-than-expected E % value (i.e., lower than expected when enrichment is performed) might be due to the incomplete selectivity of the enrichment protocol.

C. Correlation of E % in Buffy Coat of β-Thalassemia Major Patients to Erythroblasts The percentage of erythroid DNA based on the two DMRs were analyzed in the buffy coat DNA of the same group of β-thalassemia major patients. The E % for the two DMRs in the buffy coat DNA correlated well with the percentage of erythroblasts in a similar manner as FIG. 3A.

Figure 17A:
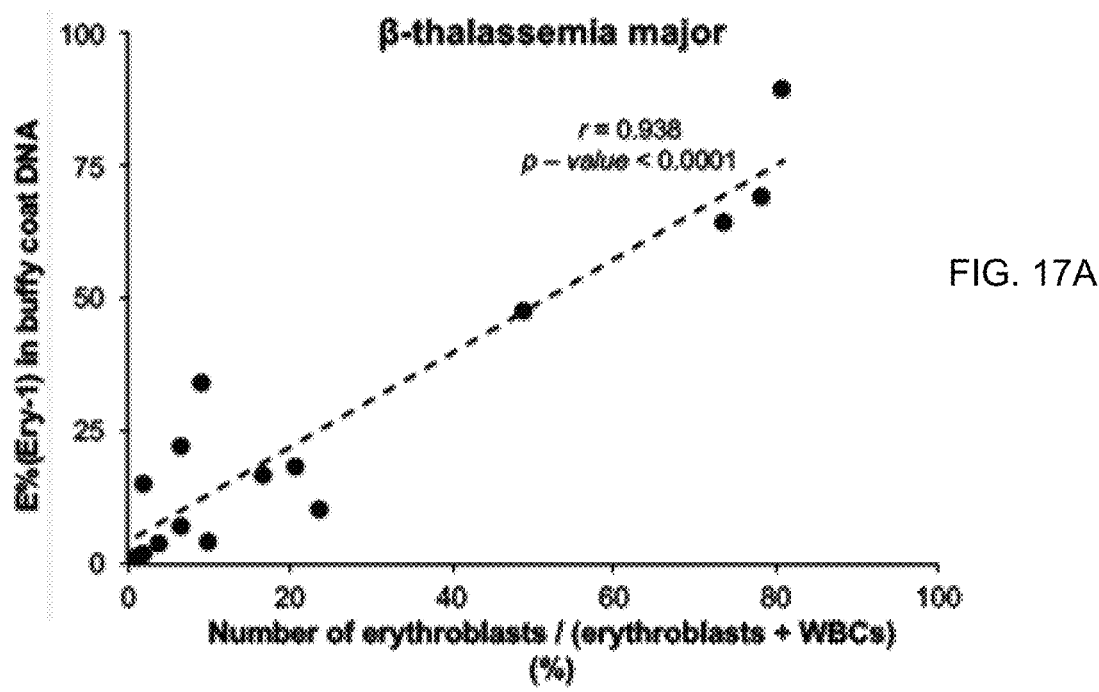
FIGS. 17A and 17B show the correlation between the percentage of erythroid DNA sequences (E %) in the buffy coat DNA of β-thalassemia major patients measured by the digital PCR assays targeting the Ery-1 marker (FIG. 17A) and the Ery-2 marker (FIG. 17B) and the percentage of erythroblasts among all peripheral white blood cells measured using an automated hematology analyzer.
Figure 17B:
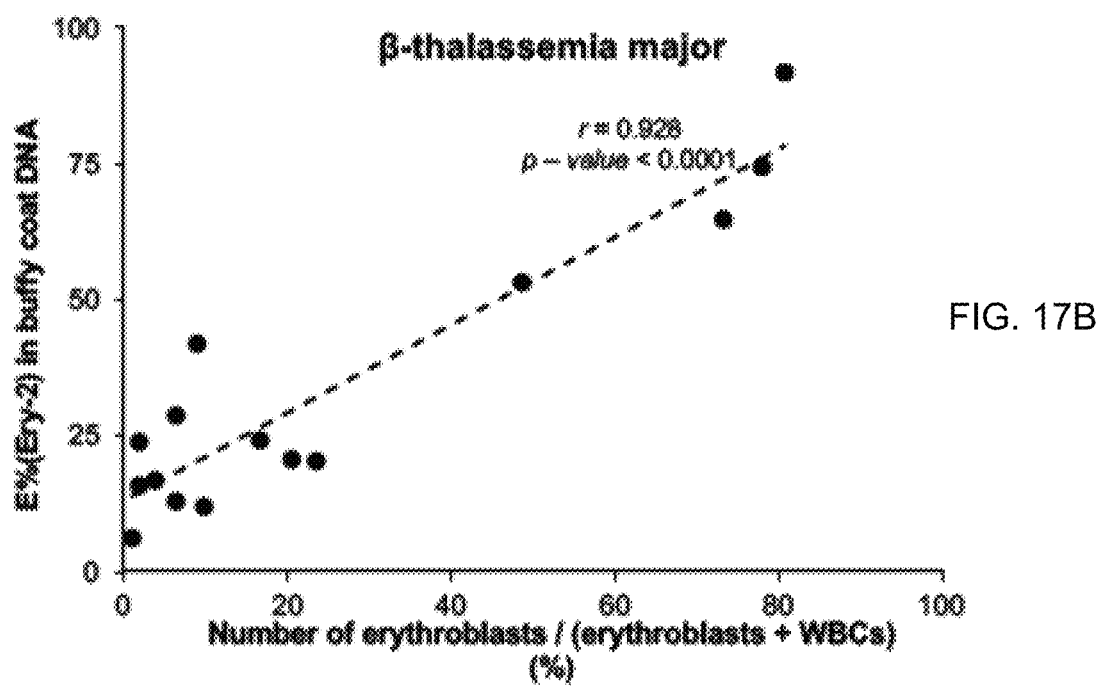

FIGS. 17A and 17B show the correlation between the percentage of erythroid DNA sequences (E %) in the buffy coat DNA of β-thalassemia major patients measured by the digital PCR assays targeting the Ery-1 marker (FIG. 17A) and the Ery-2 marker (FIG. 17B) and the percentage of erythroblasts among all peripheral white blood cells measured using an automated hematology analyzer. The E % (Ery-1) and E % (Ery-2) in buffy coat DNA correlated well with the percentage of erythroblasts among peripheral white blood cells measured by the hematology analyzer (r=0.938 & r=0.928, both P<0.0001, Pearson correlation).

Figure 18A:
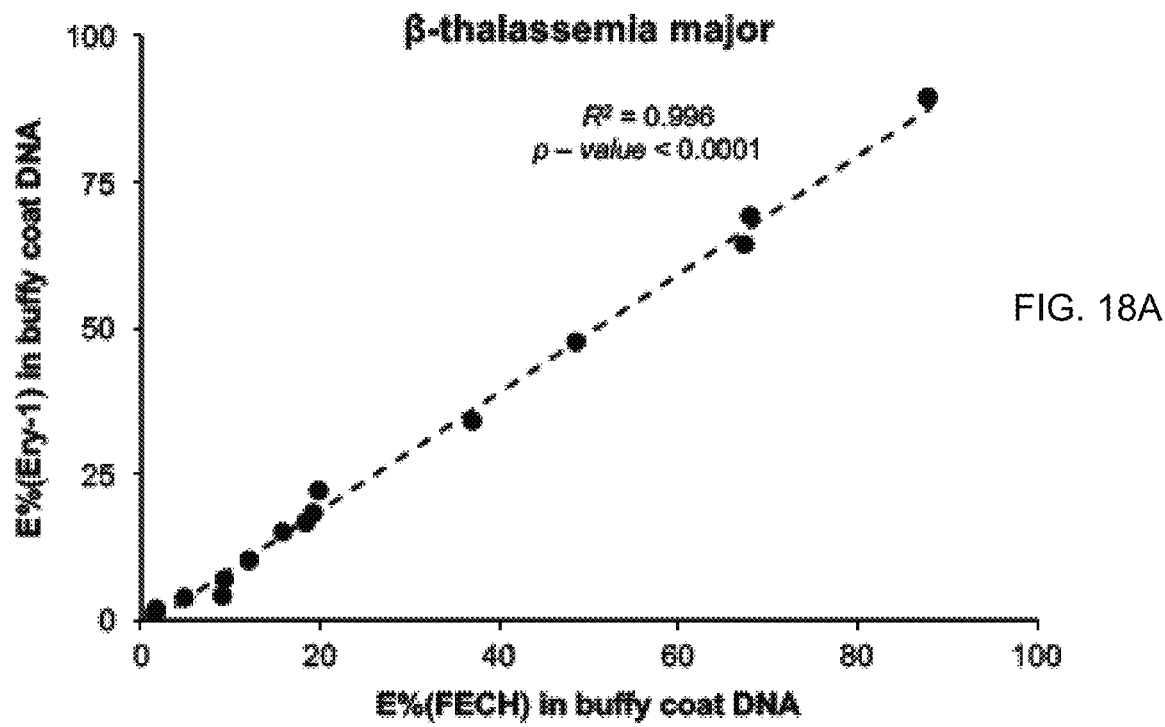
FIGS. 18A and 18B show the correlation of the E % (FECH) results and E % (Ery-1) and E % (Ery-2) in the buffy coat DNA of β-thalassemia major patients.
Figure 18B:
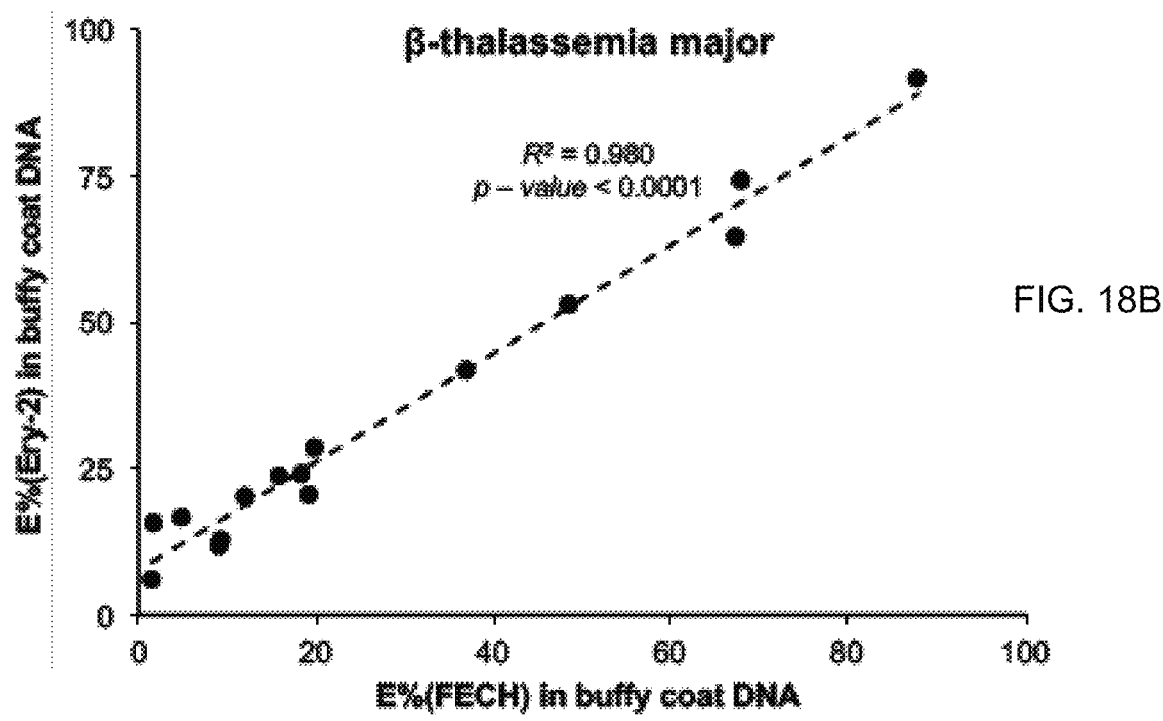

FIGS. 18A and 18B show the correlation of the E % (FECH) results and E % (Ery-1) and E % (Ery-2) in the buffy coat DNA of β-thalassemia major patients. The E % results derived from these two DMRs also correlated well with the paired E % results derived from the FECH gene marker site in the buffy coat DNA of the 15 β-thalassemia major patients.

D. E % in Plasma of Healthy Subjects and Anemic Patients

We analyzed the E % (Ery-1) and E % (Ery-2) in the plasma DNA of healthy subjects and patients with aplastic anemia and β-thalassemia major. The E % results based on the three erythroblast-specific DMRs in the same group of healthy subjects, 7 aplastic anemia, and 9 β-thalassemia major patients were analyzed.

Figure 19:
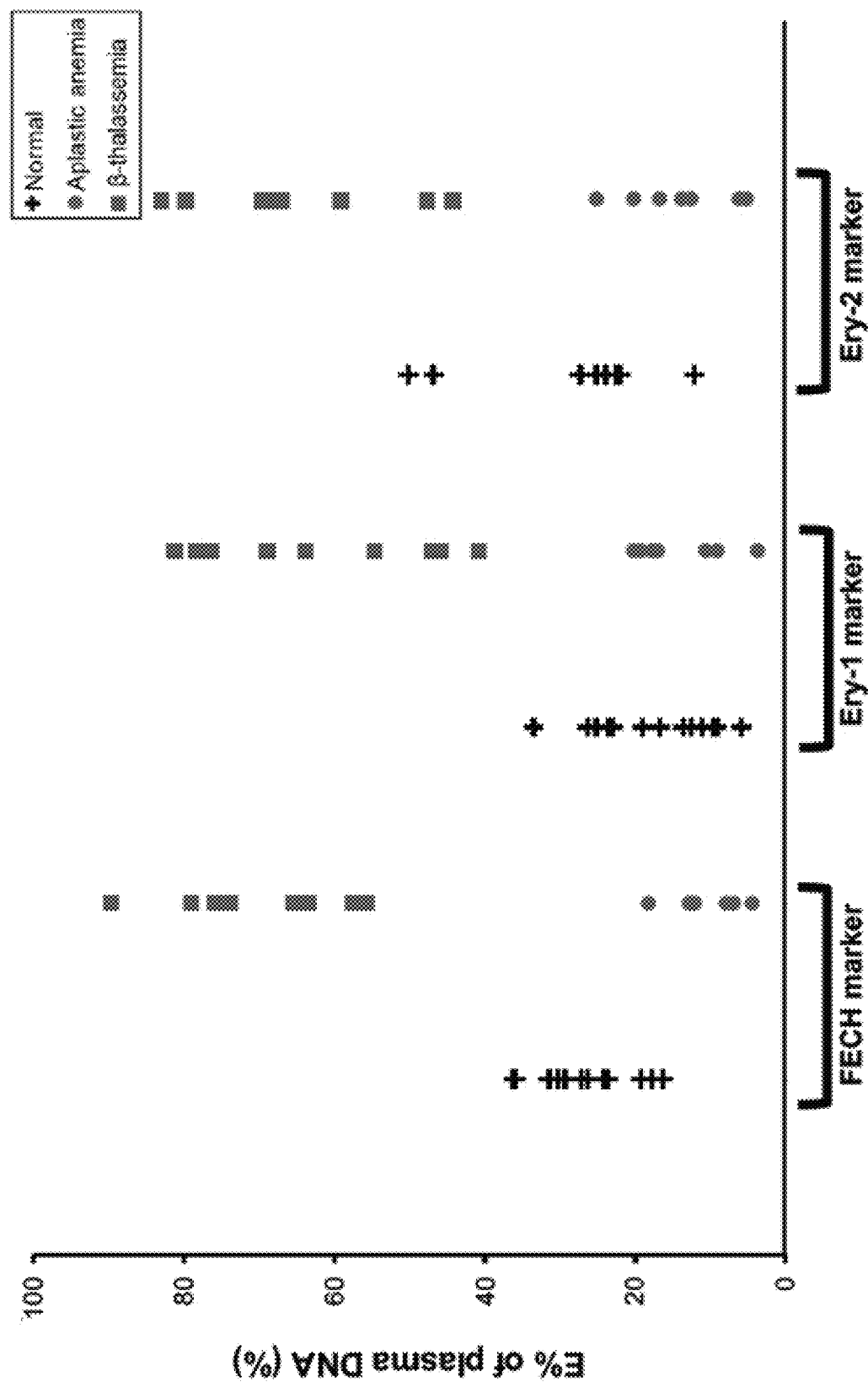
FIG. 19 shows the percentage of erythroid DNA in healthy subjects and patients with aplastic anemia and β-thalassemia major using digital PCR analysis targeting the three erythroblast-specific DMRs according to embodiments of the present invention.

FIG. 19 shows the percentage of erythroid DNA in the healthy subjects and the patients with aplastic anemia and β-thalassemia major using digital PCR analysis targeting the three erythroblast-specific DMRs according to embodiments of the present invention. The median E % (Ery-1) in the plasma DNA of 13 healthy subjects was 16.7% (interquartile range: 10.9-23.5%) and the median E % (Ery-2) in the same group of healthy subjects was 25.0% (interquartile range: 22.2-27.3%). Based on Ery-1 marker, the E % (Ery-1) of patients with aplastic anemia and β-thalassemia major were 13.78% and 61.69% respectively. Based on the Ery-2 marker, the E % (Ery-2) of patients with aplastic anemia and β-thalassemia major were 14.13% and 64.95% respectively. Similar differences in the percentage of erythroid DNA in the plasma between healthy subjects and aplastic anemia and β-thalassemia major patients were observed using the two erythroblast-specific DMRs as the erythroblast-specific DMR in the FECH gene.

VII. TREATMENT RESULTS

As described above, E % can be used to monitor treatment efficacy for anemia.

A. Measurements of E % (FECH) in Plasma DNA in Iron Deficiency Anemia Patients Before and after Iron Therapy We monitored the serial changes in hemoglobin level, reticulocyte counts, and E % of plasma DNA in 4 patients with iron deficiency anemia receiving intravenous iron therapy due to intolerance to gastrointestinal side effects from oral iron. Instead of patients on oral iron therapy, we chose to observe the changes in this group of patients to avoid the possible confounding factor of different treatment responses due to variable gastrointestinal absorption. We measured these parameters before and at two days after the treatment.

Figure 20B:
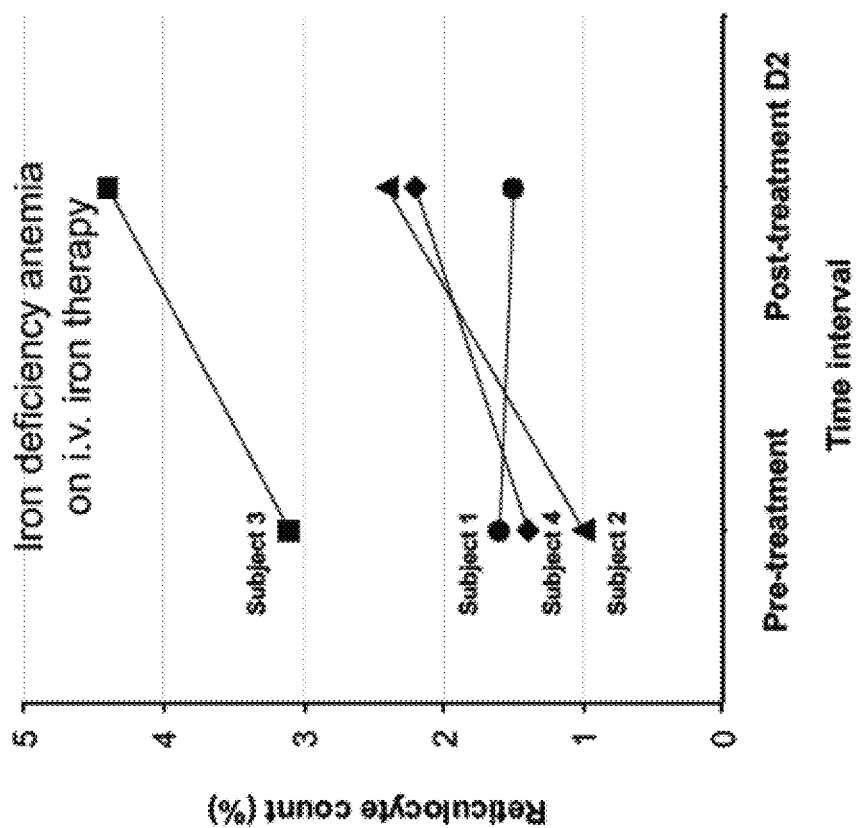
FIGS. 20A and 20B shows serial measurements of the percentage of erythroid DNA (E % (FECH)) in plasma DNA and percentage of reticulocyte counts of iron deficiency anemia receiving intravenous iron therapy at pre-treatment state and two days after treatment according to embodiments of the present invention.
Figure 20A:
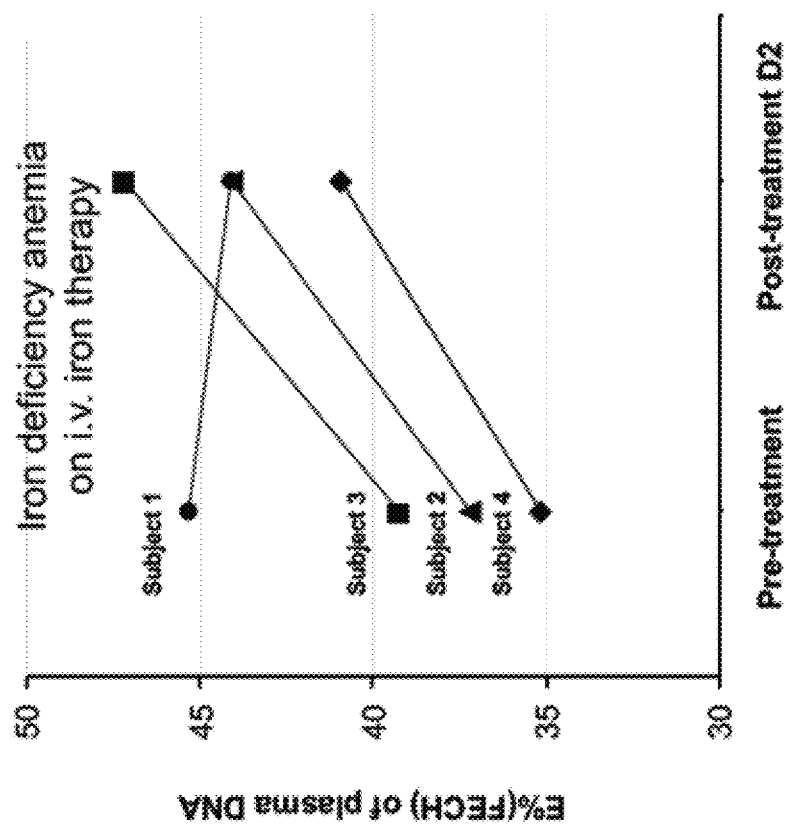

FIGS. 20A and 20B shows serial measurements of the percentage of erythroid DNA (E % (FECH)) in plasma DNA and percentage of reticulocyte counts of iron deficiency anemia receiving intravenous iron therapy at pre-treatment state and two days after treatment according to embodiments of the present invention. FIG. 20A shows serial change in E % of plasma DNA. FIG. 20B shows serial change in percentage of reticulocyte counts.

Except for subject 1, the E % of plasma DNA and reticulocyte counts increased while the hemoglobin level initially remained static just after the start of the treatment. As to the eventual change in hemoglobin level, subjects 3 and 4 eventually had a drastic change in the level, of 84.7% and 75.3% respectively. Subject 2 defaulted follow-up and did not provide additional sample for hemoglobin measurement after treatment. Subject 1, who had a minimal change in E % of plasma DNA, had the least increase in the hemoglobin level (12.2.%). Thus, the change in E % of plasma DNA can demonstrate the dynamic response in bone marrow erythropoietic activity to iron therapy, and be used as an early predictor of the patient response to treatment.

The lack of an increase in reticulocyte count of subject 1 suggests that the RBC production was not adequately responding to the iron therapy. The lack of responding to the iron therapy can also be reflected by the lack of increase in the E %, which corresponds to the bone marrow activity. But, for subject 1, the hemoglobin level before commencement of iron therapy was higher than that of the other 3 subjects, and was closer to the reference range of healthy subjects. The lack of a rise in the E % (FECH) in subject 1 can reflect the absence of a compensatory increase in the erythropoietic activity in bone marrow because of a smaller deficit in hemoglobin level from the normal level. The reticulocyte of subject 1 was initially about the same as the other subjects, and thus would not indicate that the bone marrow activity is of a sufficient level. Accordingly, for anemia having an intermediate erythropoietic activity, an E % at the upper end of normal for healthy patients can indicate a positive response to treatment, or at least an indeterminate response, and thus treatment may not be stopped in such an instance.

To bring the hemoglobin level back to normal, an increase in RBC production is required. Therefore, in the iron deficiency anemia, the normal range for E % can be considered as inappropriate. The increase in E % for subjects 2-4 indicates an appropriate response after iron therapy, as an E % in the higher range for of normal (See FIG. 10), or just above, would be expected for subjects with iron deficiency anemia. Thus, the thresholds for E % for determining whether treatment is effective can depend on a starting value for E %. The thresholds for E % can specific a particular change in value relative to the initial value, where the amount of change can depend on the initial value.

The effects of oral treatment of iron were also investigated. Patients with chronic blood loss, e.g. due to menorrhagia, would suffer from iron deficiency anemia. Iron supplementation would be used for correction of the iron deficiency status.

Figures 21A, 21B:
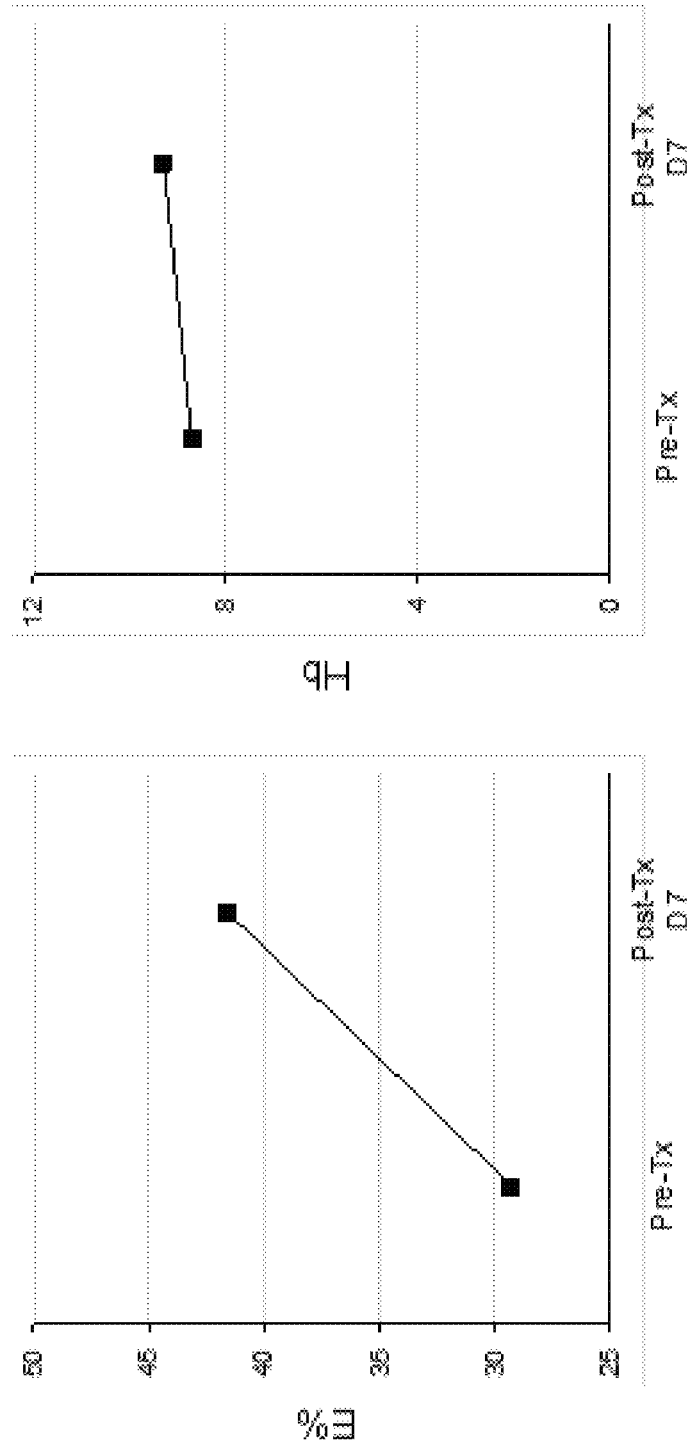
FIG. 21A shows the serial change of plasma E % at the erythroblast DMR in a patient with iron deficiency anemia due to menorrhagia receiving oral iron treatment according to embodiments of the present invention.
FIG. 21B shows the change in hemoglobin after treatment.

FIG. 21A shows the serial change of plasma E % (FECH) at the erythroblast DMR in a patient with iron deficiency anemia due to menorrhagia receiving oral iron treatment according to embodiments of the present invention. The E % in the plasma of a patient with iron deficiency anemia receiving iron treatment was analyzed before and seven days after the iron treatment. In FIG. 21A, there was an increase in the E % after receiving the iron treatment. These results suggest that the plasma E % could reflect the erythropoiesis activity in response to treatment.

FIG. 21B shows the change in hemoglobin after oral iron treatment. The hemoglobin level has not increased dramatically yet, while there was an increase in the E % (FECH) at the same time-point after treatment. This is similar to FIG. 20A, which shows that E % can be used as an early detection of whether treatment is effective.

B. Treatment for Chronic Kidney Disease (CKD)

In CKD patients, a major cause of anemia is a reduction of erythropoietin production due to kidney damage. Erythropoietin is a hormone produced by the kidney in response to low tissue oxygen levels. It stimulates the bone marrow to produce red blood cells. Exogenous erythropoietin would be used for treatment of anemia of CKD.

Figure 22:
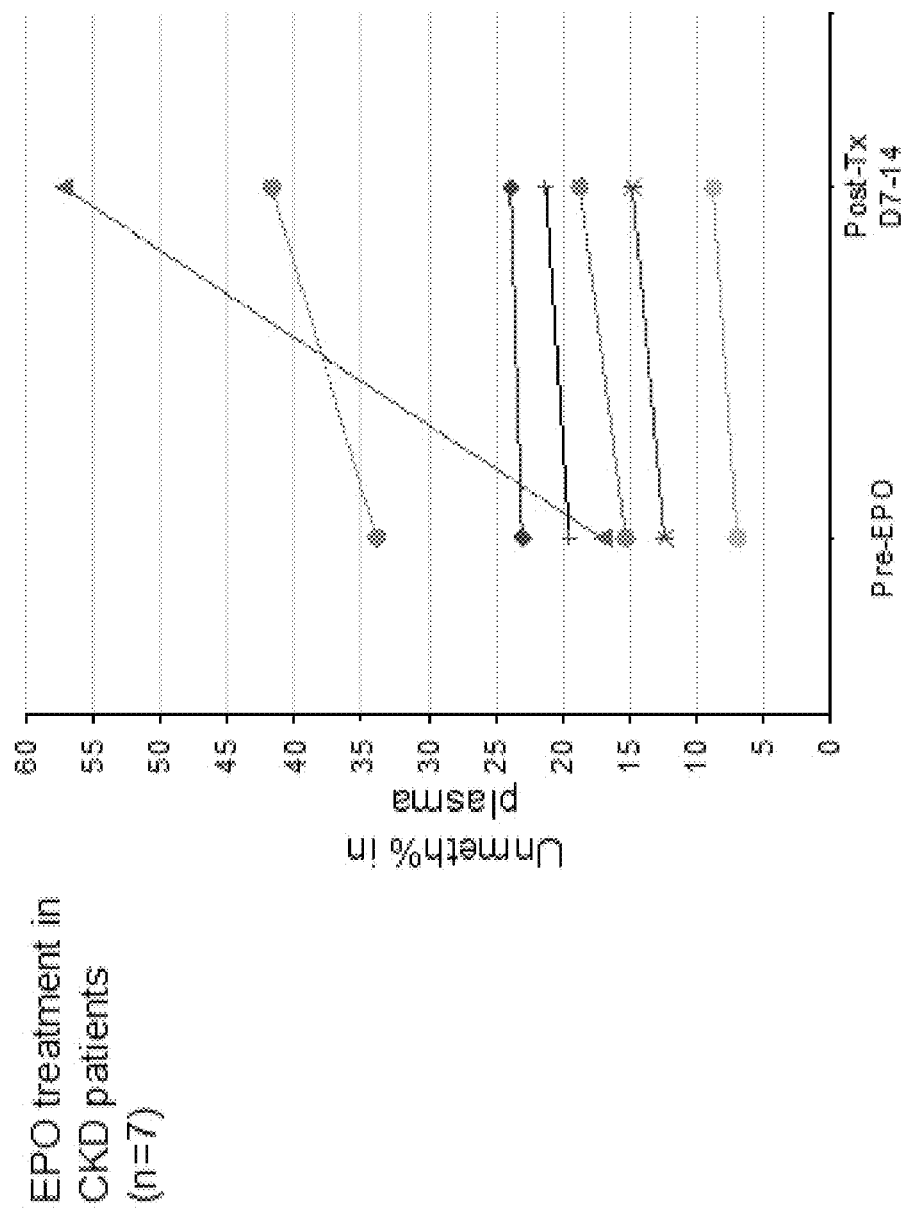
FIG. 22 shows the serial change of plasma Unmeth % at the erythroblast DMR in patients with chronic kidney disease (CKD) receiving recombinant erythropoietin (EPO) or erythropoiesis-stimulating agents (ESAs) treatment.

FIG. 22 shows the serial change of plasma Unmeth % at the erythroblast DMR in patients with chronic kidney disease (CKD) receiving recombinant erythropoietin (EPO) or erythropoiesis-stimulating agents (ESAs) treatment. The Unmeth % in the plasma of seven CKD patients receiving EPO treatment were analyzed before and 7 to 14 days after the EPO treatment. The lines of different shapes (colors) correspond to different patients. All patients showed an increase in the Unmeth % after receiving the EPO treatment. The Unmeth % values show varying levels of efficacy for the different patients. These results show that the plasma Unmeth % reflects the erythropoiesis activity in response to treatment.

C. ATG Treatment for Aplastic Anemia

Immunosuppressive therapy of aplastic anemia patients could result in hematologic recovery in 60-70% of patients (Young et al. Blood. 2006; 108(8):2509-2519). The Unmeth % values in the plasma of 4 patients with aplastic anemia receiving immunosuppressive therapy were analyzed before commencement, as well as 2 months and 4 months after the immunosuppressive therapy. All patients did not respond to the treatment, and the hemoglobin level did not resume to the normal level over the period; all four patients required regular blood transfusion.

Figures 23A, 23B:
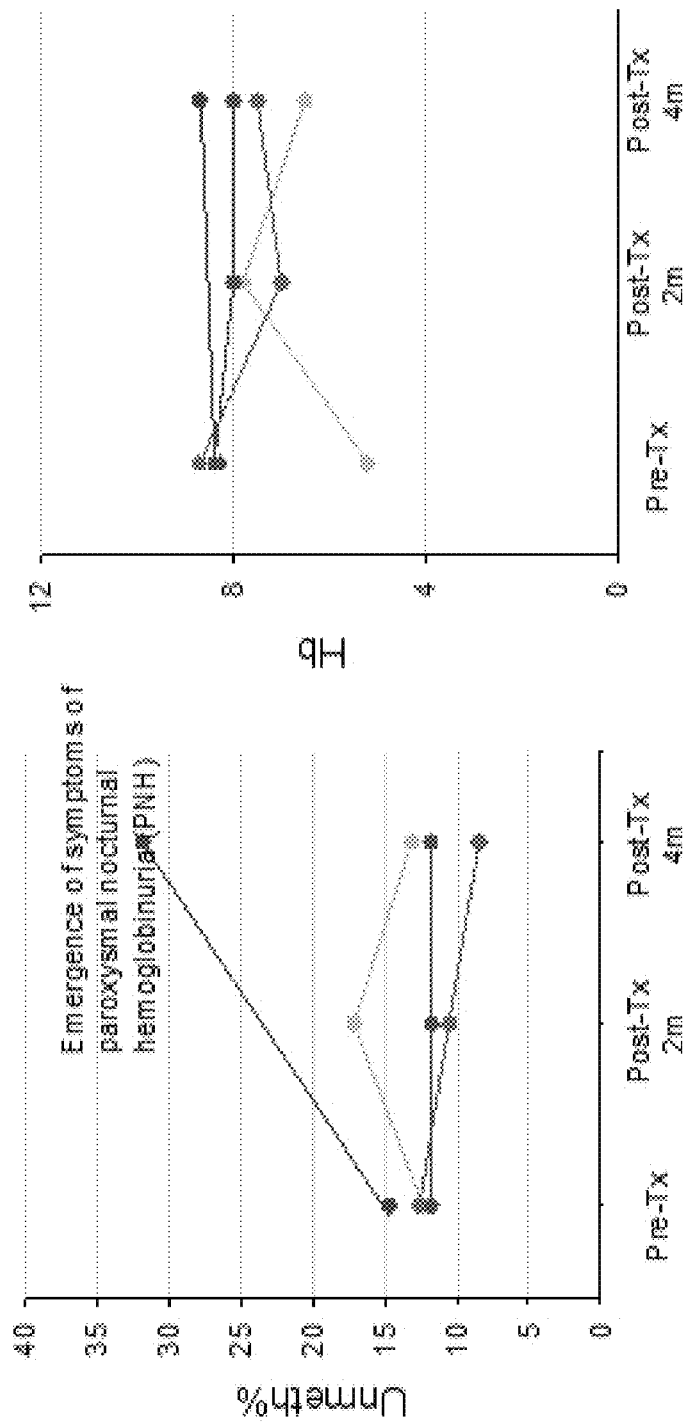
FIG. 23A shows the serial change of plasma Unmeth % at the erythroblast DMR in patients with aplastic anemia receiving anti-thymocyte globulin (ATG) treatment or cyclosporin as immunosuppressive therapy according to embodiments of the present invention.
FIG. 23B shows the serial change of hemoglobin in the patients with aplastic anemia receiving treatment.

FIG. 23A shows the serial change of plasma Unmeth % at the erythroblast DMR in patients with aplastic anemia receiving anti-thymocyte globulin (ATG) treatment or cyclosporin as immunosuppressive therapy according to embodiments of the present invention. Among three patients, there was no change in the Unmeth % in plasma. One patient demonstrated a significant increase in Unmeth %. This occurred at the same time as the emergence of symptoms of paroxysmal nocturnal hemoglobinuria (PNH) clone, namely passing dark urine containing hemoglobins. Such a symptom can be used to determine that the patient is not responding to treatment, even though Unmeth % increased. PNH is known for its occurrence in patients with aplastic anemia and has the pathophysiologic mechanism of hemolytic anemia. An increase in Unmeth % reflects the increase in erythropoietic activity as a result of hemolysis from PNH.

FIG. 23B shows the serial change of hemoglobin in the patients with aplastic anemia receiving treatment. The hemoglobin levels do not increase significantly. These results show that the plasma Unmeth % reflects the change in erythropoiesis activity during the treatment course, which is not changed in erythropoiesis activity since all patients did not respond to the treatment, as exemplified by the lack of change of hemoglobin shown in FIG. 23B.

Figure 24A:
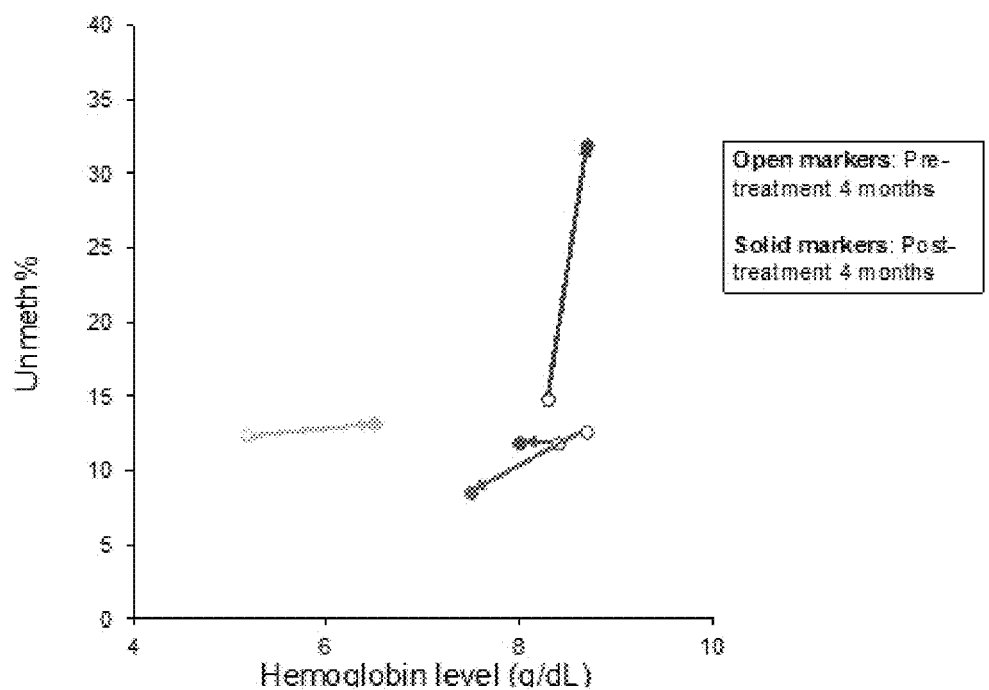
FIGS. 24A and 24B show plots of Unmeth % in plasma against hemoglobin concentrations in the four patients with aplastic anemia.
Figure 24B:
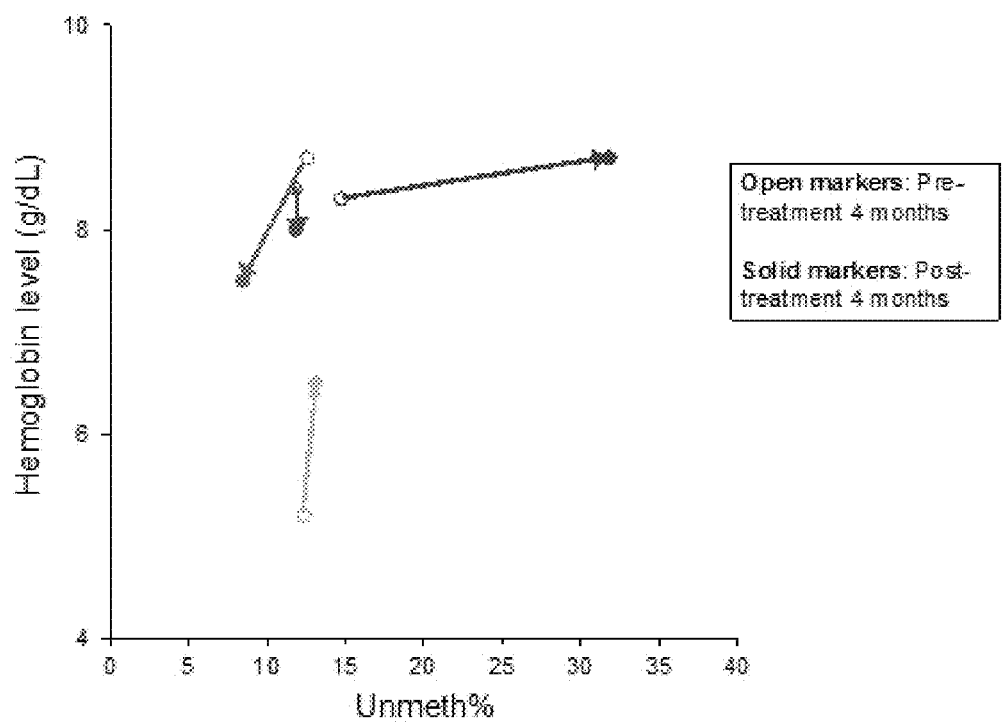

FIGS. 24A and 24B show plots of Unmeth % in plasma against hemoglobin concentrations in the four patients with aplastic anemia. Each line corresponds to one patient and tracks the change in Unmeth % and hemoglobin level before treatment and after 4 months of treatment. FIG. 23A shows that Unmeth % did not change significantly, except for the patient with PNH. FIG. 23B shows that hemoglobin levels did change, but not significantly.

VIII. USE OF ABSOLUTE CONCENTRATION OF ERYTHROID DNA

To measure an amount of erythroid DNA in plasma/serum, some embodiments use the parameter E % (also referred to as Unmeth %) at a hypomethylation marker, although a hypermethylation marker specific to a cell lineage could also be used, if present. E % corresponds to the amount of erythroblast DNA normalized to the total amount of DNA (which is mostly hypermethylated) in the sample.

An alternative parameter is to measure an absolute concentration of erythroid DNA per unit volume of plasma. For the calculation of the E %, embodiments can measure the unmethylated DNA absolute concentration and methylated DNA absolute concentration. In the digital PCR assay, each dot can represent one DNA molecule (e.g., as shown in FIGS. 2A and 2B). The counts of methylated and unmethylated DNA can be directly counted. In the previous sections, a normalized value (e.g., E %) was calculated, but embodiments can also use the absolute concentration of unmethylated molecules for a hypomethylation marker or absolute concentration of methylated molecules for a hypermethylation marker.

Figure 25:
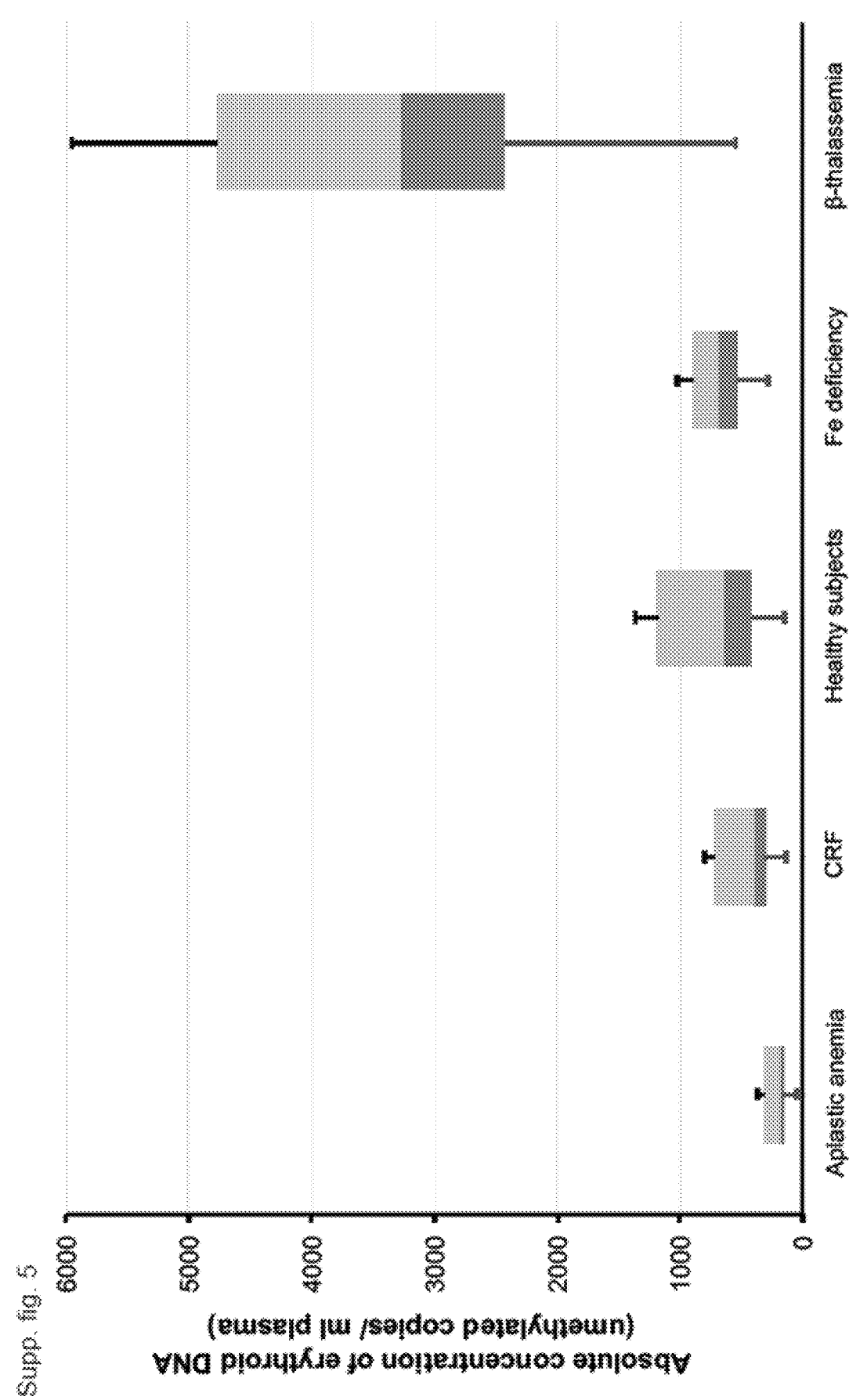
FIG. 25 illustrates box-and-whisker plots showing the absolute concentration of erythroid DNA at the FECH gene-associated DMR (copies/ml plasma) in healthy subjects and anemic patients according to embodiments of the present invention.

FIG. 25 illustrates box-and-whisker plots showing the absolute concentration of erythroid DNA at the FECH gene-associated DMR (copies/ml plasma) in healthy subjects and anemic patients according to embodiments of the present invention. The boxes and the lines inside represent the interquartile range and the median values, respectively. The top and bottom whiskers represent the maximum and minimum values.

As shown in FIG. 25, while separate clusters between the different patient groups could be observed using the absolute concentration of erythroid DNA, the normalized values allow a better separation between the groups. Theoretically, the E % parameter of plasma could also be affected by the concentrations of circulating DNA of non-erythroid origin, e.g., myeloid- or lymphoid-derived DNA. For example, in anemic conditions when the other hematopoietic lineages are also affected (e.g. aplastic anemia or myelodysplastic syndrome), the altered release of erythroid DNA might be masked in some of these cases.

IX. OTHER HEMATOLOGICAL LINEAGES

This plasma DNA-based approach for hematological assessment can be generalized to markers of other hematological cell lineages, e.g. the myeloid, lymphoid, and megakaryocytic series. Previous work on using hematological lineage-specific DNA methylation markers has focused on whole blood, or blood cells (Houseman E A, et al. Current Environmental Health Reports 2015; 2: 145-154). Our data presented above clearly show that the plasma DNA does contain information that is not present in the blood cells. Hence, the analysis of plasma DNA using epigenetic markers from multiple hematological cell lineages can provide valuable diagnostic information regarding the hematological system of an individual. It is thus a noninvasive replacement of bone marrow biopsy. Assays can be designed that specifically detect the methylation signature of a particular cell lineage in plasma or serum so that the activity of different cell lineage in the bone marrow can be monitored.

Such an approach would be useful for the assessment of many clinical scenarios, including, but not limited to the following disorders. Example relevant lineages are provided for the disorders.

1. hematological malignancy, e.g., leukemia and lymphoma (lymphoid cells lineage)
2. bone marrow disorders, e.g. aplastic anemia, myelofibrosis (myeloid cells and lymphoid cells lineage)
3. monitoring of the immune system and its functions: e.g. immunodeficiency and the mounting of an immune response during disease and treatments (lymphoid cells lineage)
4. drug effects on the bone marrow, e.g. azathioprine (myeloid cells lineage)
5. autoimmune disorders with hematological manifestations, e.g. immune thrombocytopenia (ITP), which is a condition characterized by low platelet count but with a normal bone marrow. Plasma DNA analysis using blood lineage markers, e.g. megakaryocytic markers, would provide valuable diagnostic information on such a condition. (megakaryotic markers)
6. Infections with hematological complications, e.g. infection with parvovirus B19, which can be complicated with a reduction in erythropoiesis or even a more severe aplastic crisis. (erythroid lineage)

X. METHOD

Figure 26:
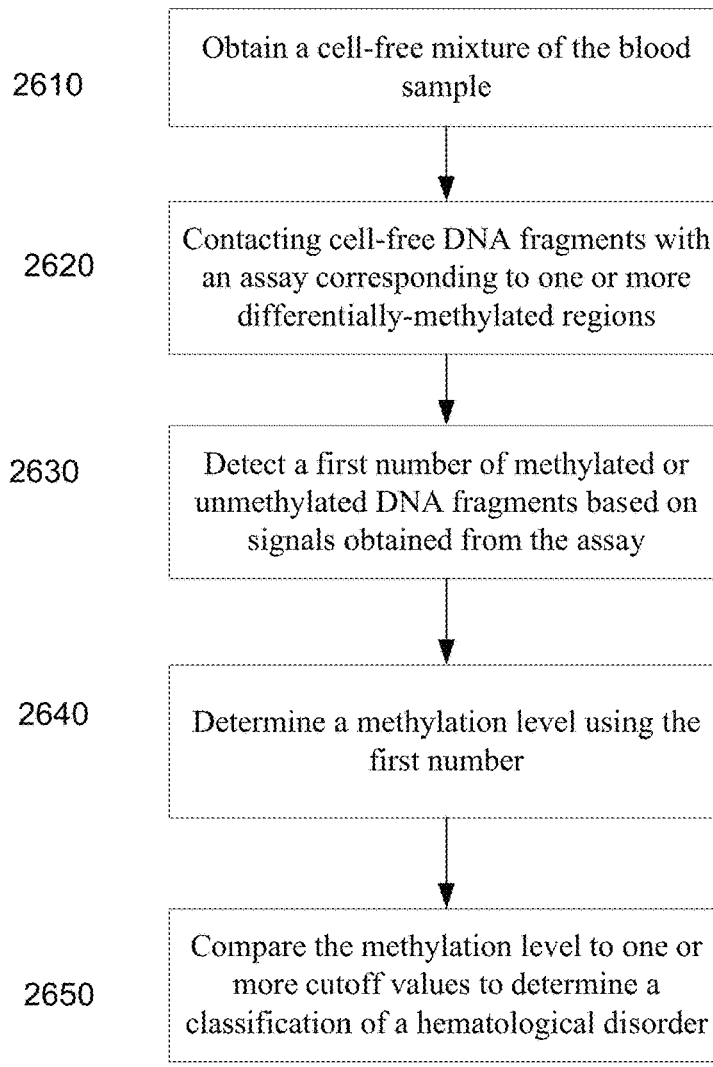
FIG. 26 is a flowchart illustrating a method of analyzing a blood sample of a mammal according to embodiments of the present invention.

FIG. 26 is a flowchart illustrating a method 2600 of analyzing a blood sample of a mammal according to embodiments of the present invention. Parts of method 2600 may be performed manually and other parts may be performed by a computer system. In one embodiment, a system may perform all steps. For instance, a system can includes robotic elements (e.g., to obtain a sample and perform an assay), a detection system for detecting signals from an assay, and a computer system for analyzing the signals. Instructions for controlling such a system may be stored in one or more computer readable media, such as configuration logic of a field programmable gate array (FPGA), flash memory, and/or a hard drive. FIG. 27 shows such a system At block 2610, a cell-free mixture of the blood sample is obtained. Examples of a cell-free mixture include plasma or serum. The cell-free mixture can include cell-free DNA from a plurality of cell lineages.

In some embodiments, a blood sample is separated to obtain the cell-free mixture. Plasma and serum are different. Both correspond to the fluid portion of blood. To get plasma, anticoagulant is added to a blood sample to prevent it from clotting. To get serum, a blood sample is allowed to clot. Therefore, the clotting factors would be consumed during the clotting process. With regard to circulating DNA, some DNA would be released from the blood cells to the fluid portion during clotting. Therefore, serum has higher DNA concentration compared with plasma. The DNA from cells during clotting may dilute the DNA that is specific to plasma. Therefore, plasma can be advantageous.

At block 2620, DNA fragments in the cell-free mixture are contacted with an assay corresponding to one or more differentially-methylated regions. Each of the one or more differentially-methylated regions (DMRs) is specific to a particular hematological cell lineage by being hypomethylated or hypermethylated relative to other cell lineages. Examples of DMRs for the erythroblast cell lineage are provided herein.

In various embodiments, the assay can involve PCR or sequencing, and thus be a PCR assay or a sequencing assay. Contacting the DNA fragments can involve a flow cell, droplets, beads, or other mechanisms to provide an interaction of the assay with the DNA fragments. Examples for such an assay include whole-genome bisulfite sequencing, targeted bisulfite sequencing (by hybridization capture or amplicon-sequencing), other methylation-ware sequencing (e.g. single molecule real-time (SMRT) DNA sequencing by Pacific Biosciences), real-time methylation-specific PCR, and digital PCR. Further examples of assays usable for method 300 are described herein, e.g., in section XII. Although examples use erythroblasts, other cell lineages, including other hematological cell lineages, may be used.

At block 2630, a first number of methylated or unmethylated DNA fragments is detected in the cell-free mixture at the one or more differentially-methylated regions based on signals obtained from the assay. The assays can provide various signals, such as light or electrical signals. The signals can provide a specific signal per DNA fragment, or an aggregate signal indicating a total number of DNA fragments with the methylation signature (e.g., as in real-time PCR).

In one embodiment, sequencing can be used to obtain a sequence read for a DNA fragment, and the DNA fragment can be aligned to a reference genome. If the DNA fragment aligns to one of the DMRs, then a counter can be incremented. Given that the signal is from a particular methylated of unmethylated assay, the DNA fragment can be assumed to have that methylation signature. In another embodiment, a read from PCR (e.g., a light signal from a positive well) can be used to increment such a counter.

At block 2640, a methylation level is determined using the first number. The first methylation level can be normalized or be an absolute concentration, e.g., per volume of the biological sample. An example of an absolute concentration is provided in FIG. 25. Examples of a methylation level that is normalized includes E % (also referred to as Unmeth %).

For a normalized value, a methylation level can be determined using the first number and a total number of DNA fragments in the cell-free mixture at the one or more differentially-methylated regions. As described above, the methylation level can be a percentage of unmethylated DNA fragments. In other embodiments, the percentage can be of methylated DNA fragments, which would have an inverse relationship relative to the above examples for the erythroblasts. In various implementations, the methylation level can be determined using a percentage across all sites in the DMR, by an average of an individual percentage at each site, or a weighted average at each site.

At block 2650, the methylation level is compared to one or more cutoff values as part of determining a classification of a hematological disorder in the mammal. The one or more cutoff values can be selected from empirical data, e.g., as shown in FIGS. 8-10 and 12-14. The cutoff values can be selected to provide optimal sensitivity and specificity for providing an accurate classification of a hematological disorder, e.g., based on supervised learning from a dataset of known samples to be normal and to have a disorder.

As an example for determining a cutoff value, a plurality of samples can be obtained. Each sample is known to have a particular classification of the hematological disorder, e.g., via other techniques, as would be known to one skilled in the art. The plurality of samples having at least two classification of the hematological disorder, e.g., having the disorder and not having the disorder. Different types of disorders can also be included, e.g., as shown in FIG. 10. A methylation level of the one or more differentially-methylated regions can be determined for each of the plurality of samples, as the data points in FIGS. 8-10 and 12-14.

A first set of samples can be identified that have a first classification of the hematological disorder, e.g., the first classification being healthy. The first set can be clustered together, e.g., as shown in FIGS. 8-10 and 12-14. A second set of samples can be identified that have a second classification of the hematological disorder. The second set can be patients that have the disorder, or a different type of disorder than the first classification. The two classifications can correspond to varying degrees of having the same disorder. When the first set of samples collectively have a statistically higher methylation level than the second set of samples, a cutoff value can be determined that discriminates between the first set of samples and the second set of samples within a specified specificity and sensitivity. Thus, a balance between specificity and sensitivity can be used to select an appropriate cutoff value.

XI. SUMMARY

RBCs are the most abundant cell type in the peripheral blood but do not have a nucleus. In this disclosure, we determined that cells of the erythroid lineage contribute a significant proportion of plasma DNA pool. Before this work, it was known that hematopoietic cells contribute significantly to the circulating DNA pool (13, 14), but many workers had assumed that such hematopoietic DNA was only from the white cell lineages (15). More recent results using DNA methylation markers have shown that plasma DNA carries DNA methylation signatures of neutrophils and lymphocytes (15).

Using high-resolution reference methylomes of a number of tissues including erythroblasts (18, 20), we distinguished the erythroid-derived DNA molecules from DNA of other tissue types in the plasma DNA pool. Our digital PCR assays based on the erythroblast-specific methylation signature enabled us to perform quantitative analysis of such DNA molecules in plasma. This approach allowed us to demonstrate the presence of a significant amount of erythroid DNA in the plasma DNA pool of healthy subjects.

Our results are consistent with cells of the erythroid lineage in the bone marrow contributing DNA into the plasma. The corollary of this hypothesis is that the quantitative analysis of erythroid DNA in plasma reflects marrow erythropoietic activity, and thus can help in the differential diagnosis of anemia. We have established reference values for erythroid DNA in the plasma of healthy subjects. We have further demonstrated that anemic patients would have either increased or decreased proportion of circulating erythroid DNA, depending on the exact nature of their pathologies and treatments. In particular, we could distinguish the two bone marrow failure syndromes, i.e., aplastic anemia (AA) and myelodysplastic syndrome (MDS), among our recruited patients through analysis of the percentage of erythroid DNA in plasma.

The reticulocyte count could be used to provide information on the marrow response in anemic patients. Among the 11 patients with beta-thalassemia we studied, four patients had reticulocyte counts in peripheral blood of less than 1%, the detection limit. For the other seven patients, the reticulocyte counts ranged from 1% to 10%. For all the nine patients with aplastic anemia, their reticulocyte counts were less than 1% regardless of whether they were receiving regular transfusion or not. Thus, the reticulocyte count may not clearly define normal and reduced erythropoietic activity in the bone marrow due to the high imprecision of the automated methods at low concentrations of reticulocytes (35, 36).

We have demonstrated that analysis of the reticulocyte count or reticulocyte index could not distinguish anemic causes with reduced erythropoietic activity in our cohort of patients (FIGS. 11A and 11B). Our results indicate that the plasma Unmeth % (e.g., as shown in FIG. 10) is more accurate than reticulocyte count in reflecting the erythropoietic activity in the bone marrow than reticulocyte count. There was no correlation between plasma Unmeth % and reticulocyte counts or reticulocyte index among all the patients with both parameters measured (P=0.3, linear regression), as shown in FIGS. 11A and 11B.

Similarly, the presence of an abnormally high number of erythroblasts in the peripheral blood implies abnormal erythropoiesis stress (37). However, absence of erythroblasts in the peripheral blood does not imply normal or reduced erythropoietic activity. Conversely, the quantitative analysis of plasma erythroblast-derived DNA yields information on the marrow erythropoietic activity that is not provided by the conventional hematological parameters from the peripheral blood.

For beta-thalassemia and aplastic anemia, these two conditions are typically diagnosed by the analysis of iron in blood and hemoglobin pattern. But, both beta-thalassemia and aplastic anemia exhibit low hemoglobin levels, and thus such a technique does not discriminate between beta-thalassemia and aplastic anemia. Using Unmeth % can provide more specificity by enabling discrimination between these two disorders, as shown in FIGS. 8 and 10.

Unmeth % can also be used to monitoring treatment. For example, the analysis of Unmeth % in patients with iron deficiency anemia can be used for the monitoring of the bone marrow response to oral iron therapy, as shown in FIG. 9. In some patients, the oral iron supplement may not be effectively absorbed through the gastrointestinal tract. As a result, erythropoiesis would not be increased after starting the treatment. The absence of increase in Unmeth % can be used as an indicator for the poor response to oral iron treatment so that other treatments, such as parenteral iron treatment (e.g., iron dextran, ferric gluconate, and iron sucrose), can be initiated. Alternatively, the absence of increase in Unmeth % can be used to discontinue (stop) treatment, thereby saving costs of an ineffective treatment. In another implementation, the absence of increase in Unmeth % can be used to identify when to increase a dose of treatment, e.g., increase a dosage of iron. When there is an increase in Unmeth %, the treatment can be continued. If the increase in Unmeth % is sufficiently high (e.g., based on a threshold), then treatment can be stopped as it can be assumed that the erythropoietic activity has reached a sufficient level for eventually returning the hemoglobin level to a healthy level, thereby avoiding excess treatment that is costly or potentially harmful.

Accordingly, a mammal can be treated for the hematological disorder in response to determining that the classification of the hematological disorder indicates the mammal has the hematological disorder. After treatment, the assay can be repeated to determine an updated methylation level, and it can be determined whether to continue to perform the treatment based on the updated methylation level. In one embodiment, determining whether to continue to perform the treatment can includes: stopping the treatment, increasing a dose of the treatment, or pursuing a different treatment when the updated methylation level has not changed relative to the methylation level to within a specified threshold. In another embodiment, determining whether to continue to perform the treatment can include: continuing the treatment when the updated methylation level has changed relative to the methylation level to within a specified threshold.

As another example of monitoring treatment, Unmeth % analysis can be used to determine if the ineffective erythropoiesis in thalassemia patients has been adequately suppressed by treatment, for example, by blood transfusion. Extramedullary erythropoiesis is a cause of bone deformities in thalassemia patients. Extramedullary erythropoiesis can be suppressed by transfusion and the restoration of hemoglobin levels. Unmeth % can show the patient's response to these treatments, and the failure to suppress Unmeth % may be used to indicate that the treatment should be intensified.

Unmeth % can also be used to differentiate patients with iron deficiency alone from those with iron deficiency together with other causes of anemia, for example, anemia due to chronic illnesses. Patients with iron deficiency alone would be expected to have increased Unmeth % after iron treatment, but those with multiple causes of anemia would not show a response of elevation of Unmeth %.

Accordingly, we have demonstrated that the percentage of circulating erythroid DNA is increased in response to iron therapy in patients with iron-deficiency anemia, thus reflecting an increase in the marrow erythropoietic activity. The dynamic change in the proportion of erythroid DNA shows that quantification of plasma erythroid DNA permits the noninvasive monitoring of the related cellular process. The rapid kinetics of plasma DNA (e.g. with half-lives of the orders of tens of minutes (38, 39)) suggests that such monitoring might provide near real-time results. Similarly, the percentage of circulating cell-free DNA of other cell lineages also permits the noninvasive monitoring of the related cellular process in bone marrow for the other cell lineages.

The current work serves as a proof to demonstrate the presence of nuclear materials of hematopoietic progenitor and precursor cells in circulation. Furthermore, the presence of circulating DNA released from precursor cells of other hematopoietic lineages could also be used.

In summary, we have demonstrated that erythroid DNA contributes to a significant proportion of the plasma DNA pool. The discovery has filled an important gap in our understanding of the basic biology of circulating nucleic acids. Clinically, the measurement of erythroid DNA in plasma has opened up a new approach for the investigation and monitoring of different types of anemia and herald the beginning of a new family of cell-free DNA-based hematological tests.

XII. MATERIALS AND METHODS

This section describes techniques that have been and may be used for implementing embodiment.

A. Sample Collection and Preparation

In some embodiments, formalin-fixed paraffin-embedded (FFPE) of 12 types of normal tissues (liver, lung, esophagus, stomach, small intestines, colon, pancreas, adrenal gland, urinary bladder, heart, brain and placenta), each with four cases, were retrieved from the anonymized surgical specimens. The tissues collected were confirmed to be normal on histological examination. DNA was extracted from the FFPE tissues protocol using the QIAamp DNA Mini Kit (Qiagen) with modifications of the manufacturer's protocol for fixed tissues. Deparaffinization solution (Qiagen) was used instead of xylene to remove the paraffin. An additional step of incubation at 90° C. for 1 hour was performed after lysis with Buffer ATL and protease K for reversal of formaldehyde modification of nucleic acids.

To prepare erythroblast-enriched sample for analysis, 1-3 mL of umbilical cord blood was collected into an EDTA-containing tube from each of eight pregnant women immediately after delivery. Mononuclear cells were isolated from the cord blood samples using density gradient centrifugation with Ficoll-Paque PLUS solution (GE Healthcare). 1×10$^8$ isolated mononuclear cells were incubated with 1 mL of the mixture of two antibodies: fluorescein isothiocyanate (FITC)-conjugated anti-CD235a (Miltenyi Biotec) and phycoerythrin (PE)-conjugated anti-CD71 (Miltenyi Biotec) in a 1:10 dilution in phosphate-buffered saline (PBS) for 30 minutes in the dark at 4° C. The CD235a+ and CD71+ cells were then sorted by the BD FACSAria Fusion flow cytometer (BD Biosciences) for enrichment of erythroblasts (1). The CD235a+CD71+ cells from the eight cases were pooled for downstream analysis. DNA was extracted from the pooled CD235a+CD71+ cells using the QIAamp DNA Blood Mini Kit (Qiagen) with the manufacturer's instructions.

Peripheral blood samples were collected into EDTA-containing tubes and immediately stored at 4° C. 10 mL of peripheral venous blood was collected from each patient. Plasma isolation was performed within 6 hours after blood withdrawal. Plasma DNA was extracted from 4 mL of plasma. Plasma and buffy coat DNA was obtained as previously described (2). In brief, the blood samples were first centrifuged at 1,600 g for 10 minutes at 4° C. and the plasma portion was re-centrifuged at 16,000 g for 10 minutes at 4° C. The blood cell portion were collected after re-centrifugation at 2,500 g for 10 minutes to remove any residual plasma. DNA from plasma and buffy coat was extracted using the QIAamp DSP DNA Mini Kit (Qiagen) and QIAamp DNA Blood Mini Kit (Qiagen), respectively.

B. Bisulfite Conversion of DNA

Plasma DNA and genomic DNA extracted from blood cells and FFPE tissues were subjected to two rounds of bisulfite treatment using Epitect Plus Bisulfite Kit (Qiagen) according to the manufacturer's instructions (3).

In one embodiment, DNA extracted from the biological samples is first treated with bisulfite. Bisulfite treatment will convert unmethylated cytosines into uracils while leaving methylated cytosines unchanged. Therefore, after bisulfite conversion, methylated and unmethylated sequences can be differentiated based on the sequence difference at the CpG dinucleotides. For the analysis of plasma samples presented in selected examples of this application, DNA was extracted from 2-4 mL plasma. For the analysis of DNA extracted from blood cells, 1 μg of DNA was used for downstream analysis in the examples. In other embodiments, other volumes of plasma and amounts of DNA could be used.

In the examples in this application, two rounds of bisulfite treatment were performed on each sample using EpiTect Bisulfite Kit according to manufacturer's instructions. The bisulfite-converted plasma DNA was eluted in 50 μL water. The bisulfite-converted cellular DNA was eluted in 20 μL water, and then diluted by 100 folds for downstream analysis.

C. Methylation Assays

Various methylation assays can be used to quantify the amount of DNA from a particular cell lineage.

1. PCR Assays

Two digital PCR assays were developed, one targeting bisulfate-converted unmethylated sequences and the other targeting methylated sequences, for each of the three erythroblast-specific DMRs. The primers and probes design for the assays are listed in supplemental Table 7.

FECH Gene Marker Site (Chr 18: 55250563-55250585)

TABLE 7

Oligonucleotide sequences for the digital PCR assays for the methylated and unmethylated sequences of the erythroblast-specific DMRs. The underlined nucleotides in the reverse primers and the probes represent the differentially methylated cytosines at the CpG sites.

| Assay for methylated sequences (SEQ ID NOS: 9, 7, 8) | |
|---|---|
| Forward primer (degenerate base denoted by Y) | 5'-TTGAAGAGAATTTGATGGTAYGGGTA-3' |
| Reverse primer | 5'-CAAATCTCTCTAATTTCCGAACACG-3' |
| Fluorescence probe | 5'-(VIC)-TGCGTGGCGTAGAG-MGB-3' |

TABLE 7-continued

Oligonucleotide sequences for the digital PCR assays for the
methylated and unmethylated sequences of the erythroblast-specific
DMRs. The underlined nucleotides in the reverse primers and the probes
represent the differentially methylated cytosines at the CpG sites.

Assay for unmethylated sequences (SEQ ID NOS: 9, 5, 6)

| | |
|---|---|
| Forward primer (degenerate base denoted by Y) | 5'-TTGAAGAGAATTTGATGGTAYGGGTA-3' |
| Reverse primer | 5'-CTCAAATCTCTCTAATTTCCAAACACA-3' |
| Fluorescence probe | 5'-(FAM)-TTGTGTGGTGTAGAGAG-MGB-3' |

Ery-1 marker site (chr 12: 48227688-48227701)

| | |
|---|---|
| Forward primer (degenerate base denoted by Y) | 5'-GAGTAAGYGGAGTTGTTGGTATTATGG-3' (SEQ ID NO: 10) |
| Reverse primer | 5'-ACCCTCAACCCAACTCCTAAAATAAC-3' (SEQ ID NO: 11) |
| Fluorescence probe for methylated sequences | 5'-(VIC)-TCGGGTTAGGCGTGCGT-MGB-3' (SEQ ID NO: 12) |
| Fluorescence probe for unmethylated sequences | 5'-(FAM)-TTGGGTTAGGTGTGTGTTT-MGB-3' (SEQ ID NO: 6) |

Ery-2 marker site (chr 12: 48228144-48228154)

| | |
|---|---|
| Forward primer (degenerate base denoted by Y) | 5'-ATGTAGAGTTGGTAAAGATAAYGGAAGG-3' (SEQ ID NO: 13) |
| Reverse primer | 5'-CATTACTACCCTAAACAAAACCAAACC-3' (SEQ ID NO: 14) |
| Fluorescence probe for methylated sequences | 5'-(VIC)-AAGGTTCGTAGTACGTCGTA-MGB-3' (SEQ ID NO: 15) |
| Fluorescence probe for unmethylated sequences | 5'-(FAM)-AAGGTTTGTAGTATGTTGTAG-MGB-3' (SEQ ID NO: 16) |

VIC and FAM denote the 2 fluorescent reporters.

As examples, a PCR reaction can include 50 μL with 3 μL of bisulfite converted template DNA, a final concentration of 0.3 μM of each primer, 0.5 μM of MgCl$_2$, and 25 μL of the 2×KAPA HiFi HotStart Uracil ReadyMix. The following PCR thermal profile can be used: 95° C. for 5 minutes, and 35 cycles of 98° C. 20 seconds, 57° C. for 15 seconds, and 72° C. for 15 seconds, followed by a final extension step of 72° C. for 30 seconds. In other embodiments, non-preferential genome-wide sequencing can be performed in combination with alignment, but such a procedure may not be as cost-effective.

In some embodiments, for the digital PCR analysis of a sample, a 20 μL reaction mix was prepared after bisulfite treatment. In one embodiment, the reaction mix contained 8 μL of template DNA, a final concentration of 450 nM of each the two forward primers, 900 nM of the reverse primer, and 250 nM for probes. In other embodiments, a total volume of 20 μL of each reaction mix was prepared, containing 8 uL of template DNA, a final concentration of 900 nM of the forward primers, 900 nM of the reverse primer and 250 nM of the probe. The reaction mix was then used for droplets generation using the BioRad QX200 ddPCR droplet generator. Typically 20,000 droplets would be generated for each sample. In some implementations, the droplets were transferred into a clean 96-well plate followed by thermal cycling using an identical condition for both methylated and unmethylated specific assays: 95° C.×10 minutes (1 cycle), 40 cycles of 94° C.×15 seconds and 60° C.×1 minute, 98° C.×10 minutes (1 cycle), followed by a 12° C. hold step. After the PCR, the droplets for each sample were analyzed by the BioRad QX200 droplet reader and the results were interpreted using the QuantaSoft (version 1.7) software.

2. Examples of Other Methylation Assays

Other examples of methylation-aware sequencing include using a single molecule sequencing platform that would allow the methylation status of DNA molecules (including N$^6$-methyladenine, 5-methylcytosine and 5-hydroxymethylcytosine) to be elucidated directly without bisulfite conversion (AB Flusberg et al. 2010 Nat Methods; 7: 461-465; J Shim et al. 2013 Sci Rep; 3:1389); or through the immunoprecipitation of methylated cytosine (e.g. by using an antibody against methylcytosine or by using a methylated DNA binding protein or peptide (LG Acevedo et al. 2011 Epigenomics; 3: 93-101) followed by sequencing; or through the use of methylation-sensitive restriction enzymes followed by sequencing.

In some embodiments, the methylation levels for the genomic sites in the DNA mixture can be determined using whole genome bisulfite sequencing. In other embodiments, the methylation levels for the genomic sites can be determined using methylation microarray analysis, such as the Illumina HumanMethylation450 system, or by using methylation immunoprecipitation (e.g. using an anti-methylcytosine antibody) or treatment with a methylation-binding protein followed by microarray analysis or DNA sequencing, or by using methylation-sensitive restriction enzyme treatment followed by microarray or DNA sequencing, or by using methylation aware sequencing e.g. using a single molecule sequencing method (e.g. by a nanopore sequencing (Schreiber et al. Proc Natl Acad Sci 2013; 110: 18910-18915) or by the Pacific Biosciences single molecule real time analysis (Flusberg et al. Nat Methods 2010; 7: 461-465)). Tissue-specific methylation levels can be measured in a same way. As another example, targeted bisulfite sequencing, methylation-specific PCR, non-bisulfite based methylation-aware sequencing (e.g. by single molecule sequencing platforms (Powers et al. Efficient and accurate whole genome assembly and methylome profiling of E. coli. BMC Genomics. 2013; 14:675) can be used for the analysis of the methylation level of the plasma DNA for plasma DNA methylation deconvolution analysis. Accordingly, methylation-aware sequencing results can be obtained in a variety of ways.

D. Statistical Analysis

Pearson's correlation was used to study the correlation between the percentage of erythroid DNA (E % (FECH)) and the percentage of erythroblasts among peripheral white blood cells measured by a hematology analyzer in β-thalassemia major patients. Pearson's correlation was also used to study the correlation between the paired E % (FECH) results in the plasma DNA and in the buffy coat DNA of healthy controls. The Wilcoxon signed-rank test was used to compare the difference between the E % in the plasma DNA and the paired buffy coat DNA of healthy subjects. The Mann-Whitney rank-sum test was used to compare the difference between the E % in the plasma DNA of healthy subjects and anemic patients of different disease groups.

We also developed our bioinformatics pipelines to mine the erythroblast-specific DMRs based on our criteria described in the main text. The bioinformatics pipeline may be implemented in various platforms, e.g., the Perl platform.

XIII. EXAMPLE SYSTEMS

FIG. 27 illustrates a system 2700 according to an embodiment of the present invention. The system as shown includes a sample 2705, such as cell-free DNA molecules within a sample holder 2710, where sample 2705 can be contacted with an assay 2708 to provide a signal of a physical characteristic 2715. An example of a sample holder can be a flow cell that includes probes and/or primers of an assay or a tube through which a droplet moves (with the droplet including the assay). Physical characteristic 2715, such as a fluorescence intensity value, from the sample is detected by detector 2720. Detector can take a measurement at intervals (e.g., periodic intervals) to obtain data points that make up a data signal. In one embodiment, an analog to digital converter converts an analog signal from the detector into digital form at a plurality of times. A data signal 2725 is sent from detector 2720 to logic system 2730. Data signal 2725 may be stored in a local memory 2735, an external memory 2740, or a storage device 2745.

Logic system 2730 may be, or may include, a computer system, ASIC, microprocessor, etc. It may also include or be coupled with a display (e.g., monitor, LED display, etc.) and a user input device (e.g., mouse, keyboard, buttons, etc.). Logic system 2730 and the other components may be part of a stand-alone or network connected computer system, or they may be directly attached to or incorporated in a thermal cycler device. Logic system 2730 may also include optimization software that executes in a processor 2750. Logic system 1030 may include a computer readable medium storing instructions for controlling system 1000 to perform any of the methods described herein.

Figure 28:
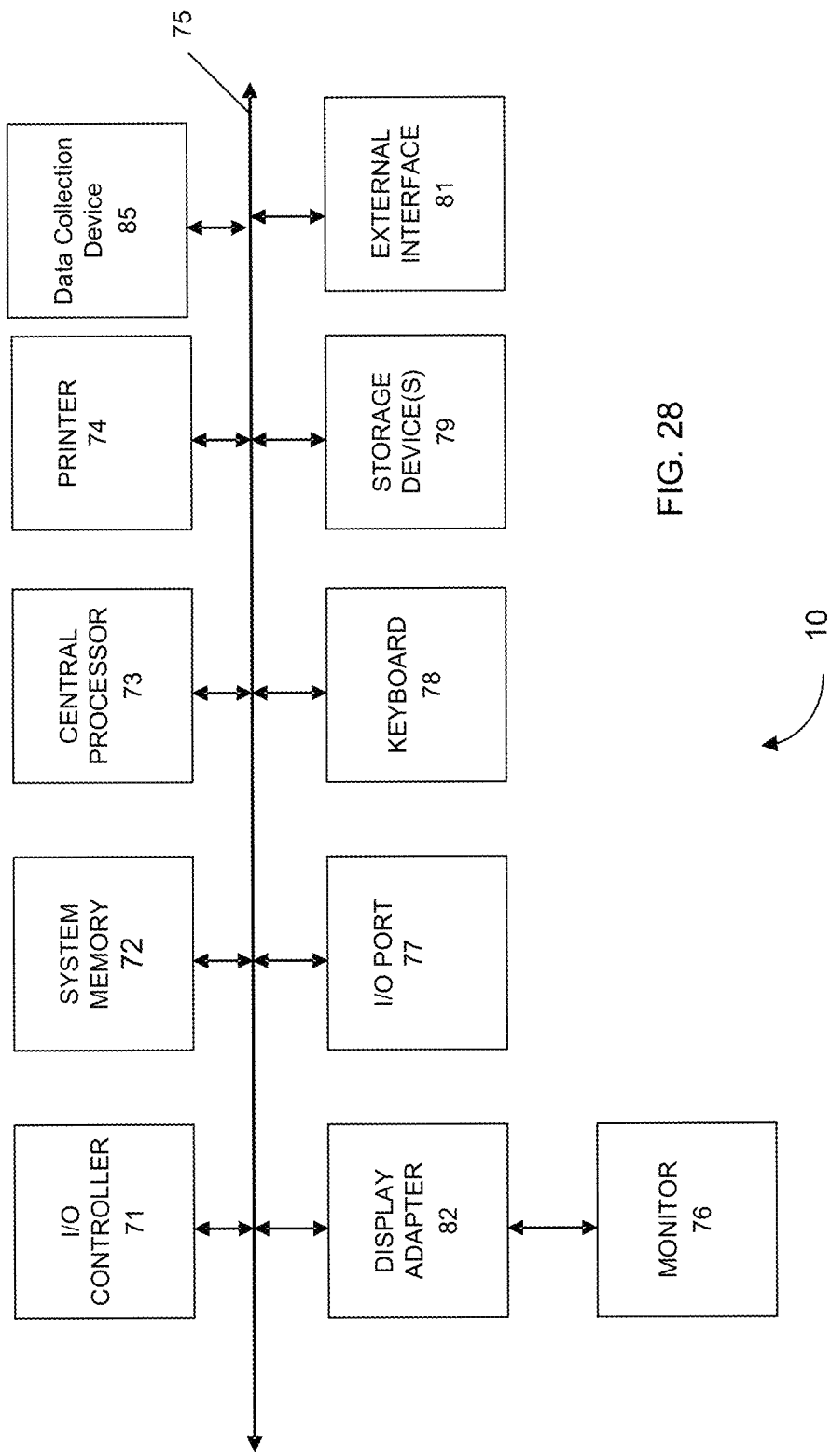
FIG. 28 shows a block diagram of an example computer system usable with system and methods according to embodiments of the present invention.

Any of the computer systems mentioned herein may utilize any suitable number of subsystems. Examples of such subsystems are shown in FIG. 28 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 28 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

XIV. REFERENCES

The following references are referred to above and are incorporated by reference in their entirety for all purposes.
1. Lo Y M, Chan K C, Sun H, Chen E Z, Jiang P, Lun F M, et al. Maternal plasma DNA sequencing reveals the genome-wide genetic and mutational profile of the fetus. Sci Transl Med 2010; 2:61ra91.
2. Chiu R W, Chan K C, Gao Y, Lau V Y, Zheng W, Leung T Y, et al. Noninvasive prenatal diagnosis of fetal chromosomal aneuploidy by massively parallel genomic sequencing of DNA in maternal plasma. Proc Natl Acad Sci USA 2008; 105:20458-63.
3. New M I, Tong Y K, Yuen T, Jiang P, Pina C, Chan K C, et al. Noninvasive prenatal diagnosis of congenital adrenal hyperplasia using cell-free fetal DNA in maternal plasma. J Clin Endocrinol Metab 2014; 99:E1022-30.
4. Bianchi D W, Parker R L, Wentworth J, Madankumar R, Saffer C, Das A F, et al. DNA sequencing versus standard prenatal aneuploidy screening. N Engl J Med 2014; 370:799-808.
5. Chiu R W, Akolekar R, Zheng Y W, Leung T Y, Sun H, Chan K C, et al. Non-invasive prenatal assessment of trisomy 21 by multiplexed maternal plasma DNA sequencing: Large scale validity study. BMJ 2011; 342: c7401.
6. Bayindir B, Dehaspe L, Brison N, Brady P, Ardui S, Kammoun M, et al. Noninvasive prenatal testing using a novel analysis pipeline to screen for all autosomal fetal aneuploidies improves pregnancy management. Eur J Hum Genet 2015; 23:1286-93.
7. Scheffer P G, van der Schoot C E, Page-Christiaens G C, de Haas M. Noninvasive fetal blood group genotyping of rhesus D, c, E and of K in alloimmunised pregnant women: Evaluation of a 7-year clinical experience. BJOG 2011; 118:1340-8.
8. Lo Y M, Chan L Y, Lo K W, Leung S F, Zhang J, Chan A T, et al. Quantitative analysis of cell-free Epstein-Barr virus DNA in plasma of patients with nasopharyngeal carcinoma. Cancer Res 1999; 59:1188-91.
9. Leary R J, Sausen M, Kinde I, Papadopoulos N, Carpten J D, Craig D, et al. Detection of chromosomal alterations in the circulation of cancer patients with whole-genome sequencing. Sci Transl Med 2012; 4:162ra54.
10. Chan K C, Jiang P, Zheng Y W, Liao G J, Sun H, Wong J, et al. Cancer genome scanning in plasma: Detection of tumor-associated copy number aberrations, single-nucleotide variants, and tumoral heterogeneity by massively parallel sequencing. Clin Chem 2013; 59:211-24.
11. Bettegowda C, Sausen M, Leary R J, Kinde I, Wang Y, Agrawal N, et al. Detection of circulating tumor DNA in early- and late-stage human malignancies. Sci Transl Med 2014; 6:224ra24.
12. Izumchenko E, Chang X, Brait M, Fertig E, Kagohara L T, Bedi A, et al. Targeted sequencing reveals clonal genetic changes in the progression of early lung neoplasms and paired circulating DNA. Nat Commun 2015; 6:8258.
13. Lui Y Y, Chik K W, Chiu R W, Ho C Y, Lam C W, Lo Y M. Predominant hematopoietic origin of cell-free DNA in plasma and serum after sex-mismatched bone marrow transplantation. Clin Chem 2002; 48:421-7.
14. Zheng Y W, Chan K C, Sun H, Jiang P, Su X, Chen E Z, et al. Nonhematopoietically derived DNA is shorter than hematopoietically derived DNA in plasma: A transplantation model. Clin Chem 2012; 58:549-58.
15. Sun K, Jiang P, Chan K C, Wong J, Cheng Y K, Liang R H, et al. Plasma DNA tissue mapping by genome-wide methylation sequencing for noninvasive prenatal, cancer, and transplantation assessments. Proc Natl Acad Sci USA 2015; 112:E5503-12.
16. Keerthivasan G, Wickrema A, Crispino J D. Erythroblast enucleation. Stem Cells Int 2011; 2011:139851.
17. Chasis J A, Mohandas N. Erythroblastic islands: Niches for erythropoiesis. Blood 2008; 112:470-8.
18. Adams D, Altucci L, Antonarakis S E, Ballesteros J, Beck S, Bird A, et al. BLUEPRINT to decode the epigenetic signature written in blood. Nat Biotechnol 2012; 30:224-6.
19. Martens J H, Stunnenberg H G. BLUEPRINT: Mapping human blood cell epigenomes. Haematologica 2013; 98:1487-9.

20. Kundaje A, Meuleman W, Ernst J, Bilenky M, Yen A, Heravi-Moussavi A, et al. Integrative analysis of 111 reference human epigenomes. Nature 2015; 518:317-30.
21. Chim S S, Tong Y K, Chiu R W, Lau T K, Leung T N, Chan L Y, et al. Detection of the placental epigenetic signature of the maspin gene in maternal plasma. Proc Natl Acad Sci USA 2005; 102:14753-8.
22. Lehmann-Werman R, Neiman D, Zemmour H, Moss J, Magenheim J, Vaknin-Dembinsky A, et al. Identification of tissue-specific cell death using methylation patterns of circulating DNA. Proc Natl Acad Sci USA 2016; 113: E1826-34.
23. Lun F M, Chiu R W, Sun K, Leung T Y, Jiang P, Chan K C, et al. Noninvasive prenatal methylomic analysis by genomewide bisulfite sequencing of maternal plasma DNA. Clin Chem 2013; 59:1583-94.
24. Chan K C, Zhang J, Hui A B, Wong N, Lau T K, Leung T N, et al. Size distributions of maternal and fetal DNA in maternal plasma. Clin Chem 2004; 50:88-92.
25. Yu S C, Chan K C, Zheng Y W, Jiang P, Liao G J, Sun H, et al. Size-based molecular diagnostics using plasma DNA for noninvasive prenatal testing. Proc Natl Acad Sci USA 2014; 111:8583-8.
26. Ferreira G C, Franco R, Lloyd S G, Moura I, Moura J J, Huynh B H. Structure and function of ferrochelatase. J Bioenerg Biomembr 1995; 27:221-9.
27. Buoro S, Vavassori M, Pipitone S, Benegiamo A, Lochis E, Fumagalli S, et al. Evaluation of nucleated red blood cell count by Sysmex XE-2100 in patients with thalassaemia or sickle cell anaemia and in neonates. Blood Transfus 2015; 13:588-94.
28. Killick S B, Bown N, Cavenagh J, Dokal I, Foukaneli T, Hill A, et al. Guidelines for the diagnosis and management of adult aplastic anaemia. Br J Haematol 2016; 172:187-207.
29. Young N S. Acquired aplastic anemia. Ann Intern Med 2002; 136:534-46.
30. Eschbach J W. Erythropoietin 1991—an overview. Am J Kidney Dis 1991; 18:3-9.
31. Schrier S L. Pathobiology of thalassemic erythrocytes. Curr Opin Hematol 1997; 4:75-8.
32. Kasper C K, Whissell D Y, Wallerstein R O. Clinical aspects of iron deficiency. JAMA 1965; 191:359-63.
33. Bejar R, Steensma D P. Recent developments in myelodysplastic syndromes. Blood 2014; 124:2793-803.
34. Arber D A, Orazi A, Hasserjian R, Thiele J, Borowitz M J, Le Beau M M, et al. The 2016 revision to the world health organization classification of myeloid neoplasms and acute leukemia. Blood 2016; 127:2391-405.
35. Buttarello M. Laboratory diagnosis of anemia: Are the old and new red cell parameters useful in classification and treatment, how? Int J Lab Hematol 2016; 38 Suppl 1:123-32.
36. Buttarello M, Bulian P, Farina G, Temporin V, Toffolo L, Trabuio E, Rizzotti P. Flow cytometric reticulocyte counting. Parallel evaluation of five fully automated analyzers: An NCCLS-ICSH approach. Am J Clin Pathol 2001; 115:100-11.
37. Danise P, Maconi M, Barrella F, Di Palma A, Avino D, Rovetti A, et al. Evaluation of nucleated red blood cells in the peripheral blood of hematological diseases. Clin Chem Lab Med 2012; 50:357-60.
38. Lo Y M, Zhang J, Leung T N, Lau T K, Chang A M, Hjelm N M. Rapid clearance of fetal DNA from maternal plasma. Am J Hum Genet 1999; 64:218-24.
39. To E W, Chan K C, Leung S F, Chan L Y, To K F, Chan A T, et al. Rapid clearance of plasma Epstein-Barr virus DNA after surgical treatment of nasopharyngeal carcinoma. Clin Cancer Res 2003; 9:3254-9.

What is claimed is:

1. A method of analyzing a blood sample of a mammal, wherein the mammal is a human, the method comprising:
   obtaining a cell-free mixture of the blood sample, the cell-free mixture including cell-free DNA from a plurality of cell lineages;
   performing an assay by contacting DNA fragments in the cell-free mixture with reagents hybridizing to one or more differentially-methylated regions, each of the one or more differentially-methylated regions specific to a particular hematological cell lineage by being hypomethylated or hypermethylated relative to other cell lineages, wherein at least one of the one or more differentially-methylated regions is in the FECH gene, in chromosome 12 at genomic coordinates 48227688-48227701 in human reference genome hg19, or in chromosome 12 at genomic coordinates 48228144-48228154 in the human reference genome hg19, wherein the particular hematological cell lineage is red blood cells;
   detecting a first number of methylated or unmethylated DNA fragments in the cell-free mixture at the one or more differentially-methylated regions based on signals obtained from the assay;
   determining a methylation level using the first number;
   comparing the methylation level to one or more cutoff values;
   measuring a hemoglobin level of the blood sample;
   comparing the hemoglobin level to a hemoglobin threshold; and
   determining a classification of a hematological disorder in the mammal based on the comparing of the methylation level to the one or more cutoff values and the comparing of the hemoglobin level to the hemoglobin threshold, wherein the hematological disorder is anemia, the classification including a quantification of erythropoietic activity.

2. The method of claim 1, further comprising:
   determining a total number of DNA fragments in the cell-free mixture at the one or more differentially-methylated regions; and
   determining the methylation level using the first number and the total number.

3. The method of claim 1, further comprising:
   determining a volume of the cell-free mixture; and
   determining the methylation level using the first number and the volume of the cell-free mixture.

4. The method of claim 1, wherein obtaining the cell-free mixture includes:
   separating the cell-free mixture from the blood sample, the cell-free mixture comprising plasma or serum.

5. The method of claim 1, further comprising identifying one of the one or more differentially-methylated regions by:

obtaining methylation indexes of a plurality of sites for each of the plurality of cell lineages, including the particular hematological cell lineage and the other cell lineages;

at each site of the plurality of sites, comparing the methylation indexes of the plurality of cell lineages;

identifying one or more sites of the plurality of sites that have a methylation index in the particular hematological cell lineage that is below/above a first methylation threshold and methylation indexes in each of the other cell lineages that are above/below a second methylation threshold; and identifying the one of the one or more differentially-methylated regions that contains the one or more sites.

6. The method of claim 1, further comprising determining the one or more cutoff values, including:

obtaining a plurality of samples, each sample known to have a particular classification of the hematological disorder, the plurality of samples having at least two classifications of the hematological disorder;

determining a methylation level of the one or more differentially-methylated regions for each of the plurality of samples;

identifying a first set of samples that have a first classification of the hematological disorder;

identifying a second set of samples that have a second classification of the hematological disorder, the first set of samples collectively having a statistically higher methylation level than the second set of samples; and determining a cutoff value that discriminates between the first set of samples and the second set of samples within a specified specificity and sensitivity.

7. The method of claim 1, wherein determining the classification of the hematological disorder includes identifying a particular type of the hematological disorder.

8. The method of claim 1, further comprising:

determining that the classification of the hematological disorder indicates the mammal has the hematological disorder;

treating the mammal for the hematological disorder in response to determining that the classification of the hematological disorder indicates the mammal has the hematological disorder, the treatment being dependent on the quantification of erythropoietic activity;

after treatment, repeating the assay to determine an updated methylation level; and determining whether to continue to perform the treatment based on the updated methylation level.

9. The method of claim 8, wherein determining whether to continue to perform the treatment includes:

stopping the treatment, increasing a dose of the treatment, or pursuing a different treatment when the updated methylation level has not changed relative to the methylation level to within a specified threshold.

10. The method of claim 8, wherein determining whether to continue to perform the treatment includes:

continuing the treatment when the updated methylation level has changed relative to the methylation level to within a specified threshold.

11. The method of claim 1, further comprising:

determining that the hematological disorder exists based on the comparing of the methylation level to the one or more cutoff values; and performing a bone marrow biopsy in response to determining that the hematological disorder exists.

12. The method of claim 1, wherein the assay is a PCR assay or a sequencing assay.

13. The method of claim 1, wherein the one or more differentially-methylated regions comprise CpG sites.

14. The method of claim 13, wherein a first region of the one or more differentially-methylated regions comprises a plurality of CpG sites that are within 100 bp of each other, and wherein the plurality of CpG sites are all hypomethylated or hypermethylated.

15. The method of claim 14, wherein the plurality of CpG sites span 100 bp or less on a reference genome corresponding to the mammal.

16. The method of claim 1, wherein the classification of the hematological disorder includes increased erythropoietic activity, intermediate erythropoietic activity, or reduced erythropoietic activity.

17. The method of claim 16, wherein the classification of the hematological disorder is increased erythropoietic activity from β-thalassemia.

18. The method of claim 16, wherein the classification of the hematological disorder is intermediate erythropoietic activity from iron deficient anemia.

19. The method of claim 16, wherein the classification of the hematological disorder is reduced erythropoietic activity from aplastic anemia or chronic renal failure.

20. The method of claim 1, wherein the one or more differentially-methylated regions are hypomethylated.

21. The method of claim 1, wherein the cell-free mixture is plasma.

22. The method of claim 1, wherein the one or more differentially-methylated regions is a plurality of differentially-methylated regions that include at least one region in at least two of the FECH gene, chromosome 12 at genomic coordinates 48227688-48227701 in human reference genome hg19, and chromosome 12 at genomic coordinates 48228144-48228154 in the human reference genome hg19.

23. The method of claim 22, wherein the plurality of differentially-methylated regions include at least one region in each of the FECH gene, chromosome 12 at genomic coordinates 48227688-48227701 in human reference genome hg19, and chromosome 12 at genomic coordinates 48228144-48228154 in the human reference genome hg19.

* * * * *

SEQUENCE LISTING

```
<160> NUMBER OF SEQ ID NOS: 16

<210> SEQ ID NO 1
<211> LENGTH: 30
<212> TYPE: DNA
<213> ORGANISM: Artificial Sequence
<220> FEATURE:
<223> OTHER INFORMATION: synthetic nucleotide primer

<400> SEQUENCE: 1
tttagtttat agttgaagag aatttgatgg                                     30

<210> SEQ ID NO 2
<211> LENGTH: 25
<212> TYPE: DNA
<213> ORGANISM: Artificial Sequence
<220> FEATURE:
<223> OTHER INFORMATION: synthetic nucleotide primer

<400> SEQUENCE: 2
aaacccaacc atacaacctc ttaat                                          25

<210> SEQ ID NO 3
<211> LENGTH: 26
<212> TYPE: DNA
<213> ORGANISM: Artificial Sequence
<220> FEATURE:
<223> OTHER INFORMATION: synthetic nucleotide primer

<400> SEQUENCE: 3
```
ttgaagagaa tttgatggta tgggta                                      26

<210> SEQ ID NO 4
<211> LENGTH: 25
<212> TYPE: DNA
<213> ORGANISM: Artificial Sequence
<220> FEATURE:
<223> OTHER INFORMATION: synthetic nucleotide primer

<400> SEQUENCE: 4
tgaagagaat tgatggtac gggta                                        25

<210> SEQ ID NO 5
<211> LENGTH: 27
<212> TYPE: DNA
<213> ORGANISM: Artificial Sequence
<220> FEATURE:
<223> OTHER INFORMATION: synthetic nucleotide primer

<400> SEQUENCE: 5
ctcaaatctc tctaatttcc aaacaca                                     27

<210> SEQ ID NO 6
<211> LENGTH: 17
<212> TYPE: DNA
<213> ORGANISM: Artificial Sequence
<220> FEATURE:
<223> OTHER INFORMATION: synthetic nucleotide probe
<220> FEATURE:
<221> NAME/KEY: modified_base
<222> LOCATION: (1)..(1)
<223> OTHER INFORMATION: 5' Thymine labeled with FAM
<220> FEATURE:
<221> NAME/KEY: modified_base
<222> LOCATION: (17)..(17)
<223> OTHER INFORMATION: 3' Guanine with conjugated minor groove binder
      (MGB) group

<400> SEQUENCE: 6
ttgtgtggtg tagagag                                                17

<210> SEQ ID NO 7
<211> LENGTH: 25
<212> TYPE: DNA
<213> ORGANISM: Artificial Sequence
<220> FEATURE:
<223> OTHER INFORMATION: synthetic nucleotide primer

<400> SEQUENCE: 7
caaatctctc taatttccga acacg                                       25

<210> SEQ ID NO 8
<211> LENGTH: 14
<212> TYPE: DNA
<213> ORGANISM: Artificial Sequence
<220> FEATURE:
<223> OTHER INFORMATION: synthetic nucleotide probe
<220> FEATURE:
<221> NAME/KEY: modified_base
<222> LOCATION: (1)..(1)
<223> OTHER INFORMATION: 5' Thymine labeled with VIC
<220> FEATURE:
<221> NAME/KEY: modified_base
<222> LOCATION: (14)..(14)
<223> OTHER INFORMATION: 3' Guanine with conjugated minor groove binder
      (MGB) group

<400> SEQUENCE: 8
tgcgtggcgt agag					14

<210> SEQ ID NO 9
<211> LENGTH: 26
<212> TYPE: DNA
<213> ORGANISM: Artificial Sequence
<220> FEATURE:
<223> OTHER INFORMATION: synthetic nucleotide primer

<400> SEQUENCE: 9
ttgaagagaa tttgatggta ygggta					26

<210> SEQ ID NO 10
<211> LENGTH: 27
<212> TYPE: DNA
<213> ORGANISM: Artificial Sequence
<220> FEATURE:
<223> OTHER INFORMATION: synthetic nucleotide primer

<400> SEQUENCE: 10
gagtaagygg agttgttggt attatgg					27

<210> SEQ ID NO 11
<211> LENGTH: 26
<212> TYPE: DNA
<213> ORGANISM: Artificial Sequence
<220> FEATURE:
<223> OTHER INFORMATION: synthetic nucleotide primer

<400> SEQUENCE: 11
accctcaacc caactcctaa aataac					26

<210> SEQ ID NO 12
<211> LENGTH: 17
<212> TYPE: DNA
<213> ORGANISM: Artificial Sequence
<220> FEATURE:
<223> OTHER INFORMATION: synthetic nucleotide probe
<220> FEATURE:
<221> NAME/KEY: modified_base
<222> LOCATION: (1)..(1)
<223> OTHER INFORMATION: 5' Thymine labeled with VIC
<220> FEATURE:
<221> NAME/KEY: modified_base
<222> LOCATION: (17)..(17)
<223> OTHER INFORMATION: 3' Thymine with conjugated minor groove binder
      (MGB) group

<400> SEQUENCE: 12
tcgggttagg cgtgcgt					17

<210> SEQ ID NO 13
<211> LENGTH: 28
<212> TYPE: DNA
<213> ORGANISM: Artificial Sequence
<220> FEATURE:
<223> OTHER INFORMATION: synthetic nucleotide primer

<400> SEQUENCE: 13
atgtagagtt ggtaaagata ayggaagg					28

<210> SEQ ID NO 14
<211> LENGTH: 27
<212> TYPE: DNA
<213> ORGANISM: Artificial Sequence
<220> FEATURE:
<223> OTHER INFORMATION: synthetic nucleotide primer

```
<400> SEQUENCE: 14
cattactacc ctaaacaaaa ccaaacc                                              27

<210> SEQ ID NO 15
<211> LENGTH: 20
<212> TYPE: DNA
<213> ORGANISM: Artificial Sequence
<220> FEATURE:
<223> OTHER INFORMATION: synthetic nucleotide probe
<220> FEATURE:
<221> NAME/KEY: modified_base
<222> LOCATION: (1)..(1)
<223> OTHER INFORMATION: 5' Adenine labeled with VIC
<220> FEATURE:
<221> NAME/KEY: modified_base
<222> LOCATION: (20)..(20)
<223> OTHER INFORMATION: 3' Adenine with conjugated minor groove binder
      (MGB) group

<400> SEQUENCE: 15
aaggttcgta gtacgtcgta                                                      20

<210> SEQ ID NO 16
<211> LENGTH: 21
<212> TYPE: DNA
<213> ORGANISM: Artificial Sequence
<220> FEATURE:
<223> OTHER INFORMATION: synthetic nucleotide probe
<220> FEATURE:
<221> NAME/KEY: modified_base
<222> LOCATION: (1)..(1)
<223> OTHER INFORMATION: 5' Adenine labeled with VIC
<220> FEATURE:
<221> NAME/KEY: modified_base
<222> LOCATION: (21)..(21)
<223> OTHER INFORMATION: 3' Guanine with conjugated minor groove binder
      (MGB) group

<400> SEQUENCE: 16
aaggtttgta gtatgttgta g                                                    21
```